US009828589B2

(12) United States Patent
Senger et al.

(10) Patent No.: US 9,828,589 B2
(45) Date of Patent: Nov. 28, 2017

(54) ACYLTRANSFERASES AND USES THEREOF IN FATTY ACID PRODUCTION

(71) Applicant: BASF Plant Science Company GmbH, Ludwigshafen (DE)

(72) Inventors: Toralf Senger, Heidelberg (DE); Sten Stymne, Landskrona (SE); Jenny Lindberg Yilmaz, Bfärred (SE)

(73) Assignee: BASF Plant Science Company GmbH, Ludwigshafen (DE)

( * ) Notice: Subject to any disclaimer, the term of this patent is extended or adjusted under 35 U.S.C. 154(b) by 29 days.

(21) Appl. No.: 14/936,807

(22) Filed: Nov. 10, 2015

(65) Prior Publication Data

US 2016/0060606 A1 Mar. 3, 2016

Related U.S. Application Data

(62) Division of application No. 13/319,715, filed as application No. PCT/EP2010/056437 on May 11, 2010, now Pat. No. 9,212,371.

(30) Foreign Application Priority Data

May 13, 2009 (EP) .................................... 09160113

(51) Int. Cl.

| | |
|---|---|
| ***C12N 9/10*** | (2006.01) |
| ***C12N 15/82*** | (2006.01) |
| ***A61K 8/36*** | (2006.01) |
| ***A61K 31/202*** | (2006.01) |
| ***C12P 7/64*** | (2006.01) |
| ***A23K 20/158*** | (2016.01) |
| ***A23L 33/115*** | (2016.01) |
| ***A23L 33/12*** | (2016.01) |
| ***A61K 8/60*** | (2006.01) |
| ***A61Q 19/00*** | (2006.01) |
| ***A23D 9/00*** | (2006.01) |
| ***C11B 1/00*** | (2006.01) |
| ***C11B 1/06*** | (2006.01) |

(52) U.S. Cl.

CPC ............. *C12N 9/1025* (2013.01); *A23D 9/00* (2013.01); *A23K 20/158* (2016.05); *A23L 33/115* (2016.08); *A23L 33/12* (2016.08); *A61K 8/361* (2013.01); *A61K 8/606* (2013.01); *A61K 31/202* (2013.01); *A61Q 19/00* (2013.01); *C11B 1/00* (2013.01); *C11B 1/06* (2013.01); *C12N 9/1029* (2013.01); *C12N 15/8247* (2013.01); *C12P 7/6427* (2013.01); *A23V 2002/00* (2013.01); *A61K 2800/10* (2013.01); *C12Y 203/00* (2013.01)

(58) Field of Classification Search

None

See application file for complete search history.

(56) References Cited

U.S. PATENT DOCUMENTS

| | | | |
|---|---|---|---|
| 5,614,393 | A | 3/1997 | Thomas et al. |
| 6,043,411 | A | 3/2000 | Nishizawa et al. |
| 7,208,590 | B2 | 4/2007 | Mukerji et al. |
| 7,855,321 | B2 | 12/2010 | Renz et al. |
| 2005/0144681 | A9 | 6/2005 | Hood et al. |
| 2006/0168687 | A1 | 7/2006 | Renz et al. |
| 2008/0145867 | A1 | 6/2008 | Zou et al. |

FOREIGN PATENT DOCUMENTS

| | | | |
|---|---|---|---|
| EP | 0 550 162 | A1 | 7/1993 |
| EP | 0 794 250 | A1 | 9/1997 |
| WO | WO-91/13972 | A1 | 9/1991 |
| WO | WO-93/06712 | A1 | 4/1993 |
| WO | WO-93/10241 | A1 | 5/1993 |
| WO | WO-93/11245 | A1 | 6/1993 |
| WO | WO-94/11516 | A1 | 5/1994 |
| WO | WO-94/13814 | A1 | 6/1994 |
| WO | WO-94/18337 | A1 | 8/1994 |
| WO | WO-95/18222 | A1 | 7/1995 |
| WO | WO-95/27791 | A1 | 10/1995 |
| WO | WO-96/21022 | A2 | 7/1996 |
| WO | WO-96/24674 | A1 | 8/1996 |
| WO | WO-97/21340 | A1 | 6/1997 |
| WO | WO-97/30582 | A1 | 8/1997 |
| WO | WO-98/27203 | A1 | 6/1998 |
| WO | WO-98/46763 | A1 | 10/1998 |
| WO | WO-98/46764 | A1 | 10/1998 |
| WO | WO-98/46765 | A1 | 10/1998 |

(Continued)

OTHER PUBLICATIONS

NCBI Accession XP_002907046, 1-acyl-sn-glycerol-3-phosphate acyltransferase, putative [Phytophthora infestans T30-4] Sequence ID: XP_002907046.1 Jul. 22, 2010.*

Abbadi, A., et al., "Transgenic Oilseeds as Sustainable Source of Nutritionally Relevant C20 and C22 Polyunsaturated Fatty Acids?", Eur. J. Lipid Sci. Technol., vol. 103, (2001), pp. 106-113.

Akimoto, M., et al., "Carbon Dioxide Fixation and Polyunsaturated Fatty Acids Production by the Red Alga *Porphyridium cruentum*", Applied Biochemistry and Biotechnology, vol. 73, (1998), pp. 269-278.

Fraser, T., et. al., "Partial Purification and Photoaffinity Labelling of Sunflower Acyl-CoA: Lysophosphatidylcholine Acyltransferase", Biochemical Society Transactions, vol. 28, (2000), pp. 715-718.

Huang, Y.-S., et al., "Cloning of Δ12- and Δ6-Desaturases from *Mortierella alpina* and Recombinant Production of γ-Linolenic Acid in *Saccharomyces cerevisiae*", Lipids, vol. 34, No. 7, (1999), pp. 649-659.

(Continued)

*Primary Examiner* — Eileen O Hara

(74) *Attorney, Agent, or Firm* — Drinker Biddle & Reath LLP

(57) ABSTRACT

The present invention pertains to the recombinant manufacture of polyunsaturated fatty acids. Specifically, it relates to acyltransferase polypeptides, polynucleotides encoding said acyltransferases as well as vectors, host cells, non-human transgenic organisms containing said polynucleotides. Moreover, the present invention contemplates methods for the manufacture of polyunsaturated fatty acids as well as oils obtained by such methods.

23 Claims, 10 Drawing Sheets

(56) References Cited

FOREIGN PATENT DOCUMENTS

| | | | |
|---|---|---|---|
| WO | WO-98/46776 | A2 | 10/1998 |
| WO | WO-98/54302 | A2 | 12/1998 |
| WO | WO-98/54303 | A1 | 12/1998 |
| WO | WO-98/55625 | A1 | 12/1998 |
| WO | WO-98/55631 | A1 | 12/1998 |
| WO | WO-98/55632 | A1 | 12/1998 |
| WO | WO-99/27111 | A1 | 6/1999 |
| WO | WO-99/64616 | A2 | 12/1999 |
| WO | WO-00/18889 | A2 | 4/2000 |
| WO | WO-00/21557 | A1 | 4/2000 |
| WO | WO-00/42195 | A2 | 7/2000 |
| WO | WO-2009/016202 | A2 | 2/2009 |

OTHER PUBLICATIONS

Metz, J. G., et al., "Production of Polyunsaturated Fatty Acids by Polyketide Synthases in Both Prokaryotes and Eukaryotes", Science, vol. 293, (2001), pp. 290-293.

Stukey, J. E., et. al., "The OLE1 Gene of *Saccharomyces cerevisiae* Encodes the Δ9 Fatty Acid Desaturase and Can Be Functionally Replaced by the Rat Stearoyl-CoA Desaturase Gene", The Journal of Biological Chemistry, vol. 265, No. 33, (1990), pp. 20144-20149.

Totani, N., et al., "The Filamentous Fungus *Mortierella alpine*, High in Arachidonic Acid", Lipids, vol. 22, No. 12, (1987), pp. 1060-1062.

Vazhappilly, R., et al., "Heterotrophic Production Potential of Omega-3 Polyunsaturated Fatty Acids by Microalgae and Algae-like Microorganisms", Botanica Marina, vol. 41, (1998), pp. 553-558.

Wada, H., et al., "Enhancement of Chilling Tolerance of a Cyanobacterium by Genetic Manipulation of Fatty Acid Desaturation", Nature, vol. 347, (1990), pp. 200-203.

Zank, T., et al., "Cloning and Functional Expression of the First Plant Fatty Acid Elongase Specific for Δ6-Polyunsaturated Fatty Acids", Biochemical Society Transactions, vol. 28, (2000), pp. 654-658.

Akermoun, M., et al., "Solubilization of the Plastidial Lysophosphatidylcholine Acyltransferase from *Allium porrum* Leaves: Towards Plants Devoid of Eukaryotic Plastid Lipids?", Biochemical Society Transactions, vol. 28, (2000), pp. 713-715.

Cases, S., et al., "Identification of a Gene Encoding an Acyl CoA:Diacylglycerol Acyltransferase, a Key Enzyme in Triacylglycerol Synthesis", PNAS, vol. 95, (1998), pp. 13018-13023.

Frentzen, M., "Acyltransferases from Basic Science to Modified Seed Oils", Fett/Lipid, vol. 100, (1998), pp. 161-166.

Singh, S. P., et al., "Metabolic Engineering of New Fatty Acids in Plants", Curr. Opin. Plant Biol., vol. 8, (2005), pp. 197-203.

Slabas, A. R., et al., "Acyltransferases and Their Role in the Biosynthesis of Lipids—Opportunities for New Oils", J. Plant Physiol., vol. 158, (2001), pp. 505-513.

Stymne, S., et al., "Evidence for the Reversibility of the Acyl-CoA:Lysophosphatidylcholine Acyltransferase in Microsomal Preparations from Developing Safflower (*Carthamus tinctorius* L.) Cotyledons and Rat Liver", Biochem. J., vol. 223, (1984), pp. 305-314.

Tumaney, A. W., et. al., "Synthesis of Azidophospholipids and Labeling of Lysophosphatidylcholine Acyltransferase from Developing Soybean Cotyledons", Biochimica et Biophysica Acta, vol. 1439, (1999), pp. 47-56.

Yamashita, A., et al., "ATP Independent Fatty Acyl-Coenzyme A Synthesis from Phospholipid", The Journal of Biological Chemistry, vol. 276, No. 29, (2001), pp. 26745-26752.

Nath, U. K., et al., "Increasing Erucic Acid Content Through Combination of Endogenous Low Polyunsaturated Fatty Acids Alleles with Ld-LPAAT + Bn-fae1 Transgenes in Rapeseed (*Brassica napus* L.)", Theor. Appl. Genet, vol. 118, No. 4, (2009), pp. 765-773.

Randall, T. A., et al., "Large-Scale Gene Discovery in the Oomycete *Phytophthora infestans* Reveals Likely Components of Phytopathogenicity Shared with True Fungi", Molecular Plant-Microbe Interactions, vol. 18, No. 3, (2005), pp. 229-243.

"PJ021D8 sporangia, purified Phytophthora infestans cDNA, mRNA sequence", Database EMBL Accession No. CV924457, Jan. 28, 2005.

Bates, P. D., et al., "The Pathway of Triacylglycerol Synthesis through Phosphatidylcholine in Arabidopsis Produces a Bottleneck for the Accumulation of Unusual Fatty Acids in Transgenic Seeds", Plant J., vol. 68, No. 3, (2011), pp. 387-399.

Chen, Y., et al., "Phytophthora Infestans Cholinephosphotransferase with Substrate Specificity for Very-Long-Chain Polyunsaturated Fatty Acids", Appl. Environ. Microbiol., vol. 79, No. 5, (2013), pp. 1573-1579.

Kajikawa, M., et al., "Production of Arachidonic and Eicosapentaenoic Acids in Plants Using Bryophyte Fatty Acid Delta6-Desaturase, Delta6-Elongase, and Delta5-Desaturase Genes", Biosci. Biotechnol. Biochem., vol. 72, No. 2, (2008), pp. 435-444.

"SubName: Full=Lysophosphatidylcholine Acyltransferase, Putative {ECO:0000313|EMBL:EEY67958.1}", UniProt Database Accession No. D0NY07, Dec. 15, 2009.

Haas, B. J., et al., "Genome Sequence and Analysis of the Irish Potato Famine Pathogen Phytophthora Infestans", Nature, vol. 461, No. 7262, (2009), pp. 393-398 and Supplementary Information Published Online.

"Phytophthora infestans T30-4 Supercont1.67 Genomic Scaffold, Whole Genome Shotgun Sequence", GenBank Database Accession No. NW_003303692, Jul. 22, 2010.

* cited by examiner

ACYLTRANSFERASES AND USES THEREOF IN FATTY ACID PRODUCTION

RELATED APPLICATIONS

This application is a divisional application of U.S. application Ser. No. 13/319,715 filed Nov. 10, 2011, which is a national stage application under 35 U.S.C. §371 of PCT/EP2010/056437, filed May 11, 2010, which claims benefit of European application 09160113.8, filed May 13, 2009. The entire contents of each of these applications are hereby incorporated by reference herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_074040_0077_01. The size of the text file is 162 KB, and the text file was created on Nov. 9, 2015.

BACKGROUND OF THE INVENTION

Fatty acids and triacylglycerides have a various applications in the food industry, in animal feed, supplement nutrition, and in the cosmetic and pharmacological field. The individual applications may either require free fatty acids or triacylglycerides. In both cases, however, polyunsaturated fatty acids either free or esterified are of pivotal interest for many of the aforementioned applications. In particular, polyunsaturated omega-3-fatty acids and omega-6-fatty acids are important constituents in animal and human food. These fatty acids are supposed to have beneficial effects on the overall health and, in particular, on the central nervous system, the cardivovascular system, the immune system, and the general metabolism. Within traditional food, the polyunsaturated omega-3-fatty acids are mainly found in fish and plant oils. However, in comparison with the needs of the industry and the need for a beneficial diet, this source is rather limited.

The various polyunsaturated fatty acids (PUFA) and PUFA-containing triglycerides are also mainly obtained from microorganisms such as *Mortierella* and *Schizochytrium* or from oil-producing plants such as soybean or oilseed rape, algae such as *Crypthecodinium* or *Phaeodactylum* and others, where they are usually obtained in the form of their triacylglycerides. The free PUFA are usually prepared from the triacylglycerides by hydrolysis. However, long chain polyunsaturated fatty acids (LCPUFA) having a C-18, C-20, C-22 or C-24 fatty acid body, such as docosahexaenoic acid (DHA), eicospentaenoic acid (EPA), arachidonic acid (ARA), dihomo-gamma-linolenic acid or docosahexaenoic acid (DPA) cannot be efficiently isolated from natural oil crop plants such as oilseed rape, soybean, sunflower or safflower. Conventional natural sources of these fatty acids are, thus, merely fish, such as herring, salmon, sardine, redfish, eel, carp, trout, halibut, mackerel, zander or tuna, or algae.

Especially suitable microorganisms for the production of PUFA in industrial scale are microalgae such as *Phaeodactylum tricornutum, Porphoridium* species, *Thraustochytrium* species, *Schizochytrium* species or *Crypthecodinium* species, ciliates such as *Stylonychia* or *Colpidium*, fungi such as *Mortierella, Entomophthora* or *Mucor* and/or mosses such as *Physcomitrella, Ceratodon* and *Marchantia* (Vazhappilly 1998, Botanica Marina 41: 553-558; Totani 1987, Lipids 22: 1060-1062; Akimoto 1998, Appl. Biochemistry and Biotechnology 73: 269-278). Strain selection has resulted in the development of a number of mutant strains of the microorganisms in question which produce a series of desirable compounds including PUFA. However, the mutation and selection of strains with an improved production of a particular molecule such as the polyunsaturated fatty acids is a time-consuming and difficult process. This is why recombinant methods as described above are preferred whenever possible. However, only limited amounts of the desired PUFA or LCPUFA and, in particular, DHA or EPA, can be produced with the aid of the above mentioned microorganisms, and, depending on the microorganism used, these are generally obtained as fatty acid mixtures of, for example, EPA, DPA and DHA.

DESCRIPTION OF RELATED ART

Many attempts in the past have been made to make available genes which are involved in the synthesis of fatty acids or triglycerides for the production of oils in various organisms. Various desaturases have been described in the art; see, e.g., WO 91/13972, WO 93/11245, WO 94/11516, EP-A-0 550 162, WO 94/18337, WO 97/30582, WO 97/21340, WO 95/18222, EP-A-0 794 250, Stukey 1990, J. Biol. Chem., 265: 20144-20149, Wada 1990, Nature 347: 200-203, Huang 1999, Lipids 34: 649-659, WO 93/06712, U.S. Pat. No. 5,614,393, WO 96/21022, WO 00/21557, WO 99/27111, WO 98/46763, WO 98/46764, WO 98/46765, WO 99/64616 or WO 98/46776. These enzymes can be used for the production of unsaturated fatty acids. Thus, due to modern molecular biology, it has become possible to increase at least to some extent the content of the desired polyunsaturated fatty acids and, in particular, the PUFA or LCPUFA in a given organism. Elongases for the production of fatty acids are disclosed in WO2009/016202.

The biosynthesis of LCPUFA and the incorporation of LCPUFA into membrane lipids or triacylglycerides proceeds via various metabolic pathways (Abbadi 2001, European Journal of Lipid Science & Technology 103:106-113). In bacteria such as *Vibrio*, and microalgae, such as *Schizochytrium*, malonyl-CoA is converted into LCPUFA via an LCPUFA-producing polyketide synthase (Metz 2001, Science 293: 290-293; WO 00/42195; WO 98/27203; WO 98/55625). In microalgae, such as *Phaeodactylum*, and mosses, such as *Physcomitrella*, unsaturated fatty acids such as linoleic acid or linolenic acid are converted in a plurality of desaturation and elongation steps to give LCPUFA (Zank 2000, Biochemical Society Transactions 28: 654-658). Desaturation takes place either on acyl groups bound to Coenzyme A (acyl-CoA) or on acyl groups of membrane lipids, whereas elongation is biochemicaly restricted to acyl chains bound to CoA. In mammals, the biosynthesis of DHA comprises a chain shortening via betaoxidation, in addition to desaturation and elongation steps. In microorganisms and lower plants, LCPUFA are present either exclusively in the form of membrane lipids, as is the case in *Physcomitrella* and *Phaeodactylum*, or in membrane lipids and triacylglycerides, as is the case in *Schizochytrium* and *Mortierella*. Incorporation of LCPUFA into lipids and oils, as well as the transfer of the fatty acid moiety (acyl group) between lipids and other molecular species such as acyl-CoA, is catalyzed by various acyltransferases and transacylases. These enzymes are, known to carry out the incorporation or interexchange of saturated and unsaturated fatty acids (Slabas 2001, J. Plant Physiology 158: 505-513, Frentzen 1998, Fett/Lipid 100: 161-166, Cases 1998, Proc. Nat. Acad. Sci.

USA 95: 13018-13023). One group of acyltransferases having three distinct enzymatic activities are enzymes of the "Kennedy pathway", which are located on the cytoplasmic side of the membrane system of the endoplasmic reticulum (ER). The ER-bound acyltransferases in the microsomal fraction use acyl-CoA as the activated form of fatty acids. Glycerol-3-phosphate acyltransferase (GPAT) catalyzes the incorporation of acyl groups at the sn-1 position of glycerol-3-phosphate. 1-Acylglycerol-3-phosphate acyltransferase, also known as lysophosphatidic acid acyltransferase (LPAAT), catalyze the incorporation of acyl groups at the sn-2 position of lysophosphatidic acid (LPA). After dephosphorylation of phosphatidic acid by phosphatidic acid phosphatase (PAP), diacylglycerol acyltransferase (DGAT) catalyzes the incorporation of acyl groups at the sn-3 position of diacylglycerols. Further enzymes directly involved in TAG biosynthesis—apart from the said Kennedy pathway enzymes—are the phospholipid diacylglycerol acyltransferase (PDAT), an enzyme that transfers acyl groups from the sn-2 position of membrane lipids to the sn-3 position of diacylglycerols, and diacylglyceroldiacylglycerol transacylase (DDAT), an enzyme that transfers acylgroups from the sn-2 position of one diacylglycerol-molecule to the sn-3 position of another diacylglycerol-molecule. Lysophospholipid acyltransferase (LPLAT) represents a class of acyltransferases that are capable of incorporating activated acyl groups from acyl-CoA to membrane lipids, and possibly catalyze also the reverse reaction. More specifically, LPLATs can have activity as lysophosphophatidylethanolamine acyltransferase (LPEAT) and lysophosphatidylcholine acyltransferase (LPCAT). Further enzymes, such as lecithin cholesterol acyltransferase (LCAT) can be involved in the transfer of acyl groups from membrane lipids into triacylglycerides, as well.

WO 98/54302 and WO 98/54303 discloses a human LPAAT and its potential use for the therapy of diseases, as a diagnostic, and a method for identifying modulators of the human LPAAT. Moreover, a variety of acyltransferases with a wide range of enzymatic functions have been described in WO 98/55632, WO 98/55631, WO 94/13814, WO 96/24674, WO 95/27791, WO 00/18889, WO 00/18889, WO 93/10241, Akermoun 2000, Biochemical Society Transactions 28: 713-715, Tumaney 1999, Biochimica et Biophysica Acta 1439: 47-56, Fraser 2000, Biochemical Society Transactions 28: 715-7718, Stymne 1984, Biochem. J. 223: 305-314, Yamashita 2001, Journal of Biological Chemistry 276: 26745-26752, and WO 00/18889.

Higher plants comprise PUFA, such as linoleic acid and linolenic acid. However, the LCPUFA ARA, EPA and DHA are not present in the seed oils of higher plants or only in traces (Ucciani: Nouveau Dictionnaire des Huiles Végétales. Technique & Documentation-Lavoisier, 1995. ISBN: 2-7430-0009-0). It is nevertheless highly desirable to produce LCPUFA in higher plants, preferably in oil seeds such as oilseed rape, linseed, sunflower and soybean, since large amounts of high-quality LCPUFA for the various aforementioned applications may be obtained thereby at low costs.

However, one drawback of using transgenic plants expressing various of the aforementioned desaturases and elongases involved in the synthesis of PUFA and LCPUFA is that the latter are not efficiently incorporated into triacylglycerides, but rather into membranes. Furthermore, efficient processing of a given acyl molecule-substrate, e.g. linoleic acid, by a plurality of desaturation and elongation steps towards the desired LCPUFA, e.g. ARA, EPA and/or DHA, is hindered by the requirement to transfer the acyl molecule and its derivatives generated by the elongation and desaturation reactions back and forth between membrane lipids and acyl-CoA. For this reason, intermediates towards desired LCPUFA are incorporated into oil before the synthesis of the desired LCPUFA is complete. These two problems are undesired for the following reasons: First, the main lipid fraction in oil seeds are triacylglycerides. This is why, for economical reasons, it is necessary to concentrate LCPUFA in triacylglycerides. Second, LCPUFA which are incorporated into membranes can modify the physical characteristics of the membranes and thus have harmful effects on the integrity and transport characteristics of the membranes and on the stress tolerance of plants. Third, for efficient LCPUFA synthesis, it is desirable to increase the flux of intermediate-LCPUFA between the two sites of biosynthesis—that is membrane lipids and acyl-CoA—and/or decrease the flux of intermediate-PUFA/-LCPUFA into oil. Transgenic plants which comprise and express genes coding for enzymes of LCPUFA biosynthesis and produce LCPUFA have been described, e.g., in DE 102 19 203 or WO2004/087902. However, these plants produce LCPUFA in amounts which require further optimization for processing the oils present in said plants. Moreover, it was proposed that delta 6 desaturated fatty acids may be shifted into the acyl-CoA pool for increasing efficiency of fatty acid elongation in plants (Singh 2005, Curr. Opin. Plant Biol., 8: 197-203). Another publication demonstrated in *Arabidopsis*, that the additional expression of RcDGAT2 from *Ricinus communis* could increase the storage of hydroxyfatty acids produced by a *Ricinus communis* fatty acid hydroxylase 12 (FAH12) from 17% to 30% in the seed oil.

Accordingly, means for increasing the content of PUFA or LCPUFA, such as EPA and DHA, in triglycerides in, e.g., plant seed oils, are still highly desirable.

BRIEF SUMMARY OF THE INVENTION

The present invention pertains to the recombinant manufacture of polyunsaturated fatty acids. Specifically, it relates to acyltransferase polypeptides, polynucleotides encoding said acyltransferases as well as vectors, host cells, non-human transgenic organisms containing said polynucletides. Moreover, the present invention contemplates methods for the manufacture of polyunsaturated fatty acids as well as oils obtained by such methods.

DETAILED DESCRIPTION OF THE INVENTION

Figure 1:
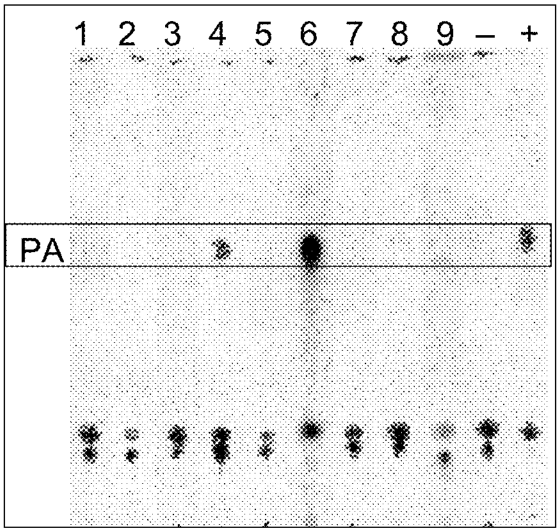
FIG. 1: LPAAT activity assay.

Thus, the present invention relates to a polynucleotide comprising a nucleic acid sequence elected from the group consisting of:

a) a nucleic acid sequence having a nucleotide sequence as shown in any one of SEQ ID NOs: 1, 3, 5, 7, 9, 11, 13, 15, 17, 19, 21, 23, 25, 27, 29, 31, 33, 35, 37, 39, 41, 85, 87, 89, 91, 93, and 95;

b) a nucleic acid sequence encoding a polypeptide having an amino acid sequence as shown in any one SEQ ID NOs: 2, 4, 6, 8, 10, 12, 14, 16, 18, 20, 22, 24, 26, 28, 30, 32, 34, 36, 38, 40, 42, 86, 88, 90, 92, 94 and 96;

c) a nucleic acid sequence being at least 40% identical to the nucleic acid sequence of a) or b), wherein said nucleic acid sequence encodes a polypeptide having acyltransferase activity;

d) a nucleic acid sequence encoding a polypeptide having acyltransferase activity and having an amino acid sequence which is at least 45% identical to the amino acid sequence of any one of a) to c); and e) a nucleic acid sequence which is capable of hybridizing under stringent conditions to any one of a) to d), wherein said nucleic acid sequence encodes a polypeptide having acyltransferase activity.

The term "polynucleotide" as used in accordance with the present invention relates to a polynucleotide comprising a nucleic acid sequence which encodes a polypeptide having acyltransferase activity. Preferably, the polypeptide encoded by the polynucleotide of the present invention having acyltransferas activity upon expression in a plant shall be capable of increasing the amount of PUFA and, in particular, LCPUFA esterified to triglycerides in, e.g., seed oils or the entire plant or parts thereof. Such an increase is, preferably, statistically significant when compared to a LCPUFA producing transgenic control plant which expresses the minimal set of desaturases and elongases required for LCPUFA synthesis but does not express the polynucleotide of the present invention. Such a transgenic plant may, preferably, express desaturases and elongases comprised by the vector LJB765 listed in table 11 of example 5 in WO2009/016202 or a similar set of desaturases and elongases required for DHA synthesis. Whether an increase is significant can be determined by statistical tests well known in the art including, e.g., Student's t-test. More preferably, the increase is an increase of the amount of triglycerides containing LCPUFA of at least 5%, at least 10%, at least 15%, at least 20% or at least 30% compared to the said control. Preferably, the LCPUFA referred to before is a polyunsaturated fatty acid having a C-20, C-22 or C24 fatty acid body, more preferably, EPA or DHA, most preferably, DHA. Suitable assays for measuring the activities mentioned before are described in the accompanying Examples.

The term "acyltransferase activity" or "acyltransferase" as used herein encompasses all enymatic activities and enzymes which are capable of transferring or are involved in the transfer of PUFA and, in particular; LCPUFA from the acly-CoA pool or the membrane phospholipis to the triglycerides, from the acyl-CoA pool to membrane lipids and from membrane lipids to the acyl-CoA pool by a transesterification process. It will be understood that this acyltransferase activity will result in an increase of the LCPUFA esterified to triglycerides in, e.g., seed oils. In particular, it is envisaged that these acyltransferases are capable of producing triglycerides having esterified EPA or even DHA, or that these acyltransferases are capable of enhancing synthesis of desired PUFA by increasing the flux for specific intermediates of the desired PUFA between the acyl-CoA pool (the site of elongation) and membrane lipids (the predominant site of desaturation). Specifically, acyltransferase activity as used herein pertains to lysophospholipid acyltransferase (LPLAT) activity, preferably, lysophosphatidylcholine acyltransferase (LPCAT) or Lysophosphophatidylethanolamine acyltransferase (LPEAT) activity, lysophosphosphatidic acid acyltransferase (LPAAT) activity, phospholipid:diacylglycerol acyltransferase (PDAT) activity, glycerol-3-phosphate acyltransferase (GPAT) activity or diacylglycerol acyltransferase (DGAT), and, more preferably, to PLAT, LPAAT, DGAT, PDAT or GPAT activity.

More preferably, polynucleotides having a nucleic acid sequence as shown in SEQ ID NOs: 1, 3, 5, 7, 9, and 15 encoding polypeptides having amino acid sequences as shown in SEQ ID NOs: 2, 4, 6, 8, 10, and 16 or variants thereof, preferably, exhibit LPLAT activity. Polynucleotides having a nucleic acid sequence as shown in SEQ ID NOs: 7, 11, 13, and 17, encoding polypeptides having amino acid sequences as shown in SEQ ID NOs: 8, 12, 14, and 18 or variants thereof, preferably, exhibit LPAAT activity. Polynucleotides having a nucleic acid sequence as shown in SEQ ID NOs: 19, 21, 23, 25, 27, 29, 31, 33, and 35, encoding polypeptides having amino acid sequences as shown in SEQ ID NOs: 20, 22, 24, 26, 28, 30, 32, 34, and 36 or variants thereof, preferably, exhibit DGAT activity. A polynucleotide having a nucleic acid sequence as shown in SEQ ID NO: 37, encoding a polypeptide having amino acid sequences as shown in SEQ ID NO: 38 or variants thereof, preferably, exhibit PDAT activity. Polynucleotides having a nucleic acid sequence as shown in SEQ ID NOs: 39 and 41, encoding polypeptides having amino acid sequences as shown in SEQ ID NOs: 40 and 42 or variants thereof, preferably, exhibit GPAT activity. A polynucleotide having a nucleic acid sequence as shown in SEQ ID NOs: 85, 87, 89, 91, 93, and 95 encoding a polypeptide having amino acid sequences as shown in SEQ ID NOs: 86, 88, 90, 92, 94 and 96 or variants thereof, preferably, exhibit LPCAT activity.

Moreover, the polynucleotides of the present invention, preferably, encode acyltransferases having defined substrate specificities. Accordingly, the encoded acyltransferases may convert some substrates with higher efficacy than others. Based on said substrate specifities and preferences as well as specific conversion rates, each acyltransferase or acyltransferase family may be identified since the acyltransferases belonging into group of closely related enzymes shall essentially exhibit the essentially identical specificities, preferences or conversion rates and, thus, a acyltransferase-typical biochemical fingerprint. The efficacies of the acyltransferases of the present invention can be tested as described in the accompanying Examples, below.

A polynucleotide encoding a polypeptide having a acyltransferase activity as specified above has been obtained in accordance with the present invention, preferably, from *Phythophthora* infestance. However, orthologs, paralogs or other homologs may be identified from other species.

Thus, the term "polynucleotide" as used in accordance with the present invention further encompasses variants of the aforementioned specific polynucleotides representing orthologs, paralogs or other homologs of the polynucleotide of the present invention. Moreover, variants of the polynucleotide of the present invention also include artificially generated muteins. Said muteins include, e.g., enzymes which are generated by mutagenesis techniques and which exhibit improved or altered substrate specificity, or codon optimized polynucleotides. The polynucleotide variants, preferably, comprise a nucleic acid sequence characterized in that the sequence can be derived from the aforementioned specific nucleic acid sequences shown in any one of SEQ ID NOs: 1, 3, 5, 7, 9, 11, 13, 15, 17, 19, 21, 23, 25, 27, 29, 31, 33, 35, 37, 39, 41, 85, 87, 89, 91, 93, and 95 or by a polynucleotide encoding a polypeptide having an amino acid sequence as shown in any one of SEQ ID NOs: 2, 4, 6, 8, 10, 12, 14, 16, 18, 20, 22, 24, 26, 28, 30, 32, 34, 36, 38, 40, 42, 86, 88, 90, 92, 94 and 96 by at least one nucleotide substitution, addition and/or deletion, whereby the variant nucleic acid sequence shall still encode a polypeptide having a acyltransferase activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N.Y. (1989), 6.3.1-6.3.6. A preferred example for stringent hybridization conditions are hybridization conditions in 6×sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA: DNA hybrids are, preferably, 0.1×SSC and 20° C. to 45° C., preferably between 30° C. and 45° C. The hybridization conditions for DNA:RNA hybrids are, preferably, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequences of the polynucleotides or the amino acid sequences of the polypeptides of the present invention. Oligonucleotides suitable as PCR primers as well as suitable PCR conditions are described in the accompanying Examples. As a template, DNA or cDNA from bacteria, fungi, plants or animals may be used. Further, variants include polynucleotides comprising nucleic acid sequences which are at least 40%, at least 45%, at least 50%, at least 55%, at least 60%, at least 65%, at least 70%, at least 75%, at least 80%, at least 85%, at least 90%, at least 95%, at least 98% or at least 99% identical to the nucleic acid sequences shown in any one of SEQ ID NOs: 1, 3, 5, 7, 9, 11, 13, 15, 17, 19, 21, 23, 25, 27, 29, 31, 33, 35, 37, 39, 41, 85, 87, 89, 91, 93, and 95, preferably, encoding polypeptides retaining a acyltransferase activity as specified above. Moreover, also encompassed are polynucleotides which comprise nucleic acid sequences encoding a polypeptide having an amino acid sequences which are at least 45%, at least 50%, at least 55%, at least 60%, at least 65%, at least 70%, at least 75%, at least 80%, at least 85%, at least 90%, at least 95%, at least 98% or at least 99% identical to the amino acid sequences shown in any one of SEQ ID NOs: 2, 4, 6, 8, 10, 12, 14, 16, 18, 20, 22, 24, 26, 28, 30, 32, 34, 36, 38, 40, 42, 86, 88, 90, 92, 94 and 96 wherein the polypeptide, preferably, retains acyltransferase activity as specified above. The percent identity values are, preferably, calculated over the entire amino acid or nucleic acid sequence region. A series of programs based on a variety of algorithms is available to the skilled worker for comparing different sequences. In a preferred embodiment, the percent identity between two amino acid sequences is determined using the Needleman and Wunsch algorithm (Needleman 1970, J. Mol. Biol. (48):444-453) which has been incorporated into the needle program in the EMBOSS software package (*EMBOSS: The European Molecular Biology Open Software Suite*, Rice, P., Longden, I., and Bleasby, A, Trends in Genetics 16(6), 276-277, 2000), using either a BLOSUM 45 or PAM250 scoring matrix for distantly related proteins, or either a BLOSUM 62 or PAM160 scoring matrix for closer related proteins, and a gap opening penalty of 16, 14, 12, 10, 8, 6, or 4 and a gap entension pentalty of 0.5, 1, 2, 3, 4, 5, or 6. Guides for local installation of the EMBOSS package as well as links to WEB-Services can be found at emboss.sourceforge.net. A preferred, non-limiting example of parameters to be used for aligning two amino acid sequences using the needle program are the default parameters, including the EBLOSUM62 scoring matrix, a gap opening penalty of 10 and a gap extension penalty of 0.5. In yet another preferred embodiment, the percent identity between two nucleotide sequences is determined using the needle program in the EMBOSS software package (*EMBOSS: The European Molecular Biology Open Software Suite*, Rice, P., Longden, I., and Bleasby, A, Trends in Genetics 16(6), 276-277, 2000), using the EDNAFULL scoring matrix and a gap opening penalty of 16, 14, 12, 10, 8, 6, or 4 and a gap extension penalty of 0.5, 1, 2, 3, 4, 5, or 6. A preferred, non-limiting example of parameters to be used in conjunction for aligning two amino acid sequences using the needle program are the default parameters, including the EDNAFULL scoring matrix, a gap opening penalty of 10 and a gap extension penalty of 0.5. The nucleic acid and protein sequences of the present invention can further be used as a "query sequence" to perform a search against public databases to, for example, identify other family members or related sequences. Such searches can be performed using the BLAST series of programs (version 2.2) of Altschul et al. (Altschul 1990, J. Mol. Biol. 215:403-10). BLAST using acyltransferase nucleic acid sequences of the invention as query sequence can be performed with the BLASTn, BLASTx or the tBLASTx program using default parameters to obtain either nucleotide sequences (BLASTn, tBLASTx) or amino acid sequences (BLASTx) homologous to acyltransferase sequences of the invention. BLAST using acyltransferase protein sequences of the invention as query sequence can be performed with the BLASTp or the tBLASTn program using default parameters to obtain either amino acid sequences (BLASTp) or nucleic acid sequences (tBLASTn) homologous to acyltransferase sequences of the invention. To obtain gapped alignments for comparison purposes, Gapped BLAST using default parameters can be utilized as described in Altschul et al. (Altschul 1997, Nucleic Acids Res. 25(17):3389-3402).

TABLE 1

Relation of sequence types of querry and hit sequences for various BLASt programs

| Input query sequence | Converted Query | Algorithm | Converted Hit | Actual Database |
|---|---|---|---|---|
| DNA | | BLASTn | | DNA |
| PRT | | BLASTp | | PRT |
| DNA | PRT | BLASTx | | PRT |
| PRT | | tBLASTn | PRT | DNA |
| DNA | PRT | tBLASTx | PRT | DNA |

A polynucleotide comprising a fragment of any of the aforementioned nucleic acid sequences is also encompassed as a polynucleotide of the present invention. The fragment shall encode a polypeptide which still has acyltransferase activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The variant polynucleotides or fragments referred to above, preferably, encode polypeptides retaining acyltransferase activity to a significant extent, preferably, at least 10%, at least 20%, at least 30%, at least 40%, at least 50%, at least 60%, at least 70%, at least 80% or at least 90% of the acyltransferase activity exhibited by any of the polypeptide shown in any one of SEQ ID NOs: 2, 4, 6, 8, 10, 12, 14, 16, 18, 20, 22, 24, 26, 28, 30, 32, 34, 36, 38, 40, 42, 86, 88, 90, 92, 94 and 96. The activity may be tested as described in the accompanying Examples.

Moreover, the acyltransferases encoded by the variants of the specific polynucleotides and the acyltransferases encoded by the specific polynucleotides referred to above shall, preferably, exhibit the identical or an essentially similar biochemical fingerprint. Accordingly, a variant polynucleotide being at least 40%, at least 45%, at least 50%, at least 55%, at least 60%, at least 65%, at least 70%, at least 75%, at least 80%, at least 85%, at least 90%, at least 95%, at least 98% or at least 99% identical to a polynucleotide as described by any one of the specific SEQ ID Nos. referred to above and which exhibits acyltransferase activity shall preferably also exhibit the same biological fingerprint with respect to the possible substrates. The same applies for polynucleotides which comprise nucleic acid sequences encoding a polypeptide having an amino acid sequences which are at least 45%, at least 50%, at least 55%, at least 60%, at least 65%, at least 70%, at least 75%, at least 80%, at least 85%, at least 90%, at least 95%, at least 98% or at least 99% identical to an amino acid sequences shown in any one of the specific sequences shown in the SEQ ID NOs. wherein the polypeptide retains acyltransferase activity as specified above. Accordingly, these variant polynucleotides shall also encode acyltransferases exhibiting the same biochemical fingerprint with respect to the possible substrates. Preferred biochemical fingerprints for acyltransferases encoded by variant polynucleotides are indicated in Table 2a and b, below for the acyltransferase encoded by the specific polynucleotides, respectively, or in FIGS. 5 to 10.

TABLE 2a

Pattern of substrate specificities and preferences for acyltransferases and C18 substrates

| Acyl-transferase | SEQ ID | Substrate preferences (decreasing from most to less) | | | | | |
|---|---|---|---|---|---|---|---|
| activity | NO: | most | > | > | > | > | less |
| LPAAT | 11/12 | 18:4n-3 | 18:4n-3 | 18:2n-6 | 18:3n-6 | 18:1 | |
| LPAAT | 85/86 | 18:2n-6 | 18:1 | 18:3n-6 | 18:3n-3 | 18:4n-3 | |
| LPLAT (*1) | 7/8 | 18:4n-3 | 18:3n-3 | 18:2n-6 | 18:3n-6 | 18:1 | |
| LPCAT | 15/16 | 18:3n-3 | 18:3n-6 18:4n-3 | 18:2n-6 | 18:1 | | |
| LPLAT (*2) | 7/8 | 18:4n-3 | 18:3n-3 | 18:3n-6 | 18:2n-6 | 18:1 | |
| LPCAT | 89/90 | 18:2n-6 | 18:3n-3 | 18:1 | 18:3n-6 | 18:4n-3 | |
| LPCAT | 91/92 | 18:2n-6 | 18:3n-3 | 18:1 | 18:3n-6 | 18:4n-3 | |
| LPCAT | 93/94 | 18:2n-6 | 18:3n-3 | 18:1 | 18:3n-6 | 18:4n-3 | |
| LPCAT | 95/96 | 18:2n-6 | 18:3n-3 | 18:1 | 18:3n-6 | 18:4n-3 | |
| DGAT | 21/22 | 18:4n-3 | 18:3n-6 18:3n-3 | | | | |
| DGAT | 31/32 | 18:3n-3 | 18:2n-6 | 18:3n-6 | 18:4n-3 | 18:1 | |
| DGAT | 25/26 | 18:3n-3 | 18:2n-6 | 18:3n-6 | 18:1 | 18:4n-3 | |
| DGAT | 35/36 | 18:3n-6 | 18:4n-3 | 18:3n-3 18:2n-6 | | | |

(*1) = Lysophosphatidylcholine as Acly-acceptor;
(*2) = Lysophosphatidylethanolamine as Acyl-acceptor Accordingly, a acyltransferase encoded by a polynucleotide variant of, e.g., the acyltransferase encoded by the polynucleotide shown in SEQ ID NO: 7 or the acyltransferase having an amino acid sequence as shown in SEQ ID NO: 8, preferably, exhibits a biochemical fingerprint characterized in that the substrate preference of the LPCAT activity is decreasing from 18:4 via gamma 18:3, 18:2, and 18:3, towards 18:1. Such a fingerprint can be deduced from the above table mutatis mutandis for the other acyltransferases mentioned.

TABLE 2b

Pattern of substrate specificities and preferences for acyltransferases and C20 substrates

| Acyl-transferase | SEQ ID | Substrate preferences (decreasing from most to less) | | | | | |
|---|---|---|---|---|---|---|---|
| activity | NO: | most | > | > | > | > | less |
| LPAAT | 11/12 | 20:4n-6 | 20:4n-3 | 20:5n-3 | 20:3n-6 | | |
| LPAAT | 85/86 | 20:4n-6 | 20:5n-3 | 20:3n-6 | 20:4n-3 | | |
| LPLAT (*1) | 7/8 | 20:4n-3 | 20:4n-6 | 20:5n-3 | 20:3n-6 | | |
| LPCAT | 15/16 | 20:4n-3 | 20:4n-6 | 20:5n-3 20:3n-6 | | | |
| LPLAT (*2) | 7/8 | 20:4n-3 | 20:4n-6 20:5n-3 | 20:3n-6 | | | |
| LPCAT | 89/90 | 20:3n-6 | 20:4n-3 | 20:5n-3 | | | |
| LPCAT | 91/92 | 20:3n-6 20:4n-3 | 20:5n-3 | | | | |
| LPCAT | 93/94 | 20:4n-3 20:5n-3 | 20:3n-6 | 20:4n-6 | | | |
| LPCAT | 95/96 | 20:5n-3 | 20:3n-6 | | | | |
| DGAT | 21/22 | | | | | | |
| DGAT | 31/32 | 20:4n-3 | 20:3n-6 | 20:5n-3 | 20:4n-6 | | |
| DGAT | 25/26 | 20:4n-3 20:3n-6 | 20:5n-3 | | | | |
| DGAT | 35/36 | 20:4n-3 | 20:3n-6 | | | | |

Accordingly, a acyltransferase encoded by a polynucleotide variant of, e.g., the acyltransferase encoded by the polynucleotide shown in SEQ ID NO: 7 or the acyltransferase having an amino acid sequence as shown in SEQ ID NO: 8, preferably, exhibits a biochemical fingerprint characterized in that the substrate preference of the LPCAT activity is decreasing from 20:4 n-3 via 20:4, and 20:3, towards 20:5. Such a fingerprint can be deduced from the above table mutatis mutandis for the other acyltransferases mentioned.

The polynucleotides of the present invention either essentially consist of the aforementioned nucleic acid sequences or comprise the aforementioned nucleic acid sequences. Thus, they may contain further nucleic acid sequences as well. Preferably, the polynucleotide of the present invention may comprise in addition to an open reading frame further untranslated sequence at the 3' and at the 5' terminus of the coding gene region: at least 500, preferably 200, more preferably 100 nucleotides of the sequence upstream of the 5' terminus of the coding region and at least 100, preferably 50, more preferably 20 nucleotides of the sequence downstream of the 3' terminus of the coding gene region. Furthermore, the polynucleotides of the present invention may encode fusion proteins wherein one partner of the fusion protein is a polypeptide being encoded by a nucleic acid sequence recited above. Such fusion proteins may comprise as additional part other enzymes of the fatty acid or PUFA biosynthesis pathways, polypeptides for monitoring expression (e.g., green, yellow, blue or red fluorescent proteins, alkaline phosphatase and the like) or so called “tags” which may serve as a detectable marker or as an auxiliary measure for purification purposes. Tags for the different purposes are well known in the art and comprise FLAG-tags, 6-histidine-tags, MYC-tags and the like.

The polynucleotide of the present invention shall be provided, preferably, either as an isolated polynucleotide (i.e. purified or at least isolated from its natural context such as its natural gene locus) or in genetically modified or exogenously (i.e. artificially) manipulated form. An isolated polynucleotide can, for example, comprise less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid is derived. The polynucleotide, preferably, is provided in the form of double or single stranded molecule. It will be understood that the present invention by referring to any of the aforementioned polynucleotides of the invention also refers to complementary or reverse complementary strands of the specific sequences or variants thereof referred to before. The polynucleotide encompasses DNA, including cDNA and genomic DNA, or RNA polynucleotides.

However, the present invention also pertains to polynucleotide variants which are derived from the polynucleotides of the present invention and are capable of interefering with the transcription or translation of the polynucleotides of the present invention. Such variant polynucleotides include antisense nucleic acids, ribozymes, siRNA molecules, morpholino nucleic acids (phosphorodiamidate morpholino oligos), triple-helix forming oligonucleotides, inhibitory oligonucleotides, or micro RNA molecules all of which shall specifically recognize the polynucleotide of the invention due to the presence of complementary or substantially complementary sequences. These techniques are well known to the skilled artisan. Suitable variant polynucleotides of the aforementioned kind can be readily designed based on the structure of the polynucleotides of this invention.

Moreover, comprised are also chemically modified polynucleotides including naturally occurring modified polynucleotides such as glycosylated or methylated polynucleotides or artificial modified ones such as biotinylated polynucleotides.

Advantageously, it has been found in accordance with the present invention that the polynucleotides encoding the above mentioned polypeptides having acyltransferase activity and, in particular, LPLAT, LPAAT, DGAT, PDAT and/or GPAT activity, can be used for the manufacture of PUFA and, in particular, LCPUFA when expressed in a transgenic host organism or cell. Specifically, the aforementioned acyltransferase activities will allow for an increase of LCPUFA esterified to triglycerides in seed oils by shifting the said LCPUFA from the acyl-CoA pool (by polypeptides having LPAAT, DGAT or GPAT activity as specified above) and/or from the phospholipid pool (by polypeptides having PDAT activity as specified above) towards the triglyceride pool and/or from the acyl-CoA pool/pospholipid pool to the phospholipid pool/acyl-CoA pool (by polypeptides having LPLAT as specified above) via transesterification. Surprisingly, it was found that the acyltransferases encoded by the polynucleotides of the present invention are also capable of efficiently shifting rather long and highly unsaturated LCPUFA towards the triglyceride pool or between the phospholipid pool and the acyl-CoA pool, in particular, even the long chain intermediates. More surprisingly even, DHA which is known to be incorporated in triglycerides only in very low amounts, if at all, could be efficiently transesterified to triglycerides by the acyltransferases of the invention.

In a preferred embodiment of the polynucleotide of the present invention, said polynucleotide further comprises an expression control sequence operatively linked to the said nucleic acid sequence.

The term “expression control sequence” as used herein refers to a nucleic acid sequence which is capable of governing, i.e. initiating and controlling, transcription of a nucleic acid sequence of interest, in the present case the nucleic sequences recited above. Such a sequence usually comprises or consists of a promoter or a combination of a promoter and enhancer sequences. Expression of a polynucleotide comprises transcription of the nucleic acid molecule, preferably, into a translatable mRNA. Additional regulatory elements may include transcriptional as well as translational enhancers. The following promoters and expression control sequences may be, preferably, used in an expression vector according to the present invention. The cos, tac, trp, tet, trp-tet, lpp, lac, lpp-lac, lacIq, T7, T5, T3, gal, trc, ara, SP6, λ-PR or λ-PL promoters are, preferably, used in Gram-negative bacteria. For Gram-positive bacteria, promoters amy and SPO2 may be used. From yeast or fungal promoters ADC1, AOX1r, GAL1, MFα, AC, P-60, CYC1, GAPDH, TEF, rp28, ADH are, preferably, used. For animal cell or organism expression, the promoters CMV-, SV40-, RSV-promoter (Rous sarcoma virus), CMV-enhancer, SV40-enhancer are preferably used. From plants the promoters CaMV/35S (Franck 1980, Cell 21: 285-294], PRP1 (Ward 1993, Plant. Mol. Biol. 22), SSU, OCS, lib4, usp, STLS1, B33, nos or the ubiquitin or phaseolin promoter. Also preferred in this context are inducible promoters, such as the promoters described in EP 0 388 186 A1 (i.e. a benzylsulfonamide-inducible promoter), Gatz 1992, Plant J. 2:397-404 (i.e. a tetracyclin-inducible promoter), EP 0 335 528 A1 (i.e. a abscisic-acid-inducible promoter) or WO 93/21334 (i.e. a ethanol- or cyclohexenol-inducible promoter). Further suitable plant promoters are the promoter of cytosolic FBPase or the ST-LSI promoter from potato (Stockhaus 1989, EMBO J. 8, 2445), the phosphoribosylpyrophosphate amidotransferase promoter from *Glycine max* (Genbank accession No. U87999) or the node-specific promoter described in EP 0 249 676 A1. Particularly preferred are promoters which enable the expression in tissues which are involved in the biosynthesis of fatty acids. Also particularly preferred are seed-specific promoters such as the USP promoter in accordance with the practice, but also other promoters such as the LeB4, DC3, phaseolin or napin promoters. Further especially preferred promoters are seed-specific promoters which can be used for monocotyledonous or dicotyledonous plants and which are described in U.S. Pat. No. 5,608,152 (napin promoter from oilseed rape), WO 98/45461 (oleosin promoter from Arobidopsis, U.S. Pat. No. 5,504,200 (phaseolin promoter from *Phaseolus vulgaris*), WO 91/13980 (Bce4 promoter from *Brassica*), by Baeumlein et al., Plant J., 2, 2, 1992:233-239 (LeB4 promoter from a legume), these promoters being suitable for dicots. The following promoters are suitable for monocots: Ipt-2 or Ipt-1 promoter from barley (WO 95/15389 and WO 95/23230), hordein promoter from barley and other promoters which are suitable and which are described in WO 99/16890. In principle, it is possible to use all natural promoters together with their regulatory sequences, such as those mentioned above, for the novel process. Likewise, it is possible and advantageous to use synthetic promoters, either additionally or alone, especially when they mediate a seed-specific expression, such as, for example, as described in WO 99/16890. In a particular embodiment, seed-specific promoters are utilized to enhance the production of the desired PUFA or LCPUFA.

The term "operatively linked" as used herein means that the expression control sequence and the nucleic acid of interest are linked so that the expression of the said nucleic acid of interest can be governed by the said expression control sequence, i.e. the expression control sequence shall be functionally linked to the said nucleic acid sequence to be expressed. Accordingly, the expression control sequence and, the nucleic acid sequence to be expressed may be physically linked to each other, e.g., by inserting the expression control sequence at the 5"end of the nucleic acid sequence to be expressed. Alternatively, the expression control sequence and the nucleic acid to be expressed may be merely in physical proximity so that the expression control sequence is capable of governing the expression of at least one nucleic acid sequence of interest. The expression control sequence and the nucleic acid to be expressed are, preferably, separated by not more than 500 bp, 300 bp, 100 bp, 80 bp, 60 bp, 40 bp, 20 bp, 10 bp or 5 bp.

In a further preferred embodiment of the polynucleotide of the present invention, said polynucleotide further comprises a terminator sequence operatively linked to the nucleic acid sequence.

The term "terminator" as used herein refers to a nucleic acid sequence which is capable of terminating transcription. These sequences will cause dissociation of the transcription machinery from the nucleic acid sequence to be transcribed. Preferably, the terminator shall be active in plants and, in particular, in plant seeds. Suitable terminators are known in the art and, preferably, include polyadenylation signals such as the SV40-poly-A site or the tk-poly-A site or one of the plant specific signals indicated in Loke et al. (Loke 2005, Plant Physiol 138, pp. 1457-1468), downstream of the nucleic acid sequence to be expressed.

The present invention also relates to a vector comprising the polynucleotide of the present invention.

The term "vector", preferably, encompasses phage, plasmid, viral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homolgous or heterologous recombination as described in detail below. The vector encompassing the polynucleotide of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride co-precipitation, DEAE-dextranmediated transfection, lipofection, natural competence, carbon-based clusters, chemically mediated transfer, electroporation or particle bombardment. Suitable methods for the transformation or transfection of host cells, including plant cells, can be found in Sambrook et al. (Molecular Cloning: A Laboratory Manual, $2^{nd}$ ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J. Alternatively, a plasmid vector may be introduced by heat shock or electroporation techniques. Should the vector be a virus, it may be packaged in vitro using an appropriate packaging cell line prior to application to host cells.

Preferably, the vector referred to herein is suitable as a cloning vector, i.e. replicable in microbial systems. Such vectors ensure efficient cloning in bacteria and, preferably, yeasts or fungi and make possible the stable transformation of plants. Those which must be mentioned are, in particular, various binary and co-integrated vector systems which are suitable for the T-DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems, preferably, also comprise further cis-regulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. These binary vectors include vectors from the pBIB-HYG, pPZP, pBecks, pGreen series. Preferably used in accordance with the invention are Bin19, pBI101, pBinAR, pGPTV and pCAMBIA. An overview of binary vectors and their use can be found in Hellens et al, Trends in Plant Science (2000) 5, 446-451. Furthermore, by using appropriate cloning vectors, the polynucleotides can be introduced into host cells or organisms such as plants or animals and, thus, be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus 1991, Annu. Rev. Plant Physiol. Plant Molec. Biol. 42, 205-225.

More preferably, the vector of the present invention is an expression vector. In such an expression vector, i.e. a vector which comprises the polynucleotide of the invention having the nucleic acid sequence operatively linked to an expression control sequence (also called "expression cassette") allowing expression in prokaryotic or eukaryotic cells or isolated fractions thereof. Suitable expression vectors are known in the art such as Okayama-Berg cDNA expression vector pcDV1 (Pharmacia), pCDM8, pRc/CMV, pcDNA1, pcDNA3 (Invitrogene) or pSPORT1 (GIBCO BRL). Further examples of typical fusion expression vectors are pGEX (Pharmacia Biotech Inc; Smith 1988, Gene 67:31-40), pMAL (New England Biolabs, Beverly, Mass.) and pRIT5 (Pharmacia, Piscataway, N.J.), where glutathione S-transferase (GST), maltose E-binding protein and protein A, respectively, are fused with the recombinant target protein. Examples of suitable inducible nonfusion *E. coli* expression vectors are, inter alia, pTrc (Amann 1988, Gene 69:301-315) and pET 11d (Studier 1990, Methods in Enzymology 185, 60-89). The target gene expression of the pTrc vector is based on the transcription from a hybrid trp-lac fusion promoter by host RNA polymerase. The target gene expression from the pET 11d vector is based on the transcription of a T7-gn10-lac fusion promoter, which is mediated by a coexpressed viral RNA polymerase (T7 gn1). This viral polymerase is provided by the host strains BL21 (DE3) or HMS174 (DE3) from a resident λ-prophage which harbors a T7 gn1 gene under the transcriptional control of the lacUV 5 promoter. The skilled worker is familiar with other vectors which are suitable in prokaryotic organisms; these vectors are, for example, in *E. coli*, pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667. Examples of vectors for expression in the yeast *S. cerevisiae* comprise pYep Sec1 (Baldari 1987, Embo J. 6:229-234), pMFa (Kurjan 1982, Cell 30:933-943), pJRY88 (Schultz 1987, Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C.A.M.J.J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi (J. W. Bennett & L. L. Lasure, Ed., pp. 396-428: Academic Press: San Diego). Further suitable yeast vectors are, for example, pAG-1, YEp6, YEp13 or pEMBLYe23. As an alternative, the polynucleotides of the present invention can be also expressed in insect cells using baculovirus expression vectors. Baculovirus vectors which are available for the expression of proteins in cultured insect cells (for example Sf9 cells) comprise the pAc series (Smith 1983, Mol. Cell Biol. 3:2156-2165) and the pVL series (Lucklow 1989, Virology 170:31-39).

The polynucleotide of the present invention can be expressed in single-cell plant cells (such as algae), see Falciatore 1999, Marine Biotechnology 1 (3):239-251 and the references cited therein, and plant cells from higher plants (for example Spermatophytes, such as arable crops) by using plant expression vectors. Examples of plant expression vectors comprise those which are described in detail in: Becker 1992, Plant Mol. Biol. 20:1195-1197; Bevan 1984, Nucl. Acids Res. 12:8711-8721; Vectors for Gene Transfer in Higher Plants; in: Transgenic Plants, Vol. 1, Engineering and Utilization, Ed.: Kung and R. Wu, Academic Press, 1993, p. 15-38. A plant expression cassette, preferably, comprises regulatory sequences which are capable of controlling the gene expression in plant cells and which are functionally linked so that each sequence can fulfill its function, such as transcriptional termination, for example polyadenylation signals. Preferred polyadenylation signals are those which are derived from *Agrobacterium tumefaciens* T-DNA, such as the gene 3 of the Ti plasmid pTiACH5, which is known as octopine synthase (Gielen 1984, EMBO J. 3, 835) or functional equivalents of these, but all other terminators which are functionally active in plants are also suitable. Since plant gene expression is very often not limited to transcriptional levels, a plant expression cassette preferably comprises other functionally linked sequences such as translation enhancers, for example the overdrive sequence, which comprises the 5'-untranslated tobacco mosaic virus leader sequence, which increases the protein/RNA ratio (Gallie 1987, Nucl. Acids Research 15:8693-8711). As described above, plant gene expression must be functionally linked to a suitable promoter which performs the expression of the gene in a timely, cell-specific or tissue-specific manner. Promoters which can be used are constitutive promoters (Benfey 1989, EMBO J. 8:2195-2202) such as those which are derived from plant viruses such as 35S CAMV (Franck 1980, Cell 21:285-294), 19S CaMV (see U.S. Pat. No. 5,352,605 and WO 84/02913) or plant promoters such as the promoter of the Rubisco small subunit, which is described in U.S. Pat. No. 4,962,028. Other preferred sequences for the use in functional linkage in plant gene expression cassettes are targeting sequences which are required for targeting the gene product into its relevant cell compartment (for a review, see Kermode 1996, Crit. Rev. Plant Sci. 15, 4: 285-423 and references cited therein), for example into the vacuole, the nucleus, all types of plastids, such as amyloplasts, chloroplasts, chromoplasts, the extracellular space, the mitochondria, the endoplasmic reticulum, oil bodies, peroxisomes and other compartments of plant cells. As described above, plant gene expression can also be facilitated via a chemically inducible promoter (for a review, see Gatz 1997, Annu. Rev. Plant Physiol. Plant Mol. Biol., 48:89-108). Chemically inducible promoters are particularly suitable if it is desired that genes are expressed in a time-specific manner. Examples of such promoters are a salicylic-acid-inducible promoter (WO 95/19443), a tetracyclin-inducible promoter (Gatz 1992, Plant J. 2, 397-404) and an ethanol-inducible promoter. Promoters which respond to biotic or abiotic stress conditions are also suitable promoters, for example the pathogen-induced PRP1-gene promoter (Ward 1993, Plant Mol. Biol. 22:361-366), the heat-inducible hsp80 promoter from tomato (U.S. Pat. No. 5,187,267), the cold-inducible alpha-amylase promoter from potato (WO 96/12814) or the wound-inducible pinII promoter (EP 0 375 091 A). The promoters which are especially preferred are those which bring about the expression of genes in tissues and organs in which fatty acid, lipid and oil biosynthesis takes place, in seed cells such as the cells of endosperm and of the developing embryo. Suitable promoters are the napin gene promoter from oilseed rape (U.S. Pat. No. 5,608,152), the USP promoter from *Vicia faba* (Baeumlein 1991, Mol. Gen. Genet. 225 (3):459-67), the oleosin promoter from *Arabidopsis* (WO 98/45461), the phaseolin promoter from *Phaseolus vulgaris* (U.S. Pat. No. 5,504,200), the Bce4 promoter from *Brassica* (WO 91/13980) or the legumin B4 promoter (LeB4; Baeumlein 1992, Plant Journal, 2 (2):233-9), and promoters which bring about the seed-specific expression in monocotyledonous plants such as maize, barley, wheat, rye, rice and the like. Suitable promoters to be taken into consideration are the lpt2 or lpt1 gene promoter from barley (WO 95/15389 and WO 95/23230) or those which are described in WO 99/16890 (promoters from the barley hordein gene, the rice glutelin gene, the rice oryzin gene, the rice prolamin gene, the wheat gliadin gene, wheat glutelin gene, the maize zein gene, the oat glutelin gene, the *sorghum* kasirin gene, the rye secalin gene). Likewise, especially suitable are promoters which bring about the plastid-specific expression since plastids are the compartment in which the precursors and some end products of lipid biosynthesis are synthesized. Suitable promoters such as the viral RNA-polymerase promoter, are described in WO 95/16783 and WO 97/06250, and the clpP promoter from *Arabidopsis*, described in WO 99/46394.

The abovementioned vectors are only a small overview of vectors to be used in accordance with the present invention. Further vectors are known to the skilled worker and are described, for example, in: Cloning Vectors (Ed., Pouwels, P. H., et al., Elsevier, Amsterdam-New York-Oxford, 1985, ISBN 0 444 904018). For further suitable expression systems for prokaryotic and eukaryotic cells see the chapters 16 and 17 of Sambrook, loc cit.

It follows from the above that, preferably, said vector is an expression vector. More preferably, the said polynucleotide of the present invention is under the control of a seed-specific promoter in the vector of the present invention. A preferred seed-specific promoter as meant herein is selected from the group consisting of Conlinin 1, Conlinin 2, napin, LuFad3, USP, LeB4, Arc, Fae, ACP, LuPXR, and SBP. For details, see, e.g., US 2003-0159174.

Moreover, the present invention relates to a host cell comprising the polynucleotide or the vector of the present invention.

Preferably, said host cell is a plant cell and, more preferably, a plant cell obtained from an oilseed crop. More preferably, said oilseed crop is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, camelina, *crambe*, oil palm, coconuts, groundnuts, sesame seed, castor bean, *lesquerella*, tallow tree, sheanuts, tungnuts, kapok fruit, poppy seed, jojoba seeds and *perilla*.

Also preferably, said host cell is a microorganism. More preferably, said microorganism is a bacterium, a fungus or algae. More preferably, it is selected from the group consisting of *Candida, Cryptococcus, Lipomyces, Rhodosporidium, Yarrowia*, and, *Schizochytrium*.

Moreover, a host cell according to the present invention may also be an animal cell. Preferably, said animal host cell is a host cell of a fish or a cell line obtained therefrom. More preferably, the fish host cell is from herring, salmon, sardine, redfish, eel, carp, trout, halibut, mackerel, zander or tuna.

It will be understood that if the host cell of the invention shall be applied for LCPUFA production, it shall be capable of carrying out desaturation and elongation steps on fatty acids. To produce the LCPUFA according to the invention, the C16- or C18-fatty acids must first be desaturated by the enzymatic activity of a desaturase and subsequently be elongated by at least two carbon atoms via an elongase. After one elongation cycle, this enzyme activity gives C18- or C20-fatty acids and after two or three elongation cycles C22- or C24-fatty acids. The activity of the desaturases and elongases used in the process according to the invention preferably leads to C18-, C20-, C22- and/or C24-fatty acids, advantageously with at least two double bonds in the fatty acid molecule, preferably with three, four or five double bonds, especially preferably to give C20- and/or C22-fatty acids with at least two double bonds in the fatty acid molecule, preferably with three, four or five double bonds in the molecule. After a first desaturation and the elongation have taken place, further desaturation steps such as, for example, one in the delta-5 position may take place. Products of the process according to the invention which are especially preferred are DGLA, ARA, EPA DPA and/or DHA, most preferably EPA and/or DHA. Desaturases and elongases which are required for this process may not always be present naturally in the host cell. Accordingly, the present invention, preferably, envisages a host cell which in addition to the polynucleotide of the present invention comprises polynucleotides encoding such desaturases and/or elongases as required depending on the selected organism. Preferred desaturases and/or elongases which shall be present in the host cell are at least one enzyme selected from the group consisting of: Δ-4-desaturase, Δ-5-desaturase, Δ-5-elongase, Δ-6-desaturase, Δ12-desaturase, Δ15-desaturase, ω3-desaturase and Δ-6-elongase. Especially preferred are the bifunctional d12d15-Desaturases d12d15Des(Ac) from *Acanthamoeba castellanii* (WO2007042510), d12d15Des (Cp) from *Claviceps purpurea* (WO2008006202) and d12d15Des(Lg)1 from *Lottia gigantea* (WO2009016202), the d12-Desaturases d12Des(Co) from *Calendula officinalis* (WO200185968), d12Des(Lb) from *Laccaria bicolor* (WO2009016202), d12Des(Mb) from *Monosiga brevicollis* (WO2009016202), d12Des(Mg) from *Mycosphaerella graminicola* (WO2009016202), d12Des(Nh) from *Nectria haematococca* (WO2009016202), d12Des(Ol) from *Ostreococcus lucimarinus* (WO2008040787), d12Des(Pb) from *Phycomyces blakesleeanus* (WO2009016202), d12Des(Ps) from *Phytophthora sojae* (WO2006100241) and d12Des (Tp) from *Thalassiosira pseudonana* (WO2006069710), the d15-Desaturases d15Des(Hr) from *Helobdella robusta* (WO2009016202), d15Des(Mc) from *Microcoleus chthonoplastes* (WO2009016202), d15Des(Mf) from *Mycosphaerella fijiensis* (WO2009016202), d15Des(Mg) from *Mycosphaerella graminicola* (WO2009016202) and d15Des (Nh)2 from *Nectria haematococca* (WO2009016202), the d4-Desaturases d4Des(Eg) from *Euglena gracilis* (WO2004090123), d4Des(Tc) from *Thraustochytrium* sp. (WO2002026946) and d4Des(Tp) from *Thalassiosira pseudonana* (WO2006069710), the d5-Desaturases d5Des (Ol)2 from *Ostreococcus lucimarinus* (WO2008040787), d5Des(Pp) from *Physcomitrella patens* (WO2004057001), d5Des(Pt) from *Phaeodactylum tricornutum* (WO2002057465), d5Des(Tc) from *Thraustochytrium* sp. (WO2002026946), d5Des(Tp) from *Thalassiosira pseudonana* (WO2006069710) and the d6-Desaturases d6Des(Cp) from *Ceratodon purpureus* (WO2000075341), d6Des(Ol)

from *Ostreococcus lucimarinus* (WO2008040787), d6Des (Ot) from *Ostreococcus tauri* (WO2006069710), d6Des(Pf) from *Primula farinosa* (WO2003072784), d6Des(Pir)_BO from *Pythium irregulare* (WO2002026946), d6Des(Pir) from *Pythium irregulare* (WO2002026946), d6Des(Plu) from *Primula luteola* (WO2003072784), d6Des(Pp) from *Physcomitrella patens* (WO200102591), d6Des(Pt) from *Phaeodactylum tricornutum* (WO2002057465), d6Des(Pv) from *Primula vialii* (WO2003072784) and d6Des(Tp) from *Thalassiosira pseudonana* (WO2006069710), the d8-Desaturases d8Des(Ac) from *Acanthamoeba castellanii* (EP1790731), d8Des(Eg) from *Euglena gracilis* (WO200034439) and d8Des(Pm) from *Perkinsus marinus* (WO2007093776), the o3-Desaturases o3Des(Pi) from *Phytophthora infestans* (WO2005083053), o3Des(Pir) from *Pythium irregulare* (WO2008022963), o3Des(Pir)2 from *Pythium irregulare* (WO2008022963) and o3Des(Ps) from *Phytophthora sojae* (WO2006100241), the bifunctional d5d6-elongases d5d6Elo(Om)2 from *Oncorhynchus mykiss* (WO2005012316), d5d6Elo(Ta) from *Thraustochytrium aureum* (WO2005012316) and d5d6Elo(Tc) from *Thraustochytrium* sp. (WO2005012316), the d5-elongases d5Elo (At) from *Arabidopsis thaliana* (WO2005012316), d5Elo (At)2 from *Arabidopsis thaliana* (WO2005012316), d5Elo (Ci) from *Ciona intestinalis* (WO2005012316), d5Elo(Ol) from *Ostreococcus lucimarinus* (WO2008040787), d5Elo (Ot) from *Ostreococcus tauri* (WO2005012316), d5Elo(Tp) from *Thalassiosira pseudonana* (WO2005012316) and d5Elo(Xl) from *Xenopus laevis* (WO2005012316), the d6-elongases d6Elo(Ol) from *Ostreococcus lucimarinus* (WO2008040787), d6Elo(Ot) from *Ostreococcus tauri* (WO2005012316), d6Elo(Pi) from *Phytophthora infestans* (WO2003064638), d6Elo(Pir) from *Pythium irregulare* (WO2009016208), d6Elo(Pp) from *Physcomitrella patens* (WO2001059128), d6Elo(Ps) from *Phytophthora sojae* (WO2006100241), d6Elo(Ps)2 from *Phytophthora sojae* (WO2006100241), d6Elo(Ps)3 from *Phytophthora sojae* (WO2006100241), d6Elo(Pt) from *Phaeodactylum tricornutum* (WO2005012316), d6Elo(Tc) from *Thraustochytrium* sp. (WO2005012316) and d6Elo(Tp) from *Thalassiosira pseudonana* (WO2005012316), the d9-elongases d9Elo (Ig) from *Isochrysis galbana* (WO2002077213), d9Elo(Pm) from *Perkinsus marinus* (WO2007093776) and d9Elo(Ro) from *Rhizopus oryzae* (WO2009016208).

The present invention also relates to a cell, preferably a host cell as specified above or a cell of a non-human organism specified elsewhere herein, said cell comprising a polynucleotide which is obtained from the polynucleotide of the present invention by a point mutation, a truncation, an inversion, a deletion, an addition, a substitution and homologous recombination. How to carry out such modifications to a polynucleotide is well known to the skilled artisan and has been described elsewhere in this specification in detail.

The present invention furthermore pertains to a method for the manufacture of a polypeptide encoded by a polynucleotide of any the present invention comprising a) cultivating the host cell of the invention under conditions which allow for the production of the said polypeptide; and b) obtaining the polypeptide from the host cell of step a).

Suitable conditions which allow for expression of the polynucleotide of the invention comprised by the host cell depend on the host cell as well as the expression control sequence used for governing expression of the said polynucleotide. These conditions and how to select them are very well known to those skilled in the art. The expressed polypeptide may be obtained, for example, by all conventional purification techniques including affinity chromatography, size exclusion chromatography, high pressure liquid chromatography (HPLC) and precipitation techniques including antibody precipitation. It is to be understood that the method may—although preferred—not necessarily yield an essentially pure preparation of the polypeptide. It is to be understood that depending on the host cell which is used for the aforementioned method, the polypeptides produced thereby may become posttranslationally modified or processed otherwise.

The present invention encompasses a polypeptide encoded by the polynucleotide of the present invention or which is obtainable by the aforementioned method.

The term "polypeptide" as used herein encompasses essentially purified polypeptides or polypeptide preparations comprising other proteins in addition. Further, the term also relates to the fusion proteins or polypeptide fragments being at least partially encoded by the polynucleotide of the present invention referred to above. Moreover, it includes chemically modified polypeptides. Such modifications may be artificial modifications or naturally occurring modifications such as phosphorylation, glycosylation, myristylation and the like (Review in Mann 2003, Nat. Biotechnol. 21, 255-261, review with focus on plants in Huber 2004, Curr. Opin. Plant Biol. 7, 318-322). Currently, more than 300 posttranslational modifications are known (see full ABFRC Delta mass list at abrf.org/index.cfm/dm.home). The polypeptide of the present invention shall exhibit the acyltransferase activities referred to above.

Encompassed by the present invention is, furthermore, an antibody which specifically recognizes the polypeptide of the invention.

Antibodies against the polypeptides of the invention can be prepared by well known methods using a purified polypeptide according to the invention or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. Preferably, the antibody of the present invention is a monoclonal antibody, a polyclonal antibody, a single chain antibody, a chimerized antibody or a fragment of any of these antibodies, such as Fab, Fv or scFv fragments etc. Also comprised as antibodies by the present invention are bispecific antibodies, synthetic antibodies or chemically modified derivatives of any of the aforementioned antibodies. The antibody of the present invention shall specifically bind (i.e. does significantly not cross react with other polypeptides or peptides) to the polypeptide of the invention. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler 1975, Nature 256, 495, and Galfré 1981, Meth. Enzymol. 73, 3, which comprise the fusion of mouse myeloma cells to spleen cells derived from immunized mammals. The antibodies can be used, for example, for the immunoprecipitation, immunolocalization or purification (e.g., by affinity chromatography) of the polypeptides of the invention as well as for the monitoring of the presence of said variant polypeptides, for example, in recombinant organisms, and for the identification of proteins or compounds interacting with the proteins according to the invention.

Moreover, the present invention contemplates a non-human transgenic organism comprising the polynucleotide or the vector of the present invention.

Preferably, the non-human transgenic organism is a plant, plant part, or plant seed. Preferred plants to be used for introducing the polynucleotide or the vector of the invention are plants which are capable of synthesizing fatty acids, such as all dicotyledonous or monocotyledonous plants, algae or mosses. It is to be understood that host cells derived from a plant may also be used for producing a plant according to the present invention. Preferred plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as *Tagetes*. Examples which may be mentioned are the following plants selected from the group consisting of: Adelotheciaceae such as the genera *Physcomitrella*, such as the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae such as the genera *Amphora, Cymbella, Okedenia, Phaeodactylum, Reimeria*, for example the genus and species *Phaeodactylum tricornutum*, Ditrichaceae such as the genera *Ditrichaceae, Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpureus, Ceratodon purpureus, Ceratodon purpureus* ssp. *convolutus, Ceratodon, purpureus* spp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae such as the genus *Elaeagnus*, for example the genus and species *Olea europaea* [olive], Ericaceae such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta [manihot*] or *Ricinus communis* [castor-oil plant], Fabaceae such as the genera *Pisum, Albizia, Cathormion, Feuillea, Inga, Pithecolobium, Acacia, Mimosa, Medicajo, Glycine, Dolichos, Phaseolus, Soja*, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [silk tree], *Medicago sativa, Medicago falcata, Medicago varia* [alfalfa], *Glycine max Dolichos soja, Glycine gracilis, Glycine hispida, Phaseolus max, Soja hispida* or *Soja max* [soybean], Funariaceae such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria ameri-*

*cana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Linum, Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea, Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elacis*, for example the genus and species *Elaeis guineensis* [oil palm], Papaveraceae, such as the genus *Papaver*, for example the genera and species *Papaver orientale, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize], *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia*, for example the genus and species *Porphyridium cruentum*, Proteaceae, such as the genus *Macadamia*, for example the genus and species *Macadamia intergrifolia [macadamia*], Prasinophyceae such as the genera *Nephroselmis, Prasinococcus, Scherffelia, Tetraselmis, Mantoniella, Ostreococcus*, for example the genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae such as the genus *Cofea*, for example the genera and species *Cofea* spp., *Coffea arabica, Coffea canephora* or *Coffea liberica* [coffee], Scrophulariaceae such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [mullein], Solanaceae such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea]. In particular preferred plants to be used as transgenic plants in accordance with the present invention are oil fruit crops which comprise large amounts of lipid compounds, such as peanut, oilseed rape, canola, sunflower, safflower, poppy, mustard, hemp, castor-oil plant, olive, sesame, *Calendula, Punica*, evening primrose, mullein, thistle, wild roses, hazelnut, almond, *macadamia*, avocado, bay, pumpkin/squash, linseed, soybean, pistachios, borage, trees (oil palm, coconut, walnut) or crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are sunflower, safflower, tobacco, mullein, sesame, cotton, pumpkin/squash, poppy, evening primrose, walnut, linseed, hemp, thistle or safflower. Very especially preferred plants are plants such as safflower, sunflower, poppy, evening primrose, walnut, linseed, or hemp.

Preferred mosses are *Physcomitrella* or *Ceratodon*. Preferred algae are *Isochrysis, Mantoniella, Ostreococcus* or *Crypthecodinium*, and algae/diatoms such as *Phaeodactylum* or *Thraustochytrium*. More preferably, said algae or mosses are selected from the group consisting of: *Shewanella, Physcomitrella, Thraustochytrium, Fusarium, Phytophthora, Ceratodon, Isochrysis, Aleurita, Muscarioides, Mortierella, Phaeodactylum, Cryphthecodinium*, specifically from the genera and species *Thallasiosira pseudonona, Euglena gracilis, Physcomitrella patens, Phytophtora infestans, Fusarium graminaeum, Cryptocodinium cohnii, Ceratodon purpureus, Isochrysis galbana, Aleurita farinosa, Thraustochytrium* sp., *Muscarioides viallii, Mortierella alpina, Phaeodactylum tricomutum* or *Caenorhabditis elegans* or especially advantageously *Phytophtora infestans, Thallasiosira pseudonona* and *Cryptocodinium cohnii.*

Transgenic plants may be obtained by transformation techniques as elsewhere in this specification. Preferably, transgenic plants can be obtained by T-DNA-mediated transformation. Such vector systems are, as a rule, characterized in that they contain at least the vir genes, which are required for the *Agrobacterium*-mediated transformation, and the sequences which delimit the T-DNA (T-DNA border). Suitable vectors are described elsewhere in the specification in detail.

Also encompassed are transgenic non-human animals comprising the vector or polynucleotide of the present invention. Preferred non-human transgenic animals envisaged by the present invention are fish, such as herring, salmon, sardine, redfish, eel, carp, trout, halibut, mackerel, zander or tuna.

It will be understood that in order to produce the LCPUFA according to the invention, the C16- or C18-fatty acids must first be desaturated by the enzymatic activity of a desaturase and subsequently be elongated by at least two carbon atoms via an elongase in the non-human transgenic organism. After one elongation cycle, this enzyme activity gives C18- or C20-fatty acids and after two or three elongation cycles C22- or C24-fatty acids. The activity of the desaturases and elongases used in the process according to the invention preferably leads to C18-, C20-, C22- and/or C24-fatty acids, advantageously with at least two double bonds in the fatty acid molecule, preferably with three, four or five double bonds, especially preferably to give C20- and/or C22-fatty acids with at least two double bonds in the fatty acid molecule, preferably with three, four or five double bonds in the molecule. After a first desaturation and the elongation have taken place, further desaturation steps such as, for example, one in the delta-5 position may take place. Products of the process according to the invention which are especially preferred are DGLA, ARA, EPA DPA and/or DHA, most preferably EPA and/or DHA. Desaturases and elongases which are required for this process may not always be present naturally in the organism. Accordingly, the present invention, preferably, envisages a transgenic non-human organism which in addition to the polynucleotide of the present invention comprises polynucleotides encoding such desaturases and/or elongases as required depending on the selected organism. Preferred desaturases and/or elongases which shall be present in the organism are at least one enzyme selected from the group consisting of: Δ-4-desaturase, Δ-5-desaturase, elongase, Δ-6-desaturase, Δ12-desaturase, Δ15-desaturase, ω3-desaturase and Δ-6-elongase. Especially preferred are the bifunctional d12d15-Desaturases d12d15Des(Ac) from *Acanthamoeba castellanii* (WO2007042510), d12d15Des(Cp) from *Claviceps purpurea* (WO2008006202) and d12d15Des(Lg)1 from *Lottia gigantea* (WO2009016202), the d12-Desaturases d12Des(Co) from *Calendula officinalis* (WO200185968), d12Des(Lb) from *Laccaria bicolor* (WO2009016202), d12Des(Mb) from *Monosiga brevicollis* (WO2009016202), d12Des(Mg) from *Mycosphaerella graminicola* (WO2009016202), d12Des(Nh) from *Nectria haematococca* (WO2009016202), d12Des(Ol) from *Ostreococcus lucimarinus* (WO2008040787), d12Des(Pb) from *Phycomyces blakesleeanus* (WO2009016202), dl 2Des(Ps) from *Phytophthora sojae* (WO2006100241) and d12Des(Tp) from *Thalassiosira pseudonana* (WO2006069710), the d15-Desaturases d15Des(Hr) from *Helobdella robusta* (WO2009016202), d15Des(Mc) from *Microcoleus chthonoplastes* (WO2009016202), dl 5Des(Mf) from *Mycosphaerella fijiensis* (WO2009016202), d15Des(Mg) from *Mycosphaerella graminicola* (WO2009016202) and d15Des (Nh)2 from *Nectria haematococca* (WO2009016202), the d4-Desaturases d4Des(Eg) from *Euglena gracilis* (WO2004090123), d4Des(Tc) from *Thraustochytrium* sp. (WO2002026946) and d4Des(Tp) from *Thalassiosira pseudonana* (WO2006069710), the d5-Desaturases d5Des (Ol)2 from *Ostreococcus lucimarinus* (WO2008040787), d5Des(Pp) from *Physcomitrella patens* (WO2004057001), d5Des(Pt) from *Phaeodactylum tricornutum* (WO2002057465), d5Des(Tc) from *Thraustochytrium* sp. (WO2002026946), d5Des(Tp) from *Thalassiosira pseudonana* (WO2006069710) and the d6-Desaturases d6Des(Cp) from *Ceratodon purpureus* (WO2000075341), d6Des(Ol) from *Ostreococcus lucimarinus* (WO2008040787), d6Des (Ot) from *Ostreococcus tauri* (WO2006069710), d6Des(Pf) from *Primula farinosa* (WO2003072784), d6Des(Pir)_BO from *Pythium* irregulare (WO2002026946), d6Des(Pir) from *Pythium irregulare* (WO2002026946), d6Des(Plu) from *Primula luteola* (WO2003072784), d6Des(Pp) from *Physcomitrella patens* (WO200102591), d6Des(Pt) from *Phaeodactylum tricornutum* (WO2002057465), d6Des(Pv) from *Primula vialii* (WO2003072784) and d6Des(Tp) from *Thalassiosira pseudonana* (WO2006069710), the d8-Desaturases d8Des(Ac) from *Acanthamoeba castellanii* (EP1790731), d8Des(Eg) from *Euglena gracilis* (WO200034439) and d8Des(Pm) from *Perkinsus marinus* (WO2007093776), the o3-Desaturases o3Des(Pi) from *Phytophthora infestans* (WO2005083053), o3Des(Pir) from *Pythium irregulare* (WO2008022963), o3Des(Pir)2 from *Pythium irregulare* (WO2008022963) and o3Des(Ps) from *Phytophthora sojae* (WO2006100241), the bifunctional d5d6-elongases d5d6Elo(Om)2 from *Oncorhynchus mykiss* (WO2005012316), d5d6Elo(Ta) from *Thraustochytrium aureum* (WO2005012316) and d5d6Elo(Tc) from *Thraustochytrium* sp. (WO2005012316), the d5-elongases d5Elo (At) from *Arabidopsis thaliana* (WO2005012316), d5Elo (At)2 from *Arabidopsis thaliana* (WO2005012316), d5Elo (Ci) from Ciona *intestinalis* (WO2005012316), d5Elo(Ol) from *Ostreococcus lucimarinus* (WO2008040787), d5Elo (Ot) from *Ostreococcus tauri* (WO2005012316), d5Elo(Tp) from *Thalassiosira pseudonana* (WO2005012316) and d5Elo(Xl) from *Xenopus laevis* (WO2005012316), the d6-elongases d6Elo(Ol) from *Ostreococcus lucimarinus* (WO2008040787), d6Elo(Ot) from *Ostreococcus tauri* (WO2005012316), d6Elo(Pi) from *Phytophthora infestans* (WO2003064638), d6Elo(Pir) from *Pythium irregulare* (WO2009016208), d6Elo(Pp) from *Physcomitrella patens* (WO2001059128), d6Elo(Ps) from *Phytophthora sojae* (WO2006100241), d6Elo(Ps)2 from *Phytophthora sojae* (WO2006100241), d6Elo(Ps)3 from *Phytophthora sojae* (WO2006100241), d6Elo(Pt) from *Phaeodactylum tricornutum* (WO2005012316), d6Elo(Tc) from *Thraustochytrium* sp. (WO2005012316) and d6Elo(Tp) from *Thalassiosira pseudonana* (WO2005012316), the d9-elongases d9Elo (Ig) from *Isochrysis galbana* (WO2002077213), d9Elo(Pm) from *Perkinsus marinus* (WO2007093776) and d9Elo(Ro) from *Rhizopus oryzae* (WO2009016208).

Furthermore, the present invention encompasses a method for the manufacture of polyunsaturated fatty acids comprising:

a) cultivating the host cell of the invention under conditions which allow for the production of polyunsaturated fatty acids in said host cell; and
b) obtaining said polyunsaturated fatty acids from the said host cell.

The term "polyunsaturated fatty acids (PUFA)" as used herein refers to fatty acids comprising at least two, preferably, three, four, five or six, double bonds. Moreover, it is to be understood that such fatty acids comprise, preferably from 18 to 24 carbon atoms in the fatty acid chain. More preferably, the term relates to long chain PUFA (LCPUFA) having from 20 to 24 carbon atoms in the fatty acid chain. Preferred unsaturated fatty acids in the sense of the present invention are selected from the group consisting of arachidonic acid (ARA) 20:4 (5,8,11,14), eicosapentaenoic acid (EPA) 20:5 (5,8,11,14,17), and docosahexaenoic acid (DHA) 22:6 (4,7,10,13,16,19) and, more preferably, from EPA and DHA. Thus, it will be understood that most preferably, the methods provided by the present invention pertaining to the manufacture of EPA or DHA. Moreover, also encompassed are the intermediates of LCPUFA which occur during synthesis starting from oleic acid 18:1 (9), preferably, linoleic acid 18:2 (9,12), alpha-linolenic acid 18:3 (9,12,15), gamma-linolenic acid 18:3 (6,9,12), stearidonic acid 18:4 (6,9,12,15), dihomo-gamma-linoleic acid 20:3 (8,11,14), eicosadienoic acid 20:2 (11,14), eicosatrienoic acid 20:3 (11,14,17), eicosatetraenoic acid 20:4 (8,11,14,17) and docospentaenoic acid (DPA) 22:5 (4,7,10,13,16).

The term "cultivating" as used herein refers maintaining and growing the host cells under culture conditions which allow the cells to produce the said polyunsaturated fatty acid, i.e. the PUFA and/or LCPUFA referred to above, preferably, as triglyceride esters. This implies that the polynucleotide of the present invention is expressed in the host cell so that the acyltransferase activity is present. Suitable culture conditions for cultivating the host cell are described in more detail below.

The term "obtaining" as used herein encompasses the provision of the cell culture including the host cells and the culture medium as well as the provision of purified or partially purified preparations thereof comprising the polyunsaturated fatty acids, preferably, as triglyceride esters. More preferably, the PUFA and LCPUFA are to be obtained as triglyceride esters, e.g., in form of an oil. More details on purification techniques can be found elsewhere herein below.

The host cells to be used in the method of the invention are grown or cultured in the manner with which the skilled worker is familiar, depending on the host organism. Usually, host cells are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C. under oxygen or anaerobic atmosphere depedent on the type of organism. The pH of the liquid medium can either be kept constant, that is to say regulated during the culturing period, or not. The cultures can be grown batchwise, semibatchwise or continuously. Nutrients can be provided at the beginning of the fermentation or administerd semicontinuously or continuously: The produced PUFA or LCPUFA can be isolated from the host cells as described above by processes known to the skilled worker, e.g., by extraction, distillation, crystallization, if appropriate precipitation with salt, and/or chromatography. It might be required to disrupt the host cells prior to purification. To this end, the host cells can be disrupted beforehand. The culture medium to be used must suitably meet the requirements of the host cells in question. Descriptions of culture media for various microorganisms which can be used as host cells according to the present invention can be found in the textbook "Manual of Methods for General Bacteriology" of the American Society for Bacteriology (Washington D.C., USA, 1981). Culture media can also be obtained from various commercial suppliers. All media components are sterilized, either by heat or by filter sterilization. All media components may be present at the start of the cultivation or added continuously or batchwise, as desired. If the polynucleotide or vector of the invention which has been introduced in the host cell further comprises an expressible selection marker, such as an antibiotic resistance gene, it might be necessary to add a selection agent to the culture, such as a antibiotic in order to maintain the stability of the introduced polynucleotide. The culture is continued until formation of the desired product is at a maximum. This is normally achieved within 10 to 160 hours. The fermentation broths can be used directly or can be processed further. The biomass may, according to requirement, be removed completely or partially from the fermentation broth by separation methods such as, for example, centrifugation, filtration, decanting or a combination of these methods or be left completely in said broth. The fatty acid preparations obtained by the method of the invention, e.g., oils, comprising the desired PUFA or LCPUFA as triglyceride esters are also suitable as starting material for the chemical synthesis of further products of interest. For example, they can be used in combination with one another or alone for the preparation of pharmaceutical or cosmetic compositions, foodstuffs, or animal feeds. Chemically pure triglycerides comprising the desired PUFA or LCPUFA can also be manufactured by the methods described above. To this end, the fatty acid preparations are further purified by extraction, distillation, crystallization, chromatography or combinations of these methods. In order to release the fatty acid moieties from the triglycerides, hydrolysis may be also required. The said chemically pure triglycerides or free fatty acids are, in particular, suitable for applications in the food industry or for cosmetic and pharmacological compositions.

Moreover, the present invention relates to a method for the manufacture of polyunsaturated fatty acids comprising:

a) cultivating the non-human transgenic organism of the invention under conditions which allow for the production of poly-unsaturated fatty acids in said host cell; and b) obtaining said poly-unsaturated fatty acids from the said non-human transgenic organism.

Further, it follows from the above that a method for the manufacture of an oil, lipid or fatty acid composition is also envisaged by the present invention comprising the steps of any one of the aforementioned methods and the further step of formulating PUFA or LCPUFA as oil, lipid or fatty acid composition. Preferably, said oil, lipid or fatty acid composition is to be used for feed, foodstuffs, cosmetics or medicaments. Accordingly, the formulation of the PUFA or LCPUFA shall be carried out according to the GMP standards for the individual envisaged products. For example, an oil may be obtained from plant seeds by an oil mill. However, for product safety reasons, sterilization may be required under the applicable GMP standard. Similar standards will apply for lipid or fatty acid compositions to be applied in cosmetic or pharmaceutical compositions. All these measures for formulating oil, lipid or fatty acid compositions as products are comprised by the aforementioned manufacture.

The present invention also relates to an oil comprising a polyunsaturated fatty acid obtainable by the aforementioned methods.

The term "oil" refers to a fatty acid mixture comprising unsaturated and/or saturated fatty acids which are esterified to triglycerides. Preferably, the triglycerides in the oil of the invention comprise PUFA or LCPUFA as referred to above. The amount of esterified PUFA and/or LCPUFA is, preferably, approximately 30%, a content of 50% is more preferred, a content of 60%, 70%, 80% or more is even more preferred. The oil may further comprise free fatty acids, preferably, the PUFA and LCPUFA referred to above. For the analysis, the fatty acid content can be, e.g., determined by GC analysis after converting the fatty acids into the methyl esters by transesterification. The content of the various fatty acids in the oil or fat can vary, in particular depending on the source. The oil, however, shall have a non-naturally occurring composition with respect to the PUFA and/or LCPUFA composition and content. It will be understood that such a unique oil composition and the unique esterification pattern of PUFA and LCPUFA in the triglycerides of the oil shall only be obtainable by applying the methods of the present invention specified above. Moreover, the oil of the invention may comprise other molecular species as well. Specifically, it may comprise minor impurities of the polynucleotide or vector of the invention. Such impurities, however, can be detected only by highly sensitive techniques such as PCR.

The contents of all references cited throughout this application are herewith incorporated by reference in general and with respect to their specific disclosure content referred to above.

FIGURES

FIG. 1: LPAAT activity assay.

A yeast mutant lacking LPAAT activity (due to knockout of the gene YDL052c) was transformed with the empty vector pYES2.1 (lane marked "–") and with pYES2.1 harboring the cDNA of pLPLAT_01332 (Pi) (lane 1, SEQ-ID: 1), pLPLAT_01330 (Pi) (lane 2, SEQ-ID: 3), pLPLAT_07077 Pi) (lane 3, SEQ-ID: 5), LPLAT_18374 (Pi) (lane 4, SEQ-ID: 7), pLPLAT_14816 (Pi) (lane 5, SEQ-ID: 9), LPAAT_13842 (Pi) (lane 6, SEQ-ID: 11), pLPAAT_10763 (Pi) (lane 7, SEQ-ID: 13), LPCAT_02075 (Pi) (lane 8, SEQ-ID: 15), pLPAAT_06638 (Pi) (lane 9, SEQ-ID: 17). Microsomal isolations of these transformants and the wildtype yeast strain BY4742 (lane marked "+") where incubated with $^{14}C$-labeled oleic acid and lysophosphatidic acid (LPA). Thin layer chromatography was performed to separate lipid classes. Like for wildtype yeast (lane marked "+"), phosphatidic acid (PA) is observed in lane 4 and 6, indicating the candidates LPLAT_18374 (Pi) and LPAAT_13842 (Pi) have LPAAT activity and complement the missing LPAAT activity of the knockout strain.

Figure 2:
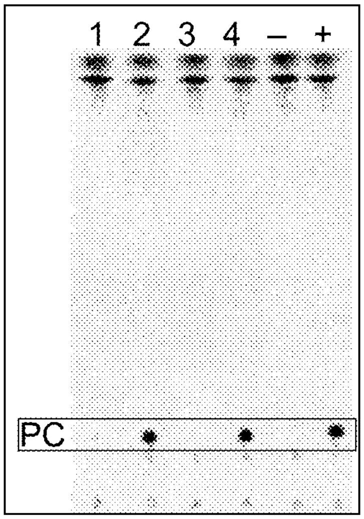
FIG. 2: LPEAT activity assay.

FIG. 2: LPEAT activity assay.

A yeast mutant lacking LPEAT and LPCAT activity (due to knockout of the gene YOR175c) was transformed with the empty vector pYES2.1 (lane marked "–") and with pYES2.1 harboring the cDNA of pLPLAT_01330 (Pi) (lane 1, SEQ-ID: 3), LPLAT_18374 (Pi) (lane 2, SEQ-ID: 7), pLPAAT_10763 (Pi) (lane 3, SEQ-ID: 13), LPCAT_02075 (Pi) (lane 4, SEQ-ID: 15). Microsomal isolations of these transformants and the wildtype yeast strain BY4742 (lane marked "+") where incubated with $^{14}C$-labeled oleic acid and lysophosphatidylethanolamine (LPE). Thin layer chromatography was performed to separate lipid classes. Like for wildtype yeast (lane marked "+"), phosphatidylethanolamine (PE) is observed in lane 2 and 4, indicating the candidates LPLAT_18374 (Pi) and LPCAT_02075 (Pi) have LPEAT activity and complement the missing LPEAT activity of the knockout strain.

Figure 3:
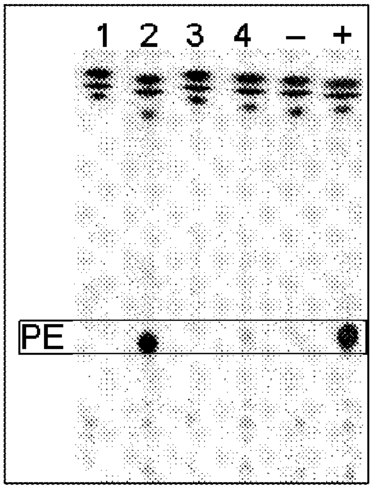
FIG. 3: LPCAT activity assay.

FIG. 3: LPCAT activity assay.

A yeast mutant lacking LPEAT and LPCAT activity (due to knockout of the gene YOR175c) was transformed with the empty vector pYES2.1 (lane marked "–") and with pYES2.1 harboring the cDNA of pLPLAT_01330 (Pi) (lane 1, SEQ-ID: 3), LPLAT_18374 (Pi) (lane 2, SEQ-ID: 7), pLPAAT_10763 (Pi) (lane 3, SEQ-ID: 13), LPCAT_02075 (Pi) (lane 4, SEQ-ID: 15). Microsomal isolations of these transformants and the wildtype yeast strain BY4742 (lane marked "+") where incubated with $^{14}C$-labeled oleic acid and lysophosphatidylcholine (LPC). Thin layer chromatography was performed to separate lipid classes. Like for wildtype yeast (lane marked "+"), phosphatidylcholine (PC) is observed in lane 2, indicating the candidate LPLAT_18374 (Pi) has LPCAT activity and complements the missing LPCAT activity of the knockout strain.

Figure 4:
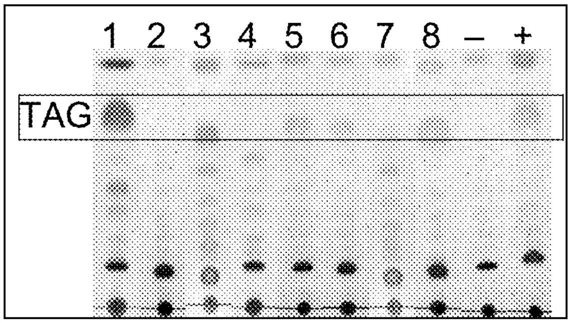
FIG. 4: DGAT activity assay.

FIG. 4: DGAT activity assay.

A yeast mutant lacking the capability to synthesis TAG (due to knockout of the four genes YCR048W, YNR019W, YOR245C and YNR008W) was transformed with the empty vector pYES2.1 (lane marked "–") and with pYES2.1 harboring the cDNA of DGAT2_03074 (Pi) (lane 1, SEQ-ID 21), pDGAT2_08467 (Pi) (lane 2, SEQ-ID 23), DGAT2_08470 (Pi) (lane 3, SEQ-ID 25), pDGAT2_03835-mod(Pi) (lane 4, SEQ-ID 27), DGAT2_11677-mod(Pi) (lane 5, SEQ-ID 29), DGAT2_08432-mod(Pi) (lane 6, SEQ-ID 31), pDGAT2_08431 (Pi) (lane 7, SEQ-ID 33) and DGAT2_13152-mod(Pi) (lane 8, SEQ-ID 35). Microsomal isolations of these transformants and the wildtype yeast strain G175 (lane marked "+") where incubated with $^{14}C$-labeled oleic acid and diacylglyerole (DAG). Thin layer chromatography was performed to separate lipid classes. Like for wildtype yeast (lane marked "+"), triacylglycerole (TAG) is observed in lane 1, 3, 5, 6 and 8, indicating the candidate DGAT2_03074 (Pi), DGAT2_08470 (Pi) DGAT2_11677-mod(Pi), DGAT2_08432-mod(Pi) and DGAT2_13152 (Pi) have DGAt activity and complement the missing TAG-synthesis capability of the knockout.

Figure 5:
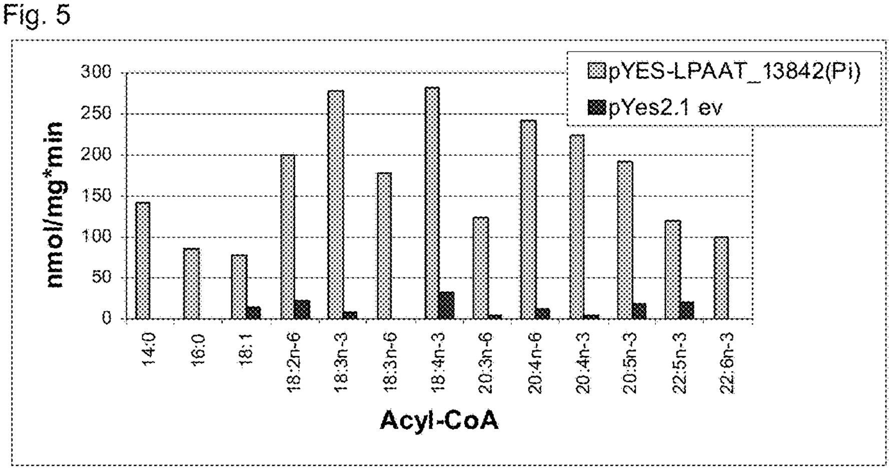
FIG. 5: Substrate specificity of LPAAT_13842 (Pi).

FIG. 5: Substrate specificity of LPAAT_13842 (Pi).

The specific activity of the enzyme LPAAT_13842 (Pi) using the substrates indicated at the x-axis is gives as the amount (in nmol) of substrate/product consumed/produced in one minute per mg total protein and was determined as described in example 5. The specific activities measured for microsomal extracts of yeast harboring an empty vector (pYES2.1 ev) is shown as control.

Figure 6:
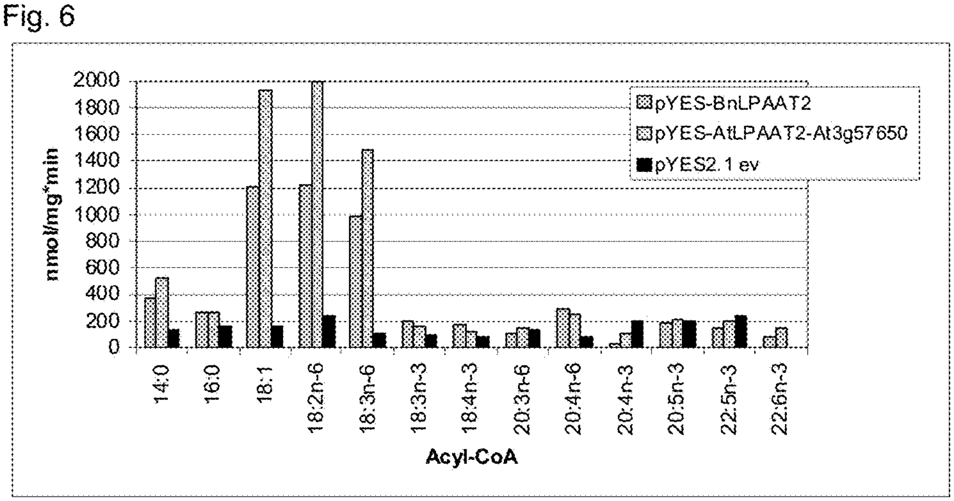
FIG. 6: Substrate specificity of AtLPAAT2-At3g57650 (SEQ-ID 86, encoded by SEQ-ID 85) and BnLPAAT2 (SEQ-ID 88, encoded by SEQ-ID 87).

FIG. 6: Substrate specificity of AtLPAAT2-At3g57650 (SEQ-ID 86, encoded by SEQ-ID 85) and BnLPAAT2 (SEQ-ID 88, encoded by SEQ-ID 87).

The specific activity of the enzymes BnLPAAT2 and AtLPAAT2-At3g57650 using the substrates indicated at the x-axis is gives as the amount (in nmol) of substrate/product consumed/produced in one minute per mg total protein and was determined as described in example 5. The specific activities measured for microsomal extracts of yeast harboring an empty vector (pYES2 ev) is shown as control.

Figure 7:
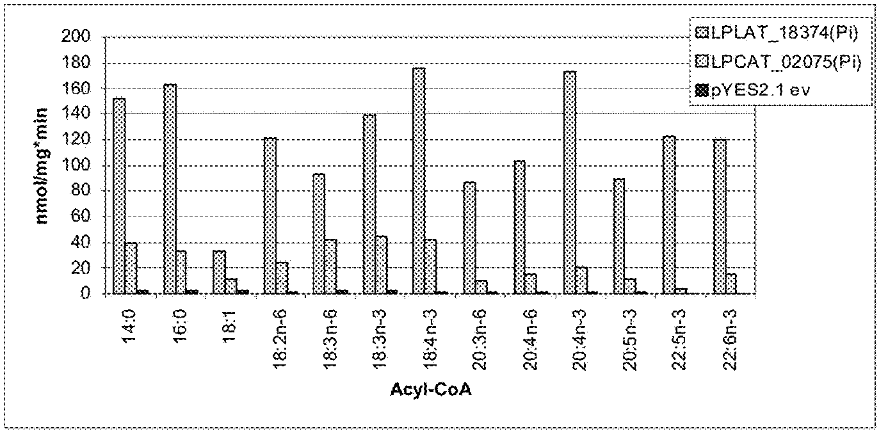
FIG. 7: Substrate specificity of LPLAT_18374 (Pi) and LPCAT_02075 (Pi) using lysophosphatidylcholine as acyl-aceptor.

FIG. 7: Substrate specificity of LPLAT_18374 (Pi) and LPCAT_02075 (Pi) using Lysophosphatidylcholine as acyl-aceptor.

The specific activity of the enzymes LPLAT_18374 (Pi) and LPCAT_02075 (Pi) using the substrates indicated at the x-axis is gives as the amount (in nmol) of substrate/product consumed/produced in one minute per mg total protein and was determined as described in example 6. The specific activities measured for microsomal extracts of yeast harboring an empty vector (pYES2 ev) is shown as control.

Figure 8:
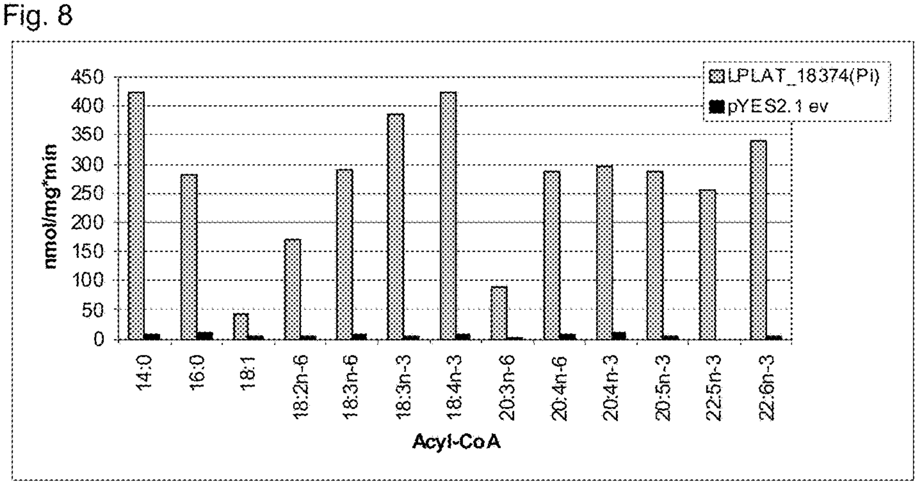
FIG. 8: Substrate specificity of LPLAT_18374 (Pi) using lysophosphatidylethanolamine as acyl-acceptor.

FIG. 8: Substrate specificity of LPLAT_18374 (Pi) using lysophosphatidylethanolamine as acyl-aceptor.

The specific activity of the enzymes LPLAT_18374 (Pi) using the substrates indicated at the x-axis is gives as the amount (in nmol) of substrate/product consumed/produced in one minute per mg total protein and was determined as described in example 6. The specific activities measured for microsomal extracts of yeast harboring an empty vector (pYES2 ev) is shown as control.

Figure 9:
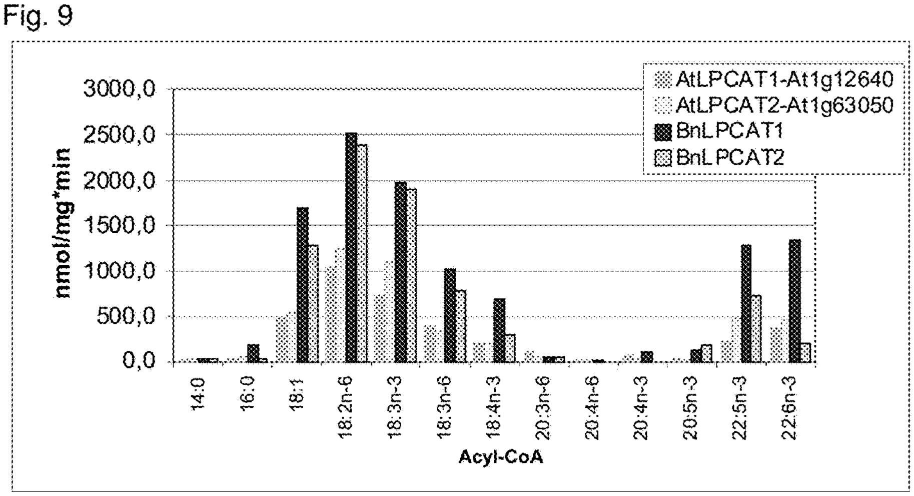
FIG. 9: Substrate specificity of AtLPCAT1-At1g12640, AtLPCAT2-At1g63050, BnLPCAT1 and BnLPCAT2 using lysophosphatidylcholine as acyl-acceptor.

FIG. 9: Substrate specificity of AtLPCAT1-At1g12640 (SEQ-ID 90, encoded by SEQ-ID 89), AtLPCAT2-At1g63050 (SEQ-ID 92, encoded by SEQ-ID 91), BnLPCAT1 (SEQ-ID 94, encoded by SEQ-ID 93) and BnLPCAT2 (SEQ-ID 96, encoded by SEQ-ID 95) using lysophosphatidylcholine as acyl-aceptor.

The specific activity of the enzymes AtLPCAT1-At1g12640, AtLPCAT2-At1g63050, BnLPCAT1 and BnLPCAT2 using the substrates indicated at the x-axis is gives as the amount (in nmol) of substrate/product consumed/produced in one minute per mg total protein and was determined as described in example 6. The specific activities measured for microsomal extracts of yeast harboring an empty vector (pYES2 ev) is shown as control.

Figure 10:
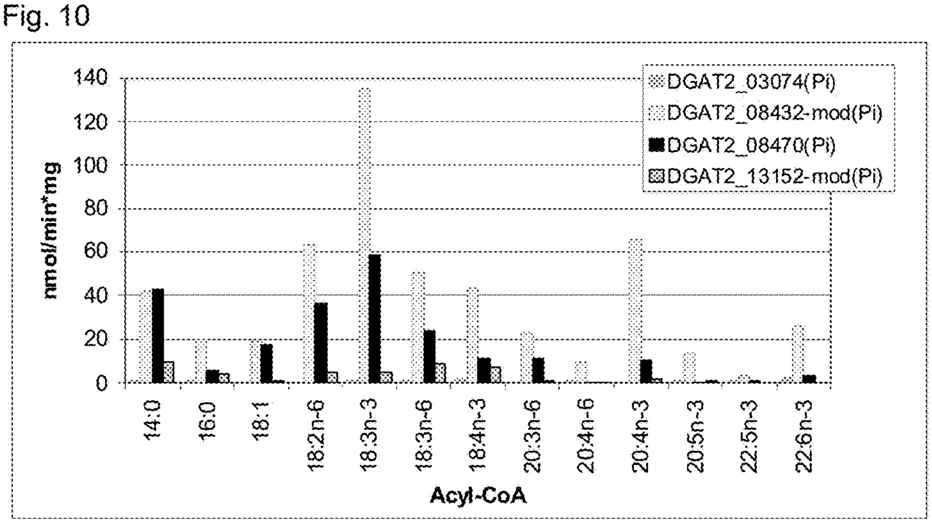
FIG. 10: Substrate specificity of DGAT2_03074 (Pi), DGAT2_08432-mod(Pi), DGAT2_08470 (Pi) and DGAT2_13152-mod(Pi).

FIG. 10: Substrate specificity of DGAT2_03074 (Pi), DGAT2_08432-mod(Pi), DGAT2_08470 (Pi) and DGAT2_13152-mod(Pi).

The specific activity of the enzymes DGAT2_03074 (Pi), DGAT2_08432-mod(Pi), DGAT2_08470 (Pi) and DGAT2_13152-mod(Pi) using the substrates indicated at the x-axis is gives as the amount (in nmol) of substrate/product consumed/produced in one minute per mg total protein and was determined as described in example 7. The specific activities measured for microsomal extracts of yeast harboring an empty vector (pYES2 ev) is shown as control.

This invention is further illustrated by the following examples which should not be construed as limiting the scope of the invention.

EXAMPLES

Example 1: General Cloning Methods

Cloning methods as e.g. use of restriction endonucleases to cut double stranded DNA at specific sites, agarose gel electrophoreses, purification of DNA fragments, transfer of nucleic acids onto nitrocellulose and nylon membranes, joining of DNA-fragments, transformation of *E. coli* cells and culture of bacteria where performed as described in Sambrook et al. (1989) (Cold Spring Harbor Laboratory Press: ISBN 0-87965-309-6)

Example 2: Sequence Analysis of Recombinant DNA

Sequencing of recombinant DNA-molecules was performed using a laser-fluorescence DNA sequencer (Applied Biosystems Inc, USA) employing the sanger method (Sanger et al. (1977) Proc. Natl. Acad. Sci. USA 74, 5463-5467). Expression constructs harboring fragments obtained by polymerase chain reactions were subjected to sequencing to confirm the correctness of expression cassettes consisting of promoter, nucleic acid molecule to be expressed and terminator to avoid mutations that might result from handling of the DNA during cloning, e.g. due to incorrect primers, mutations from exposure to UV-light or errors of polymerases.

Example 3: Cloning of Yeast Expression Construct Via Homologous Recombination The open reading frame listed in SEQ ID NOs: 1, 3, 5, 7, 9, 11, 13, 15, 17, 19, 21, 23, 25, 27, 29, 31, 33, 35, 37, 39, and 41 encoding polypeptides with the amino acid sequence SEQ ID NOs: 2, 4, 6, 8, 10, 12, 14, 16, 18, 20, 22, 24, 26, 28, 30, 32, 34, 36, 38, 40, and 42 that have acyltransferase activity can amplified using the primer listed in table 2 in a polymerase chain reaction. By doing so, the open reading frame is 5' fused to about 60 nucleotides of the 3' end of the GAL1 promotor sequence and 3' fused to about 60 nucleotides of the 5' end of the CYC1 terminator sequence. To integrate these fragments into pYES2.1 TOPO downstream of the galactose inducible GAL1 Promotor via homologous recombination, the vector pYES2.1 (Invitrogen) can be digested using the restriction endonucleases Pvu II and Xba I, and *Saccharomyces cerevisea* can be transformed with 5 to 20 ng of linearized pYES2.1 TOPO vector and 20 to 100 ng PCR product per 50 μl competent cells using the transformation method described by Schiestl et al. (Schiestl et al. (1989) Curr. Genet. 16(5-6), pp. 339-346), to obtain pYES-pLPLAT_01232 (Pi), pYES-pLPLAT_01330 (Pi), pYES-pLPLAT_07077 (Pi), pYES-LPLAT_18374 (Pi), pYES-pLPLAT_14816 (Pi), YES-pLPAAT_13842 (Pi), pYES-pLPAAT_10763 (Pi), pYES-LPCAT_02075 (Pi), pYES-pLPAAT_06638 (Pi), pYES-pDGAT1_12278 (Pi), pYES-DGAT2_03074 (Pi), pYES-pDGAT2_08467 (Pi), pYES-DGAT2_08470 (Pi), pYES-pDGAT2_03835-mod(Pi), pYES-DGAT2_11677-mod(Pi), pYES-DGAT2_08432-mod (Pi), pYES-pDGAT2_08431 (Pi), pYES-DGAT_13152-mod (Pi) in various wildtype yeast and yeast mutants. Positive transformants can be selected based on the complementation of the URA autotrophy of the chosen *S. cerevisia* strain. To validate the correctness of the expression construct harbored by a particular yeast clone, plasmids can be isolated as described in Current Protocols in Molecular Biology (Hoffmann, Curr. Protoc. Mol. Biol. 2001 May; Chapter 13:Unit13.11), transformed into *E. coli* for amplification and subjected to sequencing of the expression cassette as described in example 2.

TABLE 2

Primer sequences for cloning acyltransferase-polynucleotides of the invention for yeast expression

| Gene-Name | Primer | SEQ-ID |
|---|---|---|
| pLPLAT_01332(Pi) | Forward: ataaaagtatcaacaaaaaattgttaatatacctc-tatactttaacgtcaaggagaaaaaaccccg-gatcatgaactgccagcgtcatccaac | 43 |
| | Reverse: aactataaaaaaataaatagggacctagacttcaggtt-gtctaactccttccttttcggttagagcggat-ttattacaaggtcttcttactgttcg | 44 |
| pLPLAT_01330(Pi) | Forward: ataaaagtatcaacaaaaaattgttaatatacctc-tatactttaacgtcaaggagaaaaaaccccggatcatggac-cgcgtcgtggactttgt | 45 |
| | Reverse: aactataaaaaaataaatagggacctagacttcaggtt-gtctaactccttccttttcggttagagcggatttatcacaaa-tacttattaagtacct | 46 |
| pLPLAT_07077(Pi) | Forward: ataaaagtatcaacaaaaaattgttaatatacctc-tatactttaacgtcaaggagaaaaaaccccggatcatgcgtgtcac-tcgccgcattcg | 47 |
| | Reverse: aactataaaaaaataaatagggacctagacttcaggtt-gtctaactccttccttttcggttagagcggatttattactgcgtcttctt-gtcggtgg | 48 |
| LPLAT_18374(Pi) | Forward: ataaaagtatcaacaaaaaattgttaatatacctc-tatactttaacgtcaaggagaaaaaaccccggatcatgagcaccac-cgcgctattaca | 49 |
| | Reverse: aactataaaaaaataaatagggacctagacttcaggtt-gtctaactccttccttttcggttagagcggatttactacggaatctcga-gactgcttt | 50 |
| pLPLAT_14816(Pi) | Forward: ataaaagtatcaacaaaaaattgttaatatacctc-tatactttaacgtcaaggagaaaaaaccccggatcatgga-gaagtatagtcggtggtc | 51 |
| | Reverse: aactataaaaaaataaatagggacctagacttcaggtt-gtctaactccttccttttcggttagagcggatttactatctcttggcccatt-gggcgt | 52 |
| LPAAT_13842(Pi) | Forward: ataaaagtatcaacaaaaaattgttaatatacctc-tatactttaacgtcaaggagaaaaaaccccggatcatgtcgttcgc-tacacctgcgca | 53 |
| | Reverse: aactataaaaaaataaatagggacctagacttcaggtt-gtctaactccttccttttcggttagagcggatttattagcaggtgaa-gaacatgaggg | 54 |
| pLPAAT_10763(Pi) | Forward: ataaaagtatcaacaaaaaattgttaatatacctc-tatactttaacgtcaaggagaaaaaaccccggatcatgag-tcaaagtgacgagtgcca | 55 |
| | Reverse: aactataaaaaaataaatagggacctagacttcaggtt-gtctaactccttccttttcggttagagcggatttatcacgtgaagaggcg-caactcat | 56 |
| LPCAT_02075(Pi) | Forward: ataaaagtatcaacaaaaaattgttaatatacctc-tatactttaacgtcaaggagaaaaaaccccg-gatcatggcggtgttccacctgtactc | 57 |
| | Reverse: aactataaaaaaataaatagggacctagacttcaggtt-gtctaactccttccttttcggttagagcggatttatcacaga-tacttagcctggtgac | 58 |
| pLPAAT_06638(Pi) | Forward: ataaaagtatcaacaaaaaattgttaatatacctc-tatactttaacgtcaaggagaaaaaaccccg-gatcatgggcgtggctgttgtgggcgt | 59 |
| | Reverse: aactataaaaaaataaatagggacctagacttcaggtt-gtctaactccttccttttcggttagagcggatttactacgagttgtttatga-gaaacc | 60 |

TABLE 2-continued

| Primer sequences for cloning acyltransferase-polynucleotides of the invention for yeast expression | | |
|---|---|---|
| Gene-Name | Primer | SEQ-ID |
| pDGAT1_12278(Pi) | Forward: ataaaagtatcaacaaaaaattgttaatatacctc-tatactttaacgtcaaggagaaaaaaccccggatcatgggaccccgag-tggaacctcc | 61 |
| | Reverse: aactataaaaaaataaatagggacctagacttcaggtt-gtctaactccttccttttcggttagagcggatttattaggctt-gtttcttcctcaaac | 62 |
| DGAT2_03074(Pi) | Forward: ataaaagtatcaacaaaaaattgttaatatacctc-tatactttaacgtcaaggagaaaaaaccccggatcatgacaggccag-caacacacttg | 63 |
| | Reverse: aactataaaaaaataaatagggacctagacttcaggtt-gtctaactccttccttttcggttagagcggatttactagcgcacatgcagcg-tacagt | 64 |
| pDGAT2_08467(Pi) | Forward: ataaaagtatcaacaaaaaattgttaatatacctc-tatactttaacgtcaaggagaaaaaaccccggatcatgtcgg-cagcccaagtgctcaa | 65 |
| | Reverse: aactataaaaaaataaatagggacctagacttcaggtt-gtctaactccttccttttcggttagagcggatttattag-tatatttccaactgcgctt | 66 |
| DGAT2_08470(Pi) | Forward: ataaaagtatcaacaaaaaattgttaatatacctc-tatactttaacgtcaaggagaaaaaaccccggatcatggcgaa-gctcacgaatgcggc | 67 |
| | Reverse: aactataaaaaaataaatagggacctagacttcaggtt-gtctaactccttccttttcggttagagcggatttatcag-tataattcaagttcagcgt | 68 |
| pDGAT2_03835-mod(Pi) | Forward: ataaaagtatcaacaaaaaattgttaatatacctc-tatactttaacgtcaaggagaaaaaaccccg-gatcatggaggctttcgtcccagtgct | 69 |
| | Reverse: aactataaaaaaataaatagggacctagacttcaggtt-gtctaactccttccttttcggttagagcggatttatcagacgtaaatgagctt-gtagt | 70 |
| DGAT2_11677-mod(Pi) | Forward: ataaaagtatcaacaaaaaattgttaatatacctc-tatactttaacgtcaaggagaaaaaaccccg-gatcatggcgagcgaaactcaggctga | 71 |
| | Reverse: aactataaaaaaataaatagggacctagacttcaggtt-gtctaactccttccttttcggttagagcggatttacta-aatgatggccagcgtctcgt | 72 |
| DGAT2_08432-mod(Pi) | Forward: ataaaagtatcaacaaaaaattgttaatatacctc-tatactttaacgtcaaggagaaaaaaccccggatcatgccgcaagctt-gtggacggac | 73 |
| | Reverse: aactataaaaaaataaatagggacctagacttcaggtt-gtctaactccttccttttcggttagagcggat-ttatcagaaaatttctaattcggcgt | 74 |
| pDGAT2_08431(Pi) | Forward: ataaaagtatcaacaaaaaattgttaatatacctc-tatactttaacgtcaaggagaaaaaaccccggatcatggtcggcgtt-gcgcacgctgc | 75 |
| | Reverse: aactataaaaaaataaatagggacctagacttcaggtt-gtctaactccttccttttcggttagagcggat-ttattaaaaaatctccagggtggcgt | 76 |
| DGAT_13152-mod(Pi) | Forward: ataaaagtatcaacaaaaaattgttaatatacctc-tatactttaacgtcaaggagaaaaaaccccggatcatggacgtgga-gaacagtctttt | 77 |
| | Reverse: aactataaaaaaataaatagggacctagacttcaggtt-gtctaactccttccttttcggttagagcggatttattattttgtcttcttgtcaccgg | 78 |

TABLE 2-continued

Primer sequences for cloning acyltransferase-polynucleotides of the invention for yeast expression

| Gene-Name | Primer | SEQ-ID |
|---|---|---|
| pPDAT_11965-mod(Pi) | Forward: ataaaagtatcaacaaaaaattgttaatatacctc-tatactttaacgtcaaggagaaaaaaccccggatcatgacactggac-gacgattcctc | 79 |
| | Reverse: aactataaaaaaataaatagggacctagacttcaggtt-gtctaactccttccttttcggttagagcggatttattagagctctccgacac-gttcgg | 80 |
| pGPAT-PITG_18707 | Forward: ataaaagtatcaacaaaaaattgttaatatacctc-tatactttaacgtcaaggagaaaaaaccccggatcatgaagttcgac-gacaagaaggt | 81 |
| | Reverse: aactataaaaaaataaatagggacctagacttcaggtt-gtctaactccttccttttcggttagagcggatttactacacggacccctttac-gttgct | 82 |
| pGPAT-PITG_03371 | Forward: ataaaagtatcaacaaaaaattgttaatatacctc-tatactttaacgtcaaggagaaaaaaccccggatcatgctgtctacgc-tactatggct | 83 |
| | Reverse: aactataaaaaaataaatagggacctagacttcaggtt-gtctaactccttccttttcggttagagcggatttactatgtagtaagcag-tgtgtcgc | 84 |

TABLE 3

Coding polynucleotide sequences and amino acid sequences of the acyltransferases of the invention

| Gene name | Organism | Nucleotides in bp | SEQ-ID No. | Amino acids | SEQ-ID No. |
|---|---|---|---|---|---|
| pLPLAT_01332(Pi) | *Phythophtora* infestance | 1563 | 1 | 520 | 2 |
| pLPLAT_01330(Pi) | *Phythophtora* infestance | 1371 | 3 | 456 | 4 |
| pLPLAT_07077(Pi) | *Phythophtora* infestance | 1458 | 5 | 485 | 6 |
| LPLAT_18374(Pi) | *Phythophtora* infestance | 1677 | 7 | 558 | 8 |
| pLPLAT_14816(Pi) | *Phythophtora* infestance | 1047 | 9 | 348 | 10 |
| LPAAT_13842(Pi) | *Phythophtora* infestance | 1275 | 11 | 424 | 12 |
| pLPAAT_10763(Pi) | *Phythophtora* infestance | 1278 | 13 | 425 | 14 |
| LPCAT_02075(Pi) | *Phythophtora* infestance | 1173 | 15 | 390 | 16 |
| pLPAAT_06638(Pi) | *Phythophtora* infestance | 1110 | 17 | 369 | 18 |
| pDGAT1_12278(Pi) | *Phythophtora* infestance | 1344 | 19 | 447 | 20 |
| DGAT2_03074(Pi) | *Phythophtora* infestance | 927 | 21 | 308 | 22 |
| pDGAT2_08467(Pi) | *Phythophtora* infestance | 1179 | 23 | 392 | 24 |
| DGAT2_08470(Pi) | *Phythophtora* infestance | 1146 | 25 | 381 | 26 |
| pDGAT2_03835-mod(Pi) | *Phythophtora* infestance | 852 | 27 | 283 | 28 |
| DGAT2_11677-mod(Pi) | *Phythophtora* infestance | 1050 | 29 | 349 | 30 |
| DGAT2_08432-mod(Pi) | *Phythophtora* infestance | 1212 | 31 | 403 | 32 |
| pDGAT2_08431(Pi) | *Phythophtora* infestance | 1221 | 33 | 406 | 34 |
| DGAT_13152-mod(Pi) | *Phythophtora* infestance | 1551 | 35 | 516 | 36 |
| pPDAT_11965-mod(Pi) | *Phythophtora* infestance | 2028 | 37 | 675 | 38 |
| pGPAT-PITG_18707 | *Phythophtora* infestance | 2187 | 39 | 728 | 40 |
| pGPAT-PITG_03371 | *Phythophtora* infestance | 1533 | 41 | 510 | 42 |

Example 4: Activity Assays Using Yeast Extracts

To characterize the functions of the acyltransferase polypeptides of the invention, yeast mutants can be employed that are defective in certain acyltransferase activities. For example, the yeast mutant Y13749 (Genotype: BY4742; Mat alpha; his3Δ1; leu2Δ0; lys2Δ0; ura3Δ0; YDL052c::kanMX4) lacking LPAAT activity can be transformed with expression constructs harboring candidate polypeptides to check for restoration (complementation) of LPAAT activity, the yeast mutant Y12431 (genotype BY4742; Mat alpha; his3Δ1; leu2Δ0; lys2Δ0; ura3Δ0; YOR175c::kanMX4) lacking LPLAT activity can be transformed with expression constructs harboring candidate polypeptides to check for restoration (complementation) of LPLAT activity, the yeast mutant H1246 (genotype MATa leu2-3,112 trp11 can1-100 ura3-1 ade2-1 his3-11,15 YOR245::KanMX4 YNR008W::TRP1 YCR048W::HIS3 YNR019W::LEU2) lacking the ability to synthesize triacylglycerole can be transformed with expression constructs harboring candidate polypeptides to check for restoration (complementation) of the ability to synthesis triacylglycerole. The yeast mutants can for example harbor the expression constructs listed in example 3 employing the transformation method described in example 3.

For LPAAT activity assay, clones of the yeast mutant Y13749 harboring either one of pYES-pLPLAT_01232 (Pi), pYES-pLPLAT_01330 (Pi), pYES-pLPLAT_07077 (Pi), pYES-LPLAT_18374 (Pi), pYES-pLPLAT_14816 (Pi), YES-pLPAAT_13842 (Pi), pYES-pLPAAT_10763 (Pi), pYES-LPCAT_02075 (Pi), pYES-pLPAAT_06638 (Pi) can be grown at 28° C. in 10 ml selective media (SC-URA) with 2% raffinose as carbon source over night. The next day, expression of the acyltransferase polypeptides can be induced by transferring the cells to fresh media containing 2% galactose, for example by inoculating 100 ml of fresh culture to an optical density (measure at 600 nm) of $OD_{600}$=0.1. Cells are harvested after 24 h incubation at 28° C. by centrifugation at 3000×g for 5 min and resuspended in 1 ml resuspention buffer (25 mM Tris/HCL pH 7.6) and disrupted using acid washed zirconium bead (200 μm average diameter) in a mill (Resch, Germany) by three minutes agitation at 300 rpm. The supernatant is transferred to a fresh tube and centrifuged at 3000×g for 5 min. The obtained supernatant is the crude extract. Protein content is measured according to Bradford (Bradford, M. M. (1976), Anal. Biochem. Bd. 72, pp. 248-254) with bovine serum albumin as standard. Assay mixtures contain 50 μg of protein, 10 μl of 10 mM [$^{14}$C]-glycerole-3-phosphate (2000 dpm/nmol), 10 μl of 1 mM 18:1-CoA in assay buffer (25 mM Tris/HCL pH 7.6, 0.5 mg/ml BSA) to give a total volume of 100 μl. Samples are incubated for 10 min at 30° C. The assays are terminated by extraction of the lipids into chloroform according to Blight and Dyer (Bligh, E. G. and Dyer, W. J. (1959), Can. J. Biochem. Physiol. 37, pp. 911-917). Lipids are separated on thin layer chromatography (TLC) silica 60 plates (Merck) using chloroform/methanol/acetic acid/water (90:15:10:3), and autoradiographic pictures are taken using an instant imager (Packard). It can be seen by the formation of phosphatidic acid (PA) in FIG. 1, that LPLAT_18374 (Pi) and LPAAT_13842 (Pi) are polypeptides having LPAAT activity.

For LPCAT and LPEAT activity assay, clones of the yeast mutant Y12431 harboring either one of pYES-pLPLAT_01232 (Pi), pYES-pLPLAT_01330 (Pi), pYES-pLPLAT_07077 (Pi), pYES-LPLAT_18374 (Pi), pYES-pLPLAT_14816 (Pi), YES-pLPAAT_13842 (Pi), pYES-pLPAAT_10763 (Pi), pYES-LPCAT_02075 (Pi), pYES-pLPAAT_06638 (Pi) can be grown at 28° C. in 10 ml selective media (SC-URA) with 2% raffinose as carbon source over night. The next day, expression of the acyltransferase polypeptides can be induced by transferring the cells to fresh media containing 2% galactose, for example by inoculating 100 ml of fresh culture to an optical density (measure at 600 nm) of $OD_{600}$=0.1. Cells are harvested after 24 h incubation at 28° C. by centrifugation at 3000×g for 5 min and resuspended in 1 ml resuspention buffer (25 mM Tris/HCL pH 7.6) and disrupted using acid washed zirconium bead (200 μm average diameter) in a mill (Resch, Germany) by three minutes agitation at 300 rpm. The supernatant is transferred to a fresh tube and centrifuged at 3000×g for 5 min. The obtained supernatant is the crude extract. Protein content is measured according to Bradford (Bradford, M. M. (1976), Anal. Biochem. Bd. 72, pp. 248-254) with bovine serum albumin as standard. Assay mixtures contain either 10 μl 20 mM LPC (Larodan, from egg; LPCAT activity assay) or 10 μl 20 mM LPE (Larodan, from egg; LPEAT activity assay), 50 μg of protein, 10 μl of 1 mM [$^{14}$C]-18:1-CoA (5900 dpm/nmol) in assay buffer (25 mM Tris/HCL pH 7.6, 0.5 mg/ml BSA) to give a total volume of 100 μl. Samples are incubated for 10 min at 30° C. The assays are terminated by extraction of the lipids into chloroform according to Blight and Dyer (Bligh, E. G. and Dyer, W. J. (1959), Can. J. Biochem. Physiol. 37, pp. 911-917). Lipids are separated on thin layer chromatography (TLC) silica 60 plates (Merck) using chloroform/methanol/acetic acid/water (90:15:10:3), and autoradiographic pictures are taken using an instant imager (Packard). It can be seen by the formation of phosphatidylethanolamine (PE) in FIG. 2, that LPLAT_18374 (Pi) and LPCAT_02075 (Pi) are polypeptides having LPEAT activity. Correspondingly, formation of phosphatidylcholine (PC) in FIG. 3 indicates, that LPLAT_18374 (Pi) is a polypeptide having LPCAT activity.

For DGAT activity assay, clones of the yeast mutant H1246 harboring either one of pYES-pDGAT1_12278 (Pi), pYES-DGAT2_03074 (Pi), pYES-pDGAT2_08467 (Pi), pYES-DGAT2_08470 (Pi), pYES-pDGAT2_03835-mod (Pi), pYES-DGAT2_11677-mod(Pi), pYES-DGAT2_08432-mod(Pi), pYES-pDGAT2_08431 (Pi), pYES-DGAT_13152-mod(Pi) can be grown at 28° C. in 10 ml selective media (SC-URA) with 2% raffinose as carbon source over night. The next day, expression of the acyltransferase polypeptides can be induced by transferring the cells to fresh media containing 2% galactose, for example by inoculating 100 ml of fresh culture to an optical density (measure at 600 nm) of $OD_{600}$=0.1. Cells are harvested after reaching stationary phase during incubation at 28° C. by centrifugation at 3000×g for 5 min and resuspended in 2 ml resuspention buffer (phosphate buffered saline (PBS) pH 7.4, see Sambrook et al., "Molecular Cloning", Cold Spring Harbor Laboratory, 1989). The equivalent of 200 mg cell pellet is taken, the volume adjusted to 210 μl using PBS and 790 μl of methanol:chloroform (2:1) are added. Cells are disrupted using acid washed zirconium bead (200 μm average diameter) in a mill (Resch, Germany) by three minutes agitation at 300 rpm and lipids are extracted according to Blight and Dyer (Bligh, E. G. and Dyer, W. J. (1959), Can. J. Biochem. Physiol. 37, pp. 911-917). Lipids are separated on thin layer chromatography (TLC) silica 60 plates (Merck) using hexane:diethylether:acetic acid (70:30:1), and stained in iodine vapor. It can be seen by the formation of triacylglycerole (TAG) in FIG. 4, that DGAT2_03074 (Pi), DGAT2_08470 (Pi), DGAT2_11677-mod(Pi), DGAT2_11677-mod(Pi), DGAT2_08432-mod(Pi) and DGAT_13152-mod(Pi) are polypeptides having DGAT activity.

Example 5: Determination of Substrate Specificity for LPAAT

For determination of substrate specificities of the LPAAT enzymes, clones of the yeast mutant Y13749 (described in example 4) harboring either one of pYES-pLPLAT_01232 (Pi), pYES-pLPLAT_01330 (Pi), pYES-pLPLAT_07077 (Pi), pYES-LPLAT_18374 (Pi), pYES-pLPLAT_14816 (Pi), YES-pLPAAT_13842 (Pi), pYES-pLPAAT_10763 (Pi), pYES-LPCAT_02075 (Pi), pYES-pLPAAT_06638 (Pi) can be grown at 28° C. in 10 ml selective media (SC-URA) with 2% raffinose as carbon source over night. The next day, expression of the acyltransferase polypeptides can be induced by transferring the cells to fresh media containing 2% galactose, for example by inoculating 100 ml of fresh culture to an optical density (measure at 600 nm) of $OD_{600}$=0.1. Cells are harvested after 24 h incubation at 28° C. by centrifugation at 3000×g for 5 min and resuspended in 1 ml disruption buffer (20 mM Tris/HCL pH 7.6, 10 mM $MgCl_2$, 1 mM EDTA, 5% glycerol, 0.3 M $(NH_4)_2SO_4$) and disrupted using acid washed zirconium beads (200 μm average diameter) in a mill (Resch, Germany) by three minutes agitation at 300 rpm. The supernatant and the beads are transferred to a fresh tube. Disruption buffer is added up to 20 ml and the tube is centrifuged at 8000×g for 5 min. The obtained supernatant is centrifuged for 2 hrs at 42000 rpm at 4° C. The pellet (microsomal fraction) is resuspended in a small volume of 0.1 M phosphate buffer pH 7.2. Protein content in the microsomal fraction is measured according to Bradford (Bradford, M. M. (1976), Anal. Biochem. Bd. 72, pp. 248-254) with bovine serum albumin as standard. Assay mixtures contain 1-5 μg of microsomal protein (the amount is adjusted to achieve linear conditions without substrate limitation), 10 μl of 1 mM [$^{14}C$]-18:1-LPA (5000 dpm/nmol), 10 μl of 1 mM acyl-CoA in assay buffer (0.1 M phosphate buffer pH 7.2., 10 mg/ml Bovine Serum Albumine (BSA)) to give a total volume of 100 μl. Like to amount of microsomal protein added to the assay, also the amount of BSA has influence on observed anzmye activities, where higher amounts of BSA result on lower activities and lower amounts of BSA result in higher activities. The enzyme specificity can be tested for different acyl-CoA:s, e.g. 14:0-CoA, 16:0-CoA, 18:1-CoA, 18:2-CoA, 18:3-CoA, γ18:3-CoA, 18:4-CoA, 20:3-CoA, 20:4-CoA, 20:4(n-3)-CoA, 20:5-CoA, 22:5-CoA, 22:6-CoA. Samples are incubated for 4 min at 30° C. The assays are terminated by extraction of the lipids into chloroform according to Bligh and Dyer (Bligh, E. G. and Dyer, W. J. (1959), Can. J. Biochem. Physiol. 37, pp. 911-917). Lipids are separated on thin layer chromatography (TLC) silica 60 plates (Merck) using chloroform/methanol/acetic acid/water (90:15:10:3), and autoradiographic pictures are taken using an instant imager (Packard). The amount of phosphatidic acid (PA) produced in the reaction (and hence the enzyme activity) can be determined from the picture. The enzyme activity in the presence of 10 mg/ml BSA in the assay of LPAAT_13842 (Pi) for the different substrates can be seen in FIG. 5. The enzyme activity of AtLPAAT2-At3g57650 (SEQ-ID 86, encoded by SEQ-ID 85) from *Arabidopsis thaliana* and the corresponding homologous protein form *Brassica napus* BnLPAAT2 (SEQ-ID 88, encoded by SEQ-ID 87) for the different substrates in the presence of 0 mg/ml BSA in the assays can be seen in FIG. 6. Comparing FIG. 5 and FIG. 6 clearly shows, that pYES-LPAAT_13842 (Pi) is not as selective as AtLPAAT2 and BnLPAAT2 towards the length and the desaturation state of the substrate fatty acid. The result in FIG. 6 suggests, that the endogenous LPAAT2 in *Arabidopsis* and *Brassica napus* has limited capability to contribute to incorporation of LC-PUFAs such as ARA (20:4n-6), EPA (20:5n-3) and DHA (22:6n-3) into oil during oil biosynthesis in seeds. It can be expected that overexpression of LPAAT_13842 (Pi) in seeds of oilseed crops results in much better storage of these PUFAs in oil. It is understood, that the absolute activities of FIG. 6 and FIG. 5 cannot be compared, as it was required to add 10 mg/ml of BSA to the assays shown FIG. 5 to reduce the activities to linear levels, that is avoiding equal saturated activities for each substrate due to the fast turnaround of the substrates. This was not required for the assays shown in FIG. 6, as the activities of BnLAAT2 and AtLAAPT2 where low enough to keep within a linear range. Linear range in this context is synonymous for e.g. observing twice the activity when incubating twice as long.

Example 6: Determination of Substrate Specificity for LPLAT

For LPCAT and LPEAT activity assay, clones of the yeast mutant Y12431 harboring either one of pYES-pLPLAT_01232 (Pi), pYES-pLPLAT_01330 (Pi), pYES-pLPLAT_07077 (Pi), pYES-LPLAT_18374 (Pi), pYES-pLPLAT_14816 (Pi), YES-pLPAAT_13842 (Pi), pYES-pLPAAT_10763 (Pi), pYES-LPCAT_02075 (Pi), pYES-pLPAAT_06638 (Pi) can be grown at 28° C. in 10 ml selective media (SC-URA) with 2% raffinose as carbon source over night. The next day, expression of the acyltransferase polypeptides can be induced by transferring the cells to fresh media containing 2% galactose, for example by inoculating 100 ml of fresh culture to an optical density (measure at 600 nm) of $OD_{600}$=0.1 Cells are harvested after 24 h incubation at 28° C. by centrifugation at 3000×g for 5 min and resuspended in 1 ml disruption buffer (20 mM Tris/HCL pH 7.6, 10 mM $MgCl_2$, 1 mM EDTA, 5% glycerol, 0.3 M $(NH_4)_2SO_4$) and disrupted using acid washed zirconium beads (200 μm average diameter) in a mill (Resch, Germany) by three minutes agitation at 300 rpm. The supernatant and the beads are transferred to a fresh tube. Disruption buffer is added up to 20 ml and the tube is centrifuged at 8000×g for 5 min. The obtained supernatant is centrifuged for 2 hrs at 42000 rpm at 4° C. The pellet (microsomal fraction) is resuspended in a small volume of 0.1 M phosphate buffer pH 7.2. Protein content in the microsomal fraction is measured according to Bradford (Bradford, M. M. (1976), Anal. Biochem. Bd. 72, pp. 248-254) with bovine serum albumin as standard. Assay mixtures contain either 10 μl 1 mM [$^{14}C$]-18:1-Lysophosphatidlycholine (-LPC), 5000 dpm/nmol (LPCAT assay) or 10 μl 1 mM [$^{14}C$]-18:1-Lysophosphatidylethanolamine (-LPE), 5000 dpm/nmol (LPEAT assay), 1-10 μg of microsomal protein (the amount is adjusted to achieve linear conditions without substrate limitation), 10 μl of 1 mM acyl-CoA in assay buffer (0.1 M phosphate buffer pH 7.2., 10 mg/ml BSA) to give a total volume of 100 μl. Like to amount of microsomal protein added to the assay, also the amount of BSA has influence on observed anzmye activities, where higher amounts of BSA result on lower activities and lower amounts of BSA result in higher activities. The enzyme specificity can be tested for different acyl-CoA:s, e.g. 14:0-CoA, 16:0-CoA, 18:1-CoA, 18:2-CoA, 18:3-CoA, γ18:3-CoA, 18:4-CoA, 20:3-CoA, 20:4-CoA, 20:4(n-3)-CoA, 20:5-CoA, 22:5-CoA, 22:6-CoA. Samples are incubated for 4 min at 30° C. The assays are terminated by extraction of the lipids into chloroform according to Bligh and Dyer (Bligh, E. G. and Dyer, W. J. (1959), Can. J. Biochem. Physiol. 37, pp. 911-917). Lipids are separated on thin layer chromatography (TLC) silica 60 plates (Merck) using chloroform/methanol/acetic acid/water (90:15:10:3), and autoradiographic pictures are taken using an instant imager (Packard). The amount of phosphatidyl choline (PC) or phosphatidyl ethanol amine (PE) produced in the reaction (and hence the enzyme activity) can be determined from the picture. The enzyme activity of LPLAT_18374 (Pi and LPCAT_02075 (Pi) for the different substrates and using LPC as fatty acid aceptor can be seen in FIG. 7. The enzyme activity of LPLAT_18374 (Pi) and for the different substrates and using LPE as fatty acid aceptor can be seen in FIG. 8. The enzyme activity of AtLPCAT1-At1g12640 (SEQ-ID 90, encoded by SEQ-ID 89) and AtLPCAT2-At1g63050 (SEQ-ID 92, encoded by SEQ-ID 90) from *Arabidopsis thaliana* and the corresponding homologous protein from *Brassica napus* BnLPCAT1 (SEQ-ID 94, encoded by SEQ-ID 93) and BnLPCAT2 (SEQ-ID 96, encoded by SEQ-ID 95) for the different substrates in the presence of 0 mg/ml BSA in the assay can be seen in FIG. 9. Comparing FIG. 7 and FIG. 9 clearly shows, that LPLAT_18374 (Pi) is not as selective as AtLPAAT1 or AtLPCAT2 or BnLPCAT1 or BnLPCAT2 towards the length and the desaturation state of the substrate fatty acid. The result in FIG. 9 suggests, that the endogenous LPCAT1 and LPCAT2 in *Arabidopsis* and *Brassica napus* have a limited capability to contribute to exchange of intermediates occurring during the synthesis of DHA, such as 20:3n-6, 20:4n-6, 20:4n-3, 20:5n-3, or intermediates during synthesis of ARA, such as 20:3n-6, or intermediates during the synthesis of EPA, such as 20:3n-6, 20:4n-6, 20:4n-3, between the lipid pool and the CoA pool, and therefore pose a bottleneck for efficient synthesis of DHA. In contrast, it can be expected that overexpression of LPLAT_18374 (Pi) in seeds of oilseed crops results in much better exchange of aforementioned intermediates, resulting in more efficient synthesis of DHA, ARA or EPA, which leads to higher amount of DHA, ARA or EPA stored in oil of oilseed crops. It is understood, that the absolute activities of FIG. 9 with those of FIGS. 7 and 8 cannot be compared, as it was required to add 10 mg/ml of BSA to the assays shown FIGS. 7 and 8 to reduce the activities to linear levels, that is avoiding equal saturated activities for each substrate due to the fast turnaround of the substrates. This was not required for the assays shown in FIG. 9, as the activities of AtLPCAT1, AtLPCAT2, BnLCAT1 and BnLCAT2 where low enough to keep within a linear range. Linear range in this context is synonymous for e.g. observing twice the activity when incubating twice as long.

Example 7: Determination of Substrate Specificity for DGAT

For DGAT activity assay, clones of the yeast mutant H1246 harboring either one of pYES-pDGAT1_12278 (Pi), pYES-DGAT2_03074 (Pi), pYES-pDGAT2_08467 (Pi), pYES-DGAT2_08470 (Pi), pYES-pDGAT2_03835-mod (Pi), pYES-DGAT2_11677-mod(Pi), pYES-DGAT2_08432-mod(Pi), pYES-pDGAT2_08431 (Pi), pYES-DGAT_13152-mod(Pi) can be grown at 28° C. in 10 ml selective media (SC-URA) with 2% raffinose as carbon source over night. The next day, expression of the acyltransferase polypeptides can be induced by transferring the cells to fresh media containing 2% galactose, for example by inoculating 100 ml of fresh culture to an optical density (measure at 600 nm) of $OD_{600}$=0.1. Cells are harvested after 24 h incubation at 28° C. by centrifugation at 3000×g for 5 min and resuspended in 1 ml disruption buffer (20 mM Tris/HCL pH 7.6, 10 mM $MgCl_2$, 1 mM EDTA, 5% glycerol, 0.3 M $(NH_4)_2SO_4$) and disrupted using acid washed zirconium beads (200 μm average diameter) in a mill (Resch, Germany) by three minutes agitation at 300 rpm. The supernatant and the beads are transferred to a fresh tube. Disruption buffer is added up to 20 ml and the tube is centrifuged at 8000×g for 5 min. The obtained supernatant is centrifuged for 2 hrs at 42000 rpm at 4° C. The pellet (microsomal fraction) is resuspended in a small volume of 0.1 M phosphate buffer pH 7.2. Protein content in the microsomal fraction is measured according to Bradford (Bradford, M. M. (1976), Anal. Biochem. Bd. 72, pp. 248-254) with bovine serum albumin as standard. Assay mixtures contain 5 μl 1 mM [$^{14}$C]-6:0-DAG, 3000 dpm/nmol, 1-100 μg of microsomal protein (the amount is adjusted to achieve linear conditions without substrate limitation), 5 μl of 1 mM acyl-CoA in assay buffer (50 mM Hepes buffer pH 7.2, 1 mg/ml BSA) to give a total volume of 100 μl. The enzyme specificity can be tested for different acyl-CoA:s, e.g. 14:0-CoA, 16:0-CoA, 18:1-CoA, 18:2-CoA, 18:3-CoA, γ18:3-CoA, 18:4-CoA, 20:3-CoA, 20:4-CoA, 20:4(n-3)-CoA, 20:5-CoA, 22:5-CoA, 22:6-CoA. Samples are incubated for 4 min at 30° C. The assays are terminated by extraction of the lipids into chloroform according to Bligh and Dyer (Bligh, E. G. and Dyer, W. J. (1959), Can. J. Biochem. Physiol. 37, pp. 911-917). Lipids are separated on thin layer chromatography (TLC) silica 60 plates (Merck) using hexane:diethylether:acetic acid (70:30:1), and autoradiographic pictures are taken using an instant imager (Packard). The amount of triacylglycerol (TAG) produced in the reaction (and hence the enzyme activity) can be determined from the picture. The enzyme activity of DGAT2_03074 (Pi), DGAT2_08470 (Pi), DGAT2_08432-mod(Pi) and DGAT_13152-mod(Pi) for the different substrates can be seen in FIG. 10. The data in FIG. 10 show that all DGAT2 enzymes shown in this figure have different activities for the various substrates.

The invention claimed is:

1. A polynucleotide comprising an expression control sequence operatively linked to a heterologous nucleic acid sequence selected from the group consisting of:

a) the nucleic acid sequence of SEQ ID NO: 15;

b) a nucleic acid sequence encoding a polypeptide having the amino acid sequence of SEQ ID NO: 16;

c) a nucleic acid sequence having at least 45% sequence identity to the nucleic acid sequence of a) or b), wherein the nucleic acid sequence encodes a polypeptide having acyltransferase activity;

d) a nucleic acid sequence encoding a polypeptide having acyltransferase activity and having at least 45% sequence identity to the amino acid sequence of SEQ ID NO: 16; and e) a nucleic acid sequence that hybridizes to the nucleic acid sequence of a) or b) under stringent conditions comprising hybridization in 6× sodium chloride/sodium citrate (SSC) at approximately 45° C., followed by one or more wash steps in 0.2×SSC, 0.1% SDS at 50 to 65° C., wherein the nucleic acid sequence encodes a polypeptide having acyltransferase activity.

2. The polynucleotide of claim 1, wherein the polynucleotide further comprises a terminator sequence operatively linked to the nucleic acid sequence.

3. A vector comprising the polynucleotide of claim 1.

4. A host cell comprising:

a) the polynucleotide of claim 1; or b) a vector comprising said polynucleotide.

5. A method for the manufacture of a polypeptide encoded by the polynucleotide of claim 1, comprising:

a) cultivating a host cell comprising the polynucleotide of claim 1 under conditions that allow for production of the polypeptide; and b) obtaining the polypeptide from the host cell of step a).

6. A recombinant polypeptide comprising the polypeptide encoded by the polynucleotide of claim 1.

7. A non-human transgenic organism comprising:

a) the polynucleotide of claim 1; or b) a vector comprising said polynucleotide.

8. The non-human transgenic organism of claim 7, which is a plant, plant part or plant seed.

9. A method for the manufacture of a polyunsaturated fatty acid comprising:

a) cultivating the host cell of claim 4 under conditions allowing for the production of the polyunsaturated fatty acid in the host cell; and b) obtaining the polyunsaturated fatty acid from the host cell.

10. The method of claim 9, wherein the polyunsaturated fatty acid is eicosapentaenoic acid and/or docosahexaenoic acid.

11. A method for the manufacture of an oil, lipid or fatty acid composition comprising the steps of the method of claim 9 and a further step of formulating the polyunsaturated fatty acid as an oil, lipid or fatty acid composition.

12. The method of claim 11, wherein the oil, lipid or fatty acid composition is used for feed, foodstuffs, cosmetics or medicaments.

13. A method for the manufacture of a polyunsaturated fatty acid comprising:

a) cultivating the non-human transgenic organism of claim 7 under conditions allowing for the production of the polyunsaturated fatty acid in the non-human transgenic organism; and b) obtaining the polyunsaturated fatty acid from the non-human transgenic organism.

14. The method of claim 13, wherein the polyunsaturated fatty acid is eicosapentaenoic acid and/or docosahexaenoic acid.

15. A method for the manufacture of an oil, lipid or fatty acid composition comprising the steps of the method of claim 13 and a further step of formulating the polyunsaturated fatty acid as an oil, lipid or fatty acid composition.

16. A method for the manufacture of polyunsaturated fatty acids, comprising:

a) cultivating a plant comprising the polynucleotide of claim 1 or a vector comprising said polynucleotide under conditions which allow for the production of polyunsaturated fatty acids in said plant or seeds thereof; and b) obtaining said polyunsaturated fatty acids from said plant or seeds thereof.

17. The method of claim 16, wherein the polyunsaturated fatty acids are obtained from the seeds of said plant.

18. The method of claim 16, wherein the polyunsaturated fatty acids are eicosapentaenoic acid and/or docosahexaenoic acid.

19. A method for the manufacture of an oil, lipid or fatty acid composition comprising the steps of the method of claim 16 and a further step of formulating the polyunsaturated fatty acids as an oil, lipid or fatty acid composition.

20. A method for the production of feed, foodstuffs, cosmetics or pharmaceuticals, comprising:

a) obtaining an oil-, lipid- or fatty acid-composition produced by the method of claim 19; and b) processing said oil-, lipid- or fatty acid-composition to produce feed, foodstuffs, cosmetics or pharmaceuticals.

21. The polynucleotide of claim 1, wherein:

a) the nucleic acid sequence has at least 70% sequence identity to the nucleic acid sequence of a) or b) and encodes a polypeptide having acyltransferase activity; or b) the nucleic acid sequence encodes a polypeptide having acyltransferase activity and having at least 70% sequence identity to the amino acid sequence of SEQ ID NO: 16.

22. The polynucleotide of claim 1, wherein:

a) the nucleic acid sequence has at least 80% sequence identity to the nucleic acid sequence of a) or b) and encodes a polypeptide having acyltransferase activity; or b) the nucleic acid sequence encodes a polypeptide having acyltransferase activity and having at least 80% sequence identity to the amino acid sequence of SEQ ID NO: 16.

23. The polynucleotide of claim 1, wherein:

a) the nucleic acid sequence has at least 90% sequence identity to the nucleic acid sequence of a) or b) and encodes a polypeptide having acyltransferase activity; or b) the nucleic acid sequence encodes a polypeptide having acyltransferase activity and having at least 90% sequence identity to the amino acid sequence of SEQ ID NO: 16.

* * * * *

SEQUENCE LISTING

```
<160> NUMBER OF SEQ ID NOS: 96

<210> SEQ ID NO 1
<211> LENGTH: 1563
<212> TYPE: DNA
<213> ORGANISM: Phythophtora infestance

<400> SEQUENCE: 1

atgaactgcc agcgtcatcc aacacacgtc gcacatgaca tcaccttcgg cagcatcctt      60

gccatcctcg ccgcgcagcc tcccattcct gtttctgcct cgcatttggc actcatggct     120

tctcacgttg tctcgtcgct gagtaatgca gccactccgc tgcgattcac cttgttaaac     180

cagcagctca cacaactctc ggagctcgta ggggttccag tggaccaact acgttgcgtc     240

gcttgcctgt tagctgtcta cccattggca cttatcgtgc gcaagttgcc gtcggtcaca     300

gctaagcatt ggctgcacat ttgcgctggt gtgagcatcg cccaattcgt ctatggaaca     360

ggatggctac actcgcttct atcctcgctg gtcacgtacg cgttggtgtg cgtgctgccg     420

cccaaacgcg caccgttcgt ggtgtttctc gccaatatgt tgtttgtggc ggcactgcac     480
```

-continued

```
atccaccgta tgcgagtcaa ctatatgggc tggagtatgg actcgacagc gagtcagatg     540

ctgctgctca tcaagctcac gagcttcgcc ttcaactacc acgatggtgt tgttcccagt     600

gccacagcag tgcagaacgg cgactcagag cacacgaaaa gagtcaagca gttgcgtaaa     660

caactggcga tcccacagat cccgtcactg ctggagtttt tgggcttcgt ctactgcttc     720

acgacgttcc tggccggtcc ggcatttgag tacaaagagt acagcgacgc tattcaccag     780

gctaggttcg tcgacaacaa cggtgtccga cgtaatgtgt cccctgcgcg tgcggcaatg     840

tccaagttgg tattgggtct tggacttatg ggacttttgg tgcagttcgg agctctagcc     900

gacttgaatc agattttgaa cgatgagaat cagtccatgc tcatgaagtg gggcgacta      960

tttgtcgcgt tgttcttgac tcgtgccaag tattacgtgg cgtggaaact ggcggagggg    1020

gcgactgtgc tgaccggaac gggattcgaa ggattcgacg agcagaacaa ccccaaaggc    1080

tgggatggtg tcagtaatgt ggacatcctg ggcttcgaac tcggcgccaa cgtgcgtgag    1140

atctcgcgtg cttggaacaa gggcacgcag aactggctgg agcgttatgt gtacacacgc    1200

acgggcaact cgttgcttgc cacgtactct gtatcggctc tgtggcacgg attctaccct    1260

ggttactatc tcttcttcct cacggtgccg cttgcgacgt ctgtgaatcg cctggcgcga    1320

cgtcacgtgc gtccgtacgt tgtggacagc ccgctgaagc cactctacga cctcgtcggt    1380

atgatctgta ctgctttggt cgtcaactac ttggccgtct cgttcgtagt gctgtcgtgg    1440

gaggacgcag ttgctggttt ccgctccatg cgctttactg gccacgtcgg gcttgtgggc    1500

tgctacttgt tgctcacctt tgtgcctatc aagaagactg cgaacagtaa gaagaccttg    1560

taa                                                                  1563
```

<210> SEQ ID NO 2
<211> LENGTH: 520
<212> TYPE: PRT
<213> ORGANISM: Phythophtora infestance

<400> SEQUENCE: 2

```
Met Asn Cys Gln Arg His Pro Thr His Val Ala His Asp Ile Thr Phe
1               5                   10                  15

Gly Ser Ile Leu Ala Ile Leu Ala Ala Gln Pro Pro Ile Pro Val Ser
            20                  25                  30

Ala Ser His Leu Ala Leu Met Ala Ser His Val Val Ser Ser Leu Ser
        35                  40                  45

Asn Ala Ala Thr Pro Leu Arg Phe Thr Leu Leu Asn Gln Gln Leu Thr
    50                  55                  60

Gln Leu Ser Glu Leu Val Gly Val Pro Val Asp Gln Leu Arg Cys Val
65                  70                  75                  80

Ala Cys Leu Leu Ala Val Tyr Pro Leu Ala Leu Ile Val Arg Lys Leu
                85                  90                  95

Pro Ser Val Thr Ala Lys His Trp Leu His Ile Cys Ala Gly Val Ser
            100                 105                 110

Ile Ala Gln Phe Val Tyr Gly Thr Gly Trp Leu His Ser Leu Leu Ser
        115                 120                 125

Ser Leu Val Thr Tyr Ala Leu Val Cys Val Leu Pro Pro Lys Arg Ala
    130                 135                 140

Pro Phe Val Val Phe Leu Ala Asn Met Leu Phe Val Ala Ala Leu His
145                 150                 155                 160

Ile His Arg Met Arg Val Asn Tyr Met Gly Trp Ser Met Asp Ser Thr
                165                 170                 175
```

-continued

```
Ala Ser Gln Met Leu Leu Leu Ile Lys Leu Thr Ser Phe Ala Phe Asn
            180                 185                 190

Tyr His Asp Gly Val Val Pro Ser Ala Thr Ala Val Gln Asn Gly Asp
        195                 200                 205

Ser Glu His Thr Lys Arg Val Lys Gln Leu Arg Lys Gln Leu Ala Ile
    210                 215                 220

Pro Gln Ile Pro Ser Leu Leu Glu Phe Leu Gly Phe Val Tyr Cys Phe
225                 230                 235                 240

Thr Thr Phe Leu Ala Gly Pro Ala Phe Glu Tyr Lys Glu Tyr Ser Asp
                245                 250                 255

Ala Ile His Gln Ala Arg Phe Val Asp Asn Asn Gly Val Arg Arg Asn
            260                 265                 270

Val Ser Pro Ala Arg Ala Ala Met Ser Lys Leu Val Leu Gly Leu Gly
        275                 280                 285

Leu Met Gly Leu Leu Val Gln Phe Gly Ala Leu Ala Asp Leu Asn Gln
    290                 295                 300

Ile Leu Asn Asp Glu Asn Gln Ser Met Leu Met Lys Trp Gly Arg Leu
305                 310                 315                 320

Phe Val Ala Leu Phe Leu Thr Arg Ala Lys Tyr Tyr Val Ala Trp Lys
                325                 330                 335

Leu Ala Glu Gly Ala Thr Val Leu Thr Gly Thr Gly Phe Glu Gly Phe
            340                 345                 350

Asp Glu Gln Asn Asn Pro Lys Gly Trp Asp Gly Val Ser Asn Val Asp
        355                 360                 365

Ile Leu Gly Phe Glu Leu Gly Ala Asn Val Arg Glu Ile Ser Arg Ala
    370                 375                 380

Trp Asn Lys Gly Thr Gln Asn Trp Leu Glu Arg Tyr Val Tyr Thr Arg
385                 390                 395                 400

Thr Gly Asn Ser Leu Leu Ala Thr Tyr Ser Val Ser Ala Leu Trp His
                405                 410                 415

Gly Phe Tyr Pro Gly Tyr Tyr Leu Phe Phe Leu Thr Val Pro Leu Ala
            420                 425                 430

Thr Ser Val Asn Arg Leu Ala Arg Arg His Val Arg Pro Tyr Val Val
        435                 440                 445

Asp Ser Pro Leu Lys Pro Leu Tyr Asp Leu Val Gly Met Ile Cys Thr
    450                 455                 460

Ala Leu Val Val Asn Tyr Leu Ala Val Ser Phe Val Val Leu Ser Trp
465                 470                 475                 480

Glu Asp Ala Val Ala Gly Phe Arg Ser Met Arg Phe Thr Gly His Val
                485                 490                 495

Gly Leu Val Gly Cys Tyr Leu Leu Leu Thr Phe Val Pro Ile Lys Lys
            500                 505                 510

Thr Ala Asn Ser Lys Lys Thr Leu
        515                 520
```

<210> SEQ ID NO 3
<211> LENGTH: 1371
<212> TYPE: DNA
<213> ORGANISM: Phythophtora infestance

<400> SEQUENCE: 3

```
atggaccgcg tcgtggactt tgtggagcac ctgcagccgt acacggagct tgccactcct      60

ttggacttca gtttcctcca tgcaaaagtg gacgagctgt ccgtgtcgct cggtctgggc     120

agcgaccagc tctgctacgt cctctgccta ttcgctgcgt atccgctggc tgttgtgtac     180
```

-continued

```
aaactgctac ccggtgccag cctcaagcac gtgtttgatg tggtgctagg tgtgagcatc    240

gctcagttcg tgctgggctc cggctgggtg cactcgttca tctcgagctt cctgacgtac    300

ctgatcgtta agttcgggcc atccaagcac gcgccaggca tcgtgttcct cttcaacatg    360

ctatacatgt cagcgtcaca catctaccgt ttgtatgtgg actacatggg ttggacgctg    420

gacttcaccg gcccgcagat gctgctggtc atcaagctca ccagcttcgc ctacaactac    480

tacgacggcg tggtggacaa gacgtttgag aagaaaggtg ccgagatgtc ccccggcata    540

aagaaagtgt acgaaggacg tcagaagctc gctatccagg agatcccgtc tctgctcgag    600

ttcttcggct acgtgtacag cttcaccacc ttcctggccg gcccggcgtt cgagatccgc    660

gagtatttgg acgtgacgag cggcaaaaag ttccttatgg acggcaagaa caaagagccg    720

tcgagtgtgc tcgctgcgtt ctctaaattc ctggtgggat cgctgttgat ggctgcgttc    780

gctgtgtatg gccccatgta cccgctgtcg aacctgcacg accccaagat cgctgcgcag    840

ccgttgctgt accagatccg cgacctgtac atcgcgctga tcttctgcaa ggccaagtat    900

tactccgcct ggaagattgc cgagggcgcc accgtgctgt gtggcttcgg attcgagggc    960

ttcaacaagg acggaaccag tcgcggctgg aacggtgtga gcaacatgga catcttgggc   1020

tttgagttct cgcagagcat ccgtgcggcc tcgcgagcct ggaacaaggg gacgcagaac   1080

tggctggaac gctacgtgta cacgcgcacg ggcaactcgc tgatggccac gtacttcatc   1140

tcagccttct ggcacggatt ctacccgggc tactacattt tcttcatgag tctgccgctg   1200

gctacggcgg tgaaccgttt ggctttcaag cgtcttcgtc cacgtttcat cgaggccgac   1260

ggatcgttcg gagccaagaa gaaaatttac gacgtgctca gctacttgtt gacgctcttc   1320

gctatgcact acttcgtcat gccgttccag gtacttaata agtatttgtg a             1371
```

```
<210> SEQ ID NO 4
<211> LENGTH: 456
<212> TYPE: PRT
<213> ORGANISM: Phythophtora infestance

<400> SEQUENCE: 4

Met Asp Arg Val Val Asp Phe Val Glu His Leu Gln Pro Tyr Thr Glu
1               5                   10                  15

Leu Ala Thr Pro Leu Asp Phe Ser Phe Leu His Ala Lys Val Asp Glu
            20                  25                  30

Leu Ser Val Ser Leu Gly Leu Gly Ser Asp Gln Leu Cys Tyr Val Leu
        35                  40                  45

Cys Leu Phe Ala Ala Tyr Pro Leu Ala Val Val Tyr Lys Leu Leu Pro
    50                  55                  60

Gly Ala Ser Leu Lys His Val Phe Asp Val Val Leu Gly Val Ser Ile
65                  70                  75                  80

Ala Gln Phe Val Leu Gly Ser Gly Trp Val His Ser Phe Ile Ser Ser
                85                  90                  95

Phe Leu Thr Tyr Leu Ile Val Lys Phe Gly Pro Ser Lys His Ala Pro
            100                 105                 110

Gly Ile Val Phe Leu Phe Asn Met Leu Tyr Met Ser Ala Ser His Ile
        115                 120                 125

Tyr Arg Leu Tyr Val Asp Tyr Met Gly Trp Thr Leu Asp Phe Thr Gly
    130                 135                 140

Pro Gln Met Leu Leu Val Ile Lys Leu Thr Ser Phe Ala Tyr Asn Tyr
145                 150                 155                 160
```

-continued

```
Tyr Asp Gly Val Val Asp Lys Thr Phe Glu Lys Lys Gly Ala Glu Met
                165                 170                 175

Ser Pro Gly Ile Lys Lys Val Tyr Glu Gly Arg Gln Lys Leu Ala Ile
            180                 185                 190

Gln Glu Ile Pro Ser Leu Leu Glu Phe Phe Gly Tyr Val Tyr Ser Phe
        195                 200                 205

Thr Thr Phe Leu Ala Gly Pro Ala Phe Glu Ile Arg Glu Tyr Leu Asp
    210                 215                 220

Val Thr Ser Gly Lys Lys Phe Leu Met Asp Gly Lys Asn Lys Glu Pro
225                 230                 235                 240

Ser Ser Val Leu Ala Ala Phe Ser Lys Phe Leu Val Gly Ser Leu Leu
                245                 250                 255

Met Ala Ala Phe Ala Val Tyr Gly Pro Met Tyr Pro Leu Ser Asn Leu
            260                 265                 270

His Asp Pro Lys Ile Ala Ala Gln Pro Leu Leu Tyr Gln Ile Arg Asp
        275                 280                 285

Leu Tyr Ile Ala Leu Ile Phe Cys Lys Ala Lys Tyr Tyr Ser Ala Trp
    290                 295                 300

Lys Ile Ala Glu Gly Ala Thr Val Leu Cys Gly Phe Gly Phe Glu Gly
305                 310                 315                 320

Phe Asn Lys Asp Gly Thr Ser Arg Gly Trp Asn Gly Val Ser Asn Met
                325                 330                 335

Asp Ile Leu Gly Phe Glu Phe Ser Gln Ser Ile Arg Ala Ala Ser Arg
            340                 345                 350

Ala Trp Asn Lys Gly Thr Gln Asn Trp Leu Glu Arg Tyr Val Tyr Thr
        355                 360                 365

Arg Thr Gly Asn Ser Leu Met Ala Thr Tyr Phe Ile Ser Ala Phe Trp
    370                 375                 380

His Gly Phe Tyr Pro Gly Tyr Tyr Ile Phe Phe Met Ser Leu Pro Leu
385                 390                 395                 400

Ala Thr Ala Val Asn Arg Leu Ala Phe Lys Arg Leu Arg Pro Arg Phe
                405                 410                 415

Ile Glu Ala Asp Gly Ser Phe Gly Ala Lys Lys Lys Ile Tyr Asp Val
            420                 425                 430

Leu Ser Tyr Leu Leu Thr Leu Phe Ala Met His Tyr Phe Val Met Pro
        435                 440                 445

Phe Gln Val Leu Asn Lys Tyr Leu
    450                 455
```

<210> SEQ ID NO 5
<211> LENGTH: 1458
<212> TYPE: DNA
<213> ORGANISM: Phythophtora infestance

<400> SEQUENCE: 5

```
atgcgtgtca ctcgccgcat tcgaagactt gccgaagcgt ggatcgtgtt tcgctatcga      60

gcagcagagc agagcatgga gatactgcgt ggccccgtgg acggcatcgc cctaagcgag     120

aacttccctg ttgatggatt ccgcctcatg gtggcgcttg cgggttgcag cctcatcgca     180

ccgctcatcc acctcacacg cggcgagaca tctcgtcact tgttcaatgt tgcggtggga     240

ctattcgccg gcgtcttcgt gttcgacttg gccgtgttgc acactatcgg gacggccgtt     300

gttgtgtatt tgctcatgat ggtggctcca agcttgtggg gcgcattgtg ctgccgctgc     360

tgttggcgta cctctcacta ttaccgtgaa ttctacagcc cagacattgt gtgggactcg     420
```

```
gcccaaatga tcctaacgct taagctcagc agcgtcgcga tcaactacag tgacggcggg    480

ctgcccacgg agaagaagac gcccacaatg cttaagaacg agctgcaaga aatcccagag    540

ctgatcccgt actttggctt cgttttcttc ttcccgacct acttggctgg tcctgcgttc    600

gagtacaagg actacattta ctggatgaag gacgttcgcg ttgctccttt catggtccat    660

ctccgcaatc tcgtcatttc cgctgctggt ttcttcgtct cgctccaatt ccccgtcgag    720

gaaatcgact cccccgactt cttcccgaaa tcgtcgtggg ctgtgcgctg cctccgtatg    780

tgcatccctg tcgtgttgtt ccgtttccgc tactatctgg cctggtcgct ggccgaggcg    840

gcgagtgctg ctgcgggcgt gggctacgtg caagctactg gaaaatggaa cggcatcacg    900

aacaacgatc tcctgtgtgt ggagcttccg acgaatttcc gagtggccat caacagctgg    960

aacattggag ttgcgcgctg gattaacact tacatttacc agcgcgtcgg tctgaccaag   1020

tctgggaagt ccacgatgct ctccacgatg gcgtcattct ttgtcagcgc tctgtggcat   1080

ggactgtcgc ctggttacta cctgttcttc ctcttgggtg gcatctacat cgaagttggc   1140

aagcaacttc gtcgtcgtct gcgtccatac ttccactaca cggaggaccg taaggctcac   1200

tcgcatgcca ttttcctctc gtactttagc ggcacgtctc atccactggc cttcttgtac   1260

gacatctcgg gcatgttctt cacgtgggtg gcgatgcagt acgctggtgt cgccttcgag   1320

atcctggacg tgcgtcgttg cctcgccatt tggagctcgt ggtacttcct cccgcacctt   1380

gtgagcatcg gcttgctggt tttctttaac ctcttcccgc aacgtcgctc cactcccacc   1440

gacaagaaga cgcagtaa                                                 1458


<210> SEQ ID NO 6
<211> LENGTH: 485
<212> TYPE: PRT
<213> ORGANISM: Phythophtora infestance

<400> SEQUENCE: 6

Met Arg Val Thr Arg Arg Ile Arg Arg Leu Ala Glu Ala Trp Ile Val
1               5                   10                  15

Phe Arg Tyr Arg Ala Ala Glu Gln Ser Met Glu Ile Leu Arg Gly Pro
            20                  25                  30

Val Asp Gly Ile Ala Leu Ser Glu Asn Phe Pro Val Asp Gly Phe Arg
        35                  40                  45

Leu Met Val Ala Leu Ala Gly Cys Ser Leu Ile Ala Pro Leu Ile His
    50                  55                  60

Leu Thr Arg Gly Glu Thr Ser Arg His Leu Phe Asn Val Ala Val Gly
65                  70                  75                  80

Leu Phe Ala Gly Val Phe Val Phe Asp Leu Ala Val Leu His Thr Ile
                85                  90                  95

Gly Thr Ala Val Val Val Tyr Leu Leu Met Met Val Ala Pro Ser Leu
            100                 105                 110

Trp Gly Ala Leu Cys Cys Arg Cys Cys Trp Arg Thr Ser His Tyr Tyr
        115                 120                 125

Arg Glu Phe Tyr Ser Pro Asp Ile Val Trp Asp Ser Ala Gln Met Ile
    130                 135                 140

Leu Thr Leu Lys Leu Ser Ser Val Ala Ile Asn Tyr Ser Asp Gly Gly
145                 150                 155                 160

Leu Pro Thr Glu Lys Lys Thr Pro Thr Met Leu Lys Asn Glu Leu Gln
                165                 170                 175

Glu Ile Pro Glu Leu Ile Pro Tyr Phe Gly Phe Val Phe Phe Phe Pro
            180                 185                 190
```

-continued

Thr Tyr Leu Ala Gly Pro Ala Phe Glu Tyr Lys Asp Tyr Ile Tyr Trp
195 200 205

Met Lys Asp Val Arg Val Ala Pro Phe Met Val His Leu Arg Asn Leu
210 215 220

Val Ile Ser Ala Ala Gly Phe Phe Val Ser Leu Gln Phe Pro Val Glu
225 230 235 240

Glu Ile Asp Ser Pro Asp Phe Phe Pro Lys Ser Ser Trp Ala Val Arg
245 250 255

Cys Leu Arg Met Cys Ile Pro Val Val Leu Phe Arg Phe Arg Tyr Tyr
260 265 270

Leu Ala Trp Ser Leu Ala Glu Ala Ala Ser Ala Ala Ala Gly Val Gly
275 280 285

Tyr Val Gln Ala Thr Gly Lys Trp Asn Gly Ile Thr Asn Asn Asp Leu
290 295 300

Leu Cys Val Glu Leu Pro Thr Asn Phe Arg Val Ala Ile Asn Ser Trp
305 310 315 320

Asn Ile Gly Val Ala Arg Trp Ile Asn Thr Tyr Ile Tyr Gln Arg Val
325 330 335

Gly Leu Thr Lys Ser Gly Lys Ser Thr Met Leu Ser Thr Met Ala Ser
340 345 350

Phe Phe Val Ser Ala Leu Trp His Gly Leu Ser Pro Gly Tyr Tyr Leu
355 360 365

Phe Phe Leu Leu Gly Gly Ile Tyr Ile Glu Val Gly Lys Gln Leu Arg
370 375 380

Arg Arg Leu Arg Pro Tyr Phe His Tyr Thr Glu Asp Arg Lys Ala His
385 390 395 400

Ser His Ala Ile Phe Leu Ser Tyr Phe Ser Gly Thr Ser His Pro Leu
405 410 415

Ala Phe Leu Tyr Asp Ile Ser Gly Met Phe Phe Thr Trp Val Ala Met
420 425 430

Gln Tyr Ala Gly Val Ala Phe Glu Ile Leu Asp Val Arg Arg Cys Leu
435 440 445

Ala Ile Trp Ser Ser Trp Tyr Phe Leu Pro His Leu Val Ser Ile Gly
450 455 460

Leu Leu Val Phe Phe Asn Leu Phe Pro Gln Arg Arg Ser Thr Pro Thr
465 470 475 480

Asp Lys Lys Thr Gln
485

<210> SEQ ID NO 7
<211> LENGTH: 1677
<212> TYPE: DNA
<213> ORGANISM: Phythophtora infestance

<400> SEQUENCE: 7
atgagcacca ccgcgctatt acaagcctcc acttctcctc ctccttcgcg agagccggaa 60
tacgcagcat tggagcagct cgagccgcct ctgtcccatg caatcgacat gggggtcaaa 120
gtctcaccgt ccgagtcagc ggcgatagca ggtggggtct acgtgaccgc ctcgtccagt 180
tgtggggcct ccactatcaa gcacaatccg ttcacgtaca cgacaccggt ggacacgtac 240
gagaaggcca agatgaccat cttgtgtctc ttaggagtcc cattcattcg tttcgtactg 300
ctactctgtg tgggcattct actcgtcatc gtaagtcact tggctctcat tgggtacaaa 360
ccattggacg ctcactctgg agctcgtcca cctctgccac gttggagacg tatcgtcggt 420

```
tcgcctgtgc cgtatctgct acggtcactg atgctcatcg tgggttacta ctgggttcca    480

gtgaaatacc ctccgaattt taatcgtcat gccatgccac gcgtcatcgt aagcaaccat    540

ttgaccttct tcgacggact ctacatcttc acgttgctat cgcccagtat cgccatgaag    600

acggacgtag ctaacctccc attgatcagt cgaatcgtgc agatgattca accgattctg    660

atcgacagag gaacacccga aggacgtaga agagcgatga atgacatcac gtcacatgtt    720

gctgatccca gtaagcctcc gcttcttgta ttcccggaag gcactacatc gaatcaaacg    780

gtactgtgta aattcaaggt cggtgtcttc gtctcaggtg taccgtgtca gccggttgta    840

ctacggtacc cctacaaaca cttcgatttg agttggccac ctggggtttc tgggttgtac    900

ttggcgttac gtgtgttgtg tcaggtgtac aaccgattgg aagtggagat tctaccagcg    960

tactacccgt cggagcgaga acggaaagac cctcaattat acgctattaa tgtgcgtgag   1020

gtaatggcca aagcgctggg agttcccaca acgaaccacg cttttgaaga tgtagccatg   1080

ttgatgcgtg tcggagacta cgccacaaaa cacgtcgtac cactgacaga cgtgggtgaa   1140

gtgatctcgc taacggcact aaagcgaggt gacgtagatc gcctggtggg ctacttccgt   1200

cgccacgacc ttgataagga cggccactta tctatgcagg agctacgtgc actgttccct   1260

aatgacgatc ctgtgatcgt tgatcagctc ttcgacctcg ttgatttaga cgacagtggg   1320

ctcatcgatt tccgggaatt gtgcttggct ctacgtgcac taaacccgca gaatatcaac   1380

gagggagacg acgccttggc gaaattcgct ttccgtctct atgatcttga taacaacgga   1440

gtcatcgacg cctctgaact ggaacaacta cttcgcttcc aacgcaactt ctacggcgtt   1500

tctgaagcga gtgttgcagc cgcgttacgt caagctcagg cagaaaacac gaccggtatc   1560

acttataaca gattcgagca gctggtatta caaaaccccg aagttttgtg gtacgtccgc   1620

gacaaactcg aagtcctacg tggctccatg cgagaaagca gtctcgagat tccgtag      1677
```

<210> SEQ ID NO 8
<211> LENGTH: 558
<212> TYPE: PRT
<213> ORGANISM: Phythophtora infestance

<400> SEQUENCE: 8

```
Met Ser Thr Thr Ala Leu Leu Gln Ala Ser Thr Ser Pro Pro Pro Ser
1               5                   10                  15

Arg Glu Pro Glu Tyr Ala Ala Leu Glu Gln Leu Glu Pro Pro Leu Ser
            20                  25                  30

His Ala Ile Asp Met Gly Val Lys Val Ser Pro Ser Glu Ser Ala Ala
        35                  40                  45

Ile Ala Gly Gly Val Tyr Val Thr Ala Ser Ser Ser Cys Gly Ala Ser
    50                  55                  60

Thr Ile Lys His Asn Pro Phe Thr Tyr Thr Thr Pro Val Asp Thr Tyr
65                  70                  75                  80

Glu Lys Ala Lys Met Thr Ile Leu Cys Leu Leu Gly Val Pro Phe Ile
                85                  90                  95

Arg Phe Val Leu Leu Leu Cys Val Gly Ile Leu Leu Val Ile Val Ser
            100                 105                 110

His Leu Ala Leu Ile Gly Tyr Lys Pro Leu Asp Ala His Ser Gly Ala
        115                 120                 125

Arg Pro Pro Leu Pro Arg Trp Arg Arg Ile Val Gly Ser Pro Val Pro
    130                 135                 140

Tyr Leu Leu Arg Ser Leu Met Leu Ile Val Gly Tyr Tyr Trp Val Pro
```

-continued

```
145                 150                 155                 160

Val Lys Tyr Pro Pro Asn Phe Asn Arg His Ala Met Pro Arg Val Ile
                165                 170                 175

Val Ser Asn His Leu Thr Phe Phe Asp Gly Leu Tyr Ile Phe Thr Leu
            180                 185                 190

Leu Ser Pro Ser Ile Ala Met Lys Thr Asp Val Ala Asn Leu Pro Leu
        195                 200                 205

Ile Ser Arg Ile Val Gln Met Ile Gln Pro Ile Leu Ile Asp Arg Gly
    210                 215                 220

Thr Pro Glu Gly Arg Arg Arg Ala Met Asn Asp Ile Thr Ser His Val
225                 230                 235                 240

Ala Asp Pro Ser Lys Pro Pro Leu Leu Val Phe Pro Glu Gly Thr Thr
                245                 250                 255

Ser Asn Gln Thr Val Leu Cys Lys Phe Lys Val Gly Ser Phe Val Ser
            260                 265                 270

Gly Val Pro Cys Gln Pro Val Val Leu Arg Tyr Pro Tyr Lys His Phe
        275                 280                 285

Asp Leu Ser Trp Pro Pro Gly Val Ser Gly Leu Tyr Leu Ala Leu Arg
    290                 295                 300

Val Leu Cys Gln Val Tyr Asn Arg Leu Glu Val Glu Ile Leu Pro Ala
305                 310                 315                 320

Tyr Tyr Pro Ser Glu Arg Glu Arg Lys Asp Pro Gln Leu Tyr Ala Ile
                325                 330                 335

Asn Val Arg Glu Val Met Ala Lys Ala Leu Gly Val Pro Thr Thr Asn
            340                 345                 350

His Ala Phe Glu Asp Val Ala Met Leu Met Arg Val Gly Asp Tyr Ala
        355                 360                 365

Thr Lys His Val Val Pro Leu Thr Asp Val Gly Glu Val Ile Ser Leu
    370                 375                 380

Thr Ala Leu Lys Arg Gly Asp Val Asp Arg Leu Val Gly Tyr Phe Arg
385                 390                 395                 400

Arg His Asp Leu Asp Lys Asp Gly His Leu Ser Met Gln Glu Leu Arg
                405                 410                 415

Ala Leu Phe Pro Asn Asp Asp Pro Val Ile Val Asp Gln Leu Phe Asp
            420                 425                 430

Leu Val Asp Leu Asp Asp Ser Gly Leu Ile Asp Phe Arg Glu Leu Cys
        435                 440                 445

Leu Ala Leu Arg Ala Leu Asn Pro Gln Asn Ile Asn Glu Gly Asp Asp
    450                 455                 460

Ala Leu Ala Lys Phe Ala Phe Arg Leu Tyr Asp Leu Asp Asn Asn Gly
465                 470                 475                 480

Val Ile Asp Ala Ser Glu Leu Glu Gln Leu Leu Arg Phe Gln Arg Asn
                485                 490                 495

Phe Tyr Gly Val Ser Glu Ala Ser Val Ala Ala Ala Leu Arg Gln Ala
            500                 505                 510

Gln Ala Glu Asn Thr Thr Gly Ile Thr Tyr Asn Arg Phe Glu Gln Leu
        515                 520                 525

Val Leu Gln Asn Pro Glu Val Leu Trp Tyr Val Arg Asp Lys Leu Glu
    530                 535                 540

Val Leu Arg Gly Ser Met Arg Glu Ser Ser Leu Glu Ile Pro
545                 550                 555
```

<210> SEQ ID NO 9

<211> LENGTH: 1047
<212> TYPE: DNA
<213> ORGANISM: Phythophtora infestance

<400> SEQUENCE: 9

```
atggagaagt atagtcggtg gtcggatctg acgacaggca tcaacccgtt cgtgccgcag     60
cgtcggcgct tcacgtccgg atggcccgtg accatcttgc aggtcatatc tggctccgct    120
ttggcgctcg tacgcttccc gttggtgcta gtagccttcg tcgcgctatt tctagtcaac    180
ctagtggtgt ccattctcgc cgtaatcccg ttcctaggac gtctgcttaa gcgcatcaca    240
gaatggttgc tgtgctcact cctcctcctg cttttcggtg tgttcacctc gaacggctca    300
actcgcgttg gatctggcga cgtgctggtt tgcaactaca cgagcttttt ggagatatta    360
tacctggcca cgcgcttctc accagttttt gtatttgcta cagagaccaa gagtaacgac    420
gaaggattgg tacacgtatg tggcctactc gaggcgctgt acaggtcgtt ggcaatgcct    480
gtgagtgttg aacgtgtcaa acccacaagg aagatcgcag acgtagtgcg tcgagctgct    540
gggccagtag tcgtgcttcc cgagggggct agaagcaatg gtaaggctgt gctgaagttc    600
atccccgtgc tacagaacct gccggtcaag acccgcgtac acctcgtggc cttccgctac    660
gagttcaagc gcttcagtcc gagtcaaagt gccggtggtg cctggtctca cctcttctgg    720
actgccttcc acgtgtacca caccatgcgt gtgacggtat tgagtgctaa agacttgaat    780
ctagacgact taacgccgac taaactaccg agtaacaaga gcagtaagaa gcaggagaac    840
tccaagacac tgtcgactga tcaggtcgag aaactacgca cacttctagc cgctatgtta    900
cgcaccaaga ccgttgactt gggaccagag gactctgtgt ctttcaataa ttactggaag    960
cacgtcaaca gcggaggacg tcaaccagcg tcccaattca cggaccgcaa ggctcctcat   1020
gaacacgccc aatgggccaa gagatag                                       1047
```

<210> SEQ ID NO 10
<211> LENGTH: 348
<212> TYPE: PRT
<213> ORGANISM: Phythophtora infestance

<400> SEQUENCE: 10

```
Met Glu Lys Tyr Ser Arg Trp Ser Asp Leu Thr Thr Gly Ile Asn Pro
1               5                   10                  15

Phe Val Pro Gln Arg Arg Arg Phe Thr Ser Gly Trp Pro Val Thr Ile
            20                  25                  30

Leu Gln Val Ile Ser Gly Ser Ala Leu Ala Leu Val Arg Phe Pro Leu
        35                  40                  45

Val Leu Val Ala Phe Val Ala Leu Phe Leu Val Asn Leu Val Val Ser
    50                  55                  60

Ile Leu Ala Val Ile Pro Phe Leu Gly Arg Leu Leu Lys Arg Ile Thr
65                  70                  75                  80

Glu Trp Leu Leu Cys Ser Leu Leu Leu Leu Leu Phe Gly Val Phe Thr
                85                  90                  95

Ser Asn Gly Ser Thr Arg Val Gly Ser Gly Asp Val Leu Val Cys Asn
            100                 105                 110

Tyr Thr Ser Phe Leu Glu Ile Leu Tyr Leu Ala Thr Arg Phe Ser Pro
        115                 120                 125

Val Phe Val Phe Ala Thr Glu Thr Lys Ser Asn Asp Glu Gly Leu Val
    130                 135                 140

His Val Cys Gly Leu Leu Glu Ala Leu Tyr Arg Ser Leu Ala Met Pro
145                 150                 155                 160
```

-continued

```
Val Ser Val Glu Arg Val Lys Pro Thr Arg Lys Ile Ala Asp Val Val
                165                 170                 175

Arg Arg Ala Ala Gly Pro Val Val Val Leu Pro Glu Gly Ala Arg Ser
            180                 185                 190

Asn Gly Lys Ala Val Leu Lys Phe Ile Pro Val Leu Gln Asn Leu Pro
        195                 200                 205

Val Lys Thr Arg Val His Leu Val Ala Phe Arg Tyr Glu Phe Lys Arg
    210                 215                 220

Phe Ser Pro Ser Gln Ser Ala Gly Gly Ala Trp Ser His Leu Phe Trp
225                 230                 235                 240

Thr Ala Phe His Val Tyr His Thr Met Arg Val Thr Val Leu Ser Ala
                245                 250                 255

Lys Asp Leu Asn Leu Asp Asp Leu Thr Pro Thr Lys Leu Pro Ser Asn
            260                 265                 270

Lys Ser Ser Lys Lys Gln Glu Asn Ser Lys Thr Leu Ser Thr Asp Gln
        275                 280                 285

Val Glu Lys Leu Arg Thr Leu Leu Ala Ala Met Leu Arg Thr Lys Thr
    290                 295                 300

Val Asp Leu Gly Pro Glu Asp Ser Val Ser Phe Asn Asn Tyr Trp Lys
305                 310                 315                 320

His Val Asn Ser Gly Gly Arg Gln Pro Ala Ser Gln Phe Thr Asp Arg
                325                 330                 335

Lys Ala Pro His Glu His Ala Gln Trp Ala Lys Arg
            340                 345
```

<210> SEQ ID NO 11
<211> LENGTH: 1275
<212> TYPE: DNA
<213> ORGANISM: Phythophtora infestance

<400> SEQUENCE: 11

```
atgtcgttcg ctacacctgc gcaggtgctg caggatgtgc gcttcgaaga gcgttttgct     60

gagattgagt cgaggttgcc ggccacgttg gctttggcca aggagggatc tttagccaaa    120

cgcaatcaga ccaagcgcaa gctttaccac gacagcgagc tcatccgtat cgagctggaa    180

gagcgtctga atgaactagg tatcgaaagt cagtgggtca ctgccccgga gatgaaggaa    240

gccaatgaga agctggacgc agtgcgtaag cagctcaaac tggacgtgct gcccgccagt    300

tcctctcctc tggagaagat ctacatggtc gtgcgcatgc ttacaatggt gctggtgctc    360

gtgggttggc tcagctgtgt gacagtgctg atcccactca aatggctcaa cccagtactc    420

aagaagatgg gagtcaagaa gaactacctt cccatggaca ttgtgtcatg ggtacggcc    480

ttcatggtct gtgtcacggc ctgtaccgac atgaaggccg agggcgtcga aaacctgctc    540

aaccttaagg actctgtcgt ctgcatgttc agccactcgt ccaacttgga cggcttcatt    600

gtcaatggat catcgccgat tgccttcaag tttgccgcca agaaaagcat tttctagtc    660

ccgttcctcg gctggtcgtc tcgttggggc ttcgactttg tggccatcga ccgctcgcac    720

cgtaaatcag cgctgaagag tttaaaggaa cttgcagtgt cggtaaacga gcatggcaat    780

tcagtctgca tctcgcctga aggcacacgc tcgaaggacg gactgcttca agaattcaag    840

aaggggccat tctacctgcg tgaggacacg aagaagaacg tggtgccctc catcgtgttc    900

ggcgcgtacg agctgtggcc tcctggacga ttgttcagca tccccggaca cacgttggtg    960

cgttacctgc ccgagtacaa gtcagatccg aacttgaacc gtaaccagaa ccggttggcg   1020
```

-continued

```
ctgcgtcgca tctatctcaa ggcgttcacg gaggatgttc cggactacat tggcactcgc   1080

gtgagcacca acttcatcct gaagaacatg ttctatcact atcttgcgtg ggcgatcacg   1140

ttcaaagtga cttcgtgggc actcacagtg atcagcctcg tcttgtactg gctcaacatc   1200

acatatggca cctttatgct gttctcgctg gtcatgatgg tggcgggaga agccctcatg   1260

ttcttcacct gctaa                                                    1275
```

<210> SEQ ID NO 12
<211> LENGTH: 424
<212> TYPE: PRT
<213> ORGANISM: Phythophtora infestance

<400> SEQUENCE: 12

```
Met Ser Phe Ala Thr Pro Ala Gln Val Leu Gln Asp Val Arg Phe Glu
1               5                   10                  15

Glu Arg Phe Ala Glu Ile Glu Ser Arg Leu Pro Ala Thr Leu Ala Leu
            20                  25                  30

Ala Lys Glu Gly Ser Leu Ala Lys Arg Asn Gln Thr Lys Arg Lys Leu
        35                  40                  45

Tyr His Asp Ser Glu Leu Ile Arg Ile Glu Leu Glu Glu Arg Leu Asn
    50                  55                  60

Glu Leu Gly Ile Glu Ser Gln Trp Val Thr Ala Pro Glu Met Lys Glu
65                  70                  75                  80

Ala Asn Glu Lys Leu Asp Ala Val Arg Lys Gln Leu Lys Leu Asp Val
                85                  90                  95

Leu Pro Ala Ser Ser Ser Pro Leu Glu Lys Ile Tyr Met Val Val Arg
            100                 105                 110

Met Leu Thr Met Val Leu Val Leu Val Gly Trp Leu Ser Cys Val Thr
        115                 120                 125

Val Leu Ile Pro Leu Lys Trp Leu Asn Pro Val Leu Lys Lys Met Gly
    130                 135                 140

Val Lys Lys Asn Tyr Leu Pro Met Asp Ile Val Ser Trp Gly Thr Ala
145                 150                 155                 160

Phe Met Val Cys Val Thr Ala Cys Thr Asp Met Lys Ala Glu Gly Val
                165                 170                 175

Glu Asn Leu Leu Asn Leu Lys Asp Ser Val Val Cys Met Phe Ser His
            180                 185                 190

Ser Ser Asn Leu Asp Gly Phe Ile Val Asn Gly Ser Ser Pro Ile Ala
        195                 200                 205

Phe Lys Phe Ala Ala Lys Lys Ser Ile Phe Leu Val Pro Phe Leu Gly
    210                 215                 220

Trp Ser Ser Arg Trp Gly Phe Asp Phe Val Ala Ile Asp Arg Ser His
225                 230                 235                 240

Arg Lys Ser Ala Leu Lys Ser Leu Lys Glu Leu Ala Val Ser Val Asn
                245                 250                 255

Glu His Gly Asn Ser Val Cys Ile Ser Pro Glu Gly Thr Arg Ser Lys
            260                 265                 270

Asp Gly Leu Leu Gln Glu Phe Lys Lys Gly Pro Phe Tyr Leu Arg Glu
        275                 280                 285

Asp Thr Lys Lys Asn Val Val Pro Ser Ile Val Phe Gly Ala Tyr Glu
    290                 295                 300

Leu Trp Pro Pro Gly Arg Leu Phe Ser Ile Pro Gly His Thr Leu Val
305                 310                 315                 320

Arg Tyr Leu Pro Glu Tyr Lys Ser Asp Pro Asn Leu Asn Arg Asn Gln
```

```
            325                 330                 335

Asn Arg Leu Ala Leu Arg Arg Ile Tyr Leu Lys Ala Phe Thr Glu Asp
            340                 345                 350

Val Pro Asp Tyr Ile Gly Thr Arg Val Ser Thr Asn Phe Ile Leu Lys
        355                 360                 365

Asn Met Phe Tyr His Tyr Leu Ala Trp Ala Ile Thr Phe Lys Val Thr
    370                 375                 380

Ser Trp Ala Leu Thr Val Ile Ser Leu Val Leu Tyr Trp Leu Asn Ile
385                 390                 395                 400

Thr Tyr Gly Thr Phe Met Leu Phe Ser Leu Val Met Met Val Ala Gly
                405                 410                 415

Glu Ala Leu Met Phe Phe Thr Cys
            420
```

<210> SEQ ID NO 13
<211> LENGTH: 1278
<212> TYPE: DNA
<213> ORGANISM: Phythophtora infestance

<400> SEQUENCE: 13

```
atgagtcaaa gtgacgagtg ccaagcaacc caaacctccg tgtatccaac caagcgctgc      60
gtgtcaggag gccccgtagt cgagcccgac gctgagccag tgctcaatcg cgtcatccat     120
ccgagtacaa agtttgagac tgcatggacg tggtccggat gcatcatcgg ctgcagctac     180
ctgctccttc tcgtagtatg tgccttcctg aacaccactt tcgtgctgtg gccactgacg     240
ctgctgcaat ggagccacct cctctcaacg cgcagctgcc gatggatatg tcgctttctg     300
gaggataaat acttcgctat gttaagtgga tatttggaac tagttggcgg cgtcaagatt     360
atcatcactg gagacgaaga gctgcagttc gcacaccacg agcacgtgct cttgatctgc     420
aatcatcgca gtgaagtcga ctggatcttc ttctggaatc tggcgctgcg tctcaatgtt     480
catgaccgta ttcgagtcat gatgaagagt gtcattcgat acgcccctgg cgtcggctgg     540
accatgatgc tgctgcgata cccgtacgtt aaccggaact gggccacgga ccaggacaga     600
ttgaccaagg tgattgagtc gtacaaggac gtggacatgg gcacgtggct agccatgttt     660
ccggaaggaa cggcgttgta tgacaagacg ctcaagaaaa gccacgagtt tgctagcaag     720
caaggagaag cgaaatggaa ctacgtgttg cagcccagag tcaagggctt tgagctgtgt     780
atggacaaga tggacccgga ctatgtcgtg gacctcacgg tggcgtatcc ggagctcatg     840
gagggcgtga gaccgtcacc ggtgcgattt gtgagaggac agttcccgac tgaagtacac     900
atgcacgtgc agcggtatca ccggtcaacg ctgctgaagc acaaggaccg catgggtcaa     960
tggctgaaag atcgatttgc agaaaaagag gagcgtcttg aacatttcta cgagactggc    1020
gcgtttcaag gcgaacagca gacgagcggc cagcatgcga gccgtgtcgc tctgttgccc    1080
gcgcaacaga ttctcctctt cgttggtgaa aactacctca cttacttttg gtcgagaaga    1140
cgcctgtctg tatacctgcg tgctttccag gttgctggtg cgtccatcca ctcgatggat    1200
agccacaaga ttcacaacga gaagcaccaa gacaaacttc atactcgatc ggcagatgag    1260
ttgcgcctct tcacgtga                                                  1278
```

<210> SEQ ID NO 14
<211> LENGTH: 425
<212> TYPE: PRT
<213> ORGANISM: Phythophtora infestance

<400> SEQUENCE: 14

-continued

```
Met Ser Gln Ser Asp Glu Cys Gln Ala Thr Gln Thr Ser Val Tyr Pro
1               5                   10                  15

Thr Lys Arg Cys Val Ser Gly Gly Pro Val Val Glu Pro Asp Ala Glu
            20                  25                  30

Pro Val Leu Asn Arg Val Ile His Pro Ser Thr Lys Phe Glu Thr Ala
        35                  40                  45

Trp Thr Trp Ser Gly Cys Ile Ile Gly Cys Ser Tyr Leu Leu Leu Leu
    50                  55                  60

Val Val Cys Ala Phe Leu Asn Thr Thr Phe Val Leu Trp Pro Leu Thr
65                  70                  75                  80

Leu Leu Gln Trp Ser His Leu Leu Ser Thr Arg Ser Cys Arg Trp Ile
                85                  90                  95

Cys Arg Phe Leu Glu Asp Lys Tyr Phe Ala Met Leu Ser Gly Tyr Leu
            100                 105                 110

Glu Leu Val Gly Gly Val Lys Ile Ile Ile Thr Gly Asp Glu Glu Leu
        115                 120                 125

Gln Phe Ala His His Glu His Val Leu Leu Ile Cys Asn His Arg Ser
    130                 135                 140

Glu Val Asp Trp Ile Phe Phe Trp Asn Leu Ala Leu Arg Leu Asn Val
145                 150                 155                 160

His Asp Arg Ile Arg Val Met Met Lys Ser Val Ile Arg Tyr Ala Pro
                165                 170                 175

Gly Val Gly Trp Thr Met Met Leu Leu Arg Tyr Pro Tyr Val Asn Arg
            180                 185                 190

Asn Trp Ala Thr Asp Gln Asp Arg Leu Thr Lys Val Ile Glu Ser Tyr
        195                 200                 205

Lys Asp Val Asp Met Gly Thr Trp Leu Ala Met Phe Pro Glu Gly Thr
    210                 215                 220

Ala Leu Tyr Asp Lys Thr Leu Lys Lys Ser His Glu Phe Ala Ser Lys
225                 230                 235                 240

Gln Gly Glu Ala Lys Trp Asn Tyr Val Leu Gln Pro Arg Val Lys Gly
                245                 250                 255

Phe Glu Leu Cys Met Asp Lys Met Asp Pro Asp Tyr Val Val Asp Leu
            260                 265                 270

Thr Val Ala Tyr Pro Glu Leu Met Glu Gly Val Arg Pro Ser Pro Val
        275                 280                 285

Arg Phe Val Arg Gly Gln Phe Pro Thr Glu Val His Met His Val Gln
    290                 295                 300

Arg Tyr His Arg Ser Thr Leu Leu Lys His Lys Asp Arg Met Gly Gln
305                 310                 315                 320

Trp Leu Lys Asp Arg Phe Ala Glu Lys Glu Glu Arg Leu Glu His Phe
                325                 330                 335

Tyr Glu Thr Gly Ala Phe Gln Gly Glu Gln Gln Thr Ser Gly Gln His
            340                 345                 350

Ala Ser Arg Val Ala Leu Leu Pro Ala Gln Gln Ile Leu Leu Phe Val
        355                 360                 365

Gly Glu Asn Tyr Leu Thr Tyr Phe Trp Ser Arg Arg Arg Leu Ser Val
    370                 375                 380

Tyr Leu Arg Ala Phe Gln Val Ala Gly Ala Ser Ile His Ser Met Asp
385                 390                 395                 400

Ser His Lys Ile His Asn Glu Lys His Gln Asp Lys Leu His Thr Arg
                405                 410                 415
```

-continued

```
Ser Ala Asp Glu Leu Arg Leu Phe Thr
            420                 425


<210> SEQ ID NO 15
<211> LENGTH: 1173
<212> TYPE: DNA
<213> ORGANISM: Phythophtora infestance

<400> SEQUENCE: 15

atggcggtgt tccacctgta ctcggcgctg aatctgctgt ggatcctatg caacagcgcg      60

tgtatcaatt tcctgcaatt ctgtctttgg tgccttgtgc ggccgtttaa caaggcactt     120

tatcgccgac ttatgggctc cgtggcacaa tcactctggg tagacgtcac atccacgagc     180

ttcccacaga ccaagctctc ggtcactggc gagctgccgt cagaccccac gaagcccgtg     240

atcatcatag cgaaccacca agttgacgcg gactggtggt atatttggca ggccgcgcgt     300

caccaacacg cagctgggaa catcaagatc gtgctcaaag accaactcaa gtacctgccc     360

atcatcggct ggggcatgcg cctctttcag ttcctcttcc tacgacgccg catcgaccag     420

gatgcagagc acatcaagaa gtacatgggc ggactcatca gcgataattt cccttttttgg    480

ctcgtgttat tccccgaggg aacgaccatc caccgtgaat acgtggtcaa gtcacaggct     540

tttgcggctc gagaagctcg tcccaagttc gagcgagtgt tgctgccacg cacgaccggg     600

atgcggatca ttctggacgc tgtggcggat gccaaacccg atatttacga cctcactgtg     660

gccttcccgt cgtactcggg tgaagtcccg acgttcgaca tgggatatgg acgcagagtt     720

gacaccgaag tgccgtcgat gaagtcgcta ctggcaggga agcagcctgt gggccgagtg     780

gctttacact caaggaagtt taagtacgag gacgctgcga cagacttgca gggattcttg     840

gatgctcgct ggacggagaa ggaggagcgg atgaactatt tcatcaagca tcagcagttc     900

ccggaaacgg agagcacagt ggagatgcaa ctatcgacct cgatgggagc agttttccgg     960

ctgtggatgg gcatcttgct gtcgtgtgtt gtgcttcccg tcgtcatgat gctcttcttc    1020

ccattgtact tcacgtgggt cgtctactgc ttcgtgtact cggtgtacga ccgcaccacg    1080

aacttctggt ggccgtacat tttcaatctc ttcgtggagc gcgccactaa gacgcacgaa    1140

cactttaagc gtcaccaggc taagtatctg tga                                 1173


<210> SEQ ID NO 16
<211> LENGTH: 390
<212> TYPE: PRT
<213> ORGANISM: Phythophtora infestance

<400> SEQUENCE: 16

Met Ala Val Phe His Leu Tyr Ser Ala Leu Asn Leu Leu Trp Ile Leu
1               5                   10                  15

Cys Asn Ser Ala Cys Ile Asn Phe Leu Gln Phe Cys Leu Trp Cys Leu
            20                  25                  30

Val Arg Pro Phe Asn Lys Ala Leu Tyr Arg Arg Leu Met Gly Ser Val
        35                  40                  45

Ala Gln Ser Leu Trp Val Asp Val Thr Ser Thr Ser Phe Pro Gln Thr
    50                  55                  60

Lys Leu Ser Val Thr Gly Glu Leu Pro Ser Asp Pro Thr Lys Pro Val
65                  70                  75                  80

Ile Ile Ile Ala Asn His Gln Val Asp Ala Asp Trp Trp Tyr Ile Trp
                85                  90                  95

Gln Ala Ala Arg His Gln His Ala Ala Gly Asn Ile Lys Ile Val Leu
            100                 105                 110
```

-continued

```
Lys Asp Gln Leu Lys Tyr Leu Pro Ile Ile Gly Trp Gly Met Arg Leu
        115                 120                 125

Phe Gln Phe Leu Phe Leu Arg Arg Arg Ile Asp Gln Asp Ala Glu His
    130                 135                 140

Ile Lys Lys Tyr Met Gly Gly Leu Ile Ser Asp Asn Phe Pro Phe Trp
145                 150                 155                 160

Leu Val Leu Phe Pro Glu Gly Thr Thr Ile His Arg Glu Tyr Val Val
                165                 170                 175

Lys Ser Gln Ala Phe Ala Ala Arg Glu Ala Arg Pro Lys Phe Glu Arg
            180                 185                 190

Val Leu Leu Pro Arg Thr Thr Gly Met Arg Ile Ile Leu Asp Ala Val
        195                 200                 205

Ala Asp Ala Lys Pro Asp Ile Tyr Asp Leu Thr Val Ala Phe Pro Ser
    210                 215                 220

Tyr Ser Gly Glu Val Pro Thr Phe Asp Met Gly Tyr Gly Arg Arg Val
225                 230                 235                 240

Asp Thr Glu Val Pro Ser Met Lys Ser Leu Leu Ala Gly Lys Gln Pro
                245                 250                 255

Val Gly Arg Val Ala Leu His Ser Arg Lys Phe Lys Tyr Glu Asp Ala
            260                 265                 270

Ala Thr Asp Leu Gln Gly Phe Leu Asp Ala Arg Trp Thr Glu Lys Glu
        275                 280                 285

Glu Arg Met Asn Tyr Phe Ile Lys His Gln Gln Phe Pro Glu Thr Glu
    290                 295                 300

Ser Thr Val Glu Met Gln Leu Ser Thr Ser Met Gly Ala Val Phe Arg
305                 310                 315                 320

Leu Trp Met Gly Ile Leu Leu Ser Cys Val Val Leu Pro Val Val Met
                325                 330                 335

Met Leu Phe Phe Pro Leu Tyr Phe Thr Trp Val Val Tyr Cys Phe Val
            340                 345                 350

Tyr Ser Val Tyr Asp Arg Thr Thr Asn Phe Trp Trp Pro Tyr Ile Phe
        355                 360                 365

Asn Leu Phe Val Glu Arg Ala Thr Lys Thr His Glu His Phe Lys Arg
    370                 375                 380

His Gln Ala Lys Tyr Leu
385                 390
```

<210> SEQ ID NO 17
<211> LENGTH: 1110
<212> TYPE: DNA
<213> ORGANISM: Phythophtora infestance

<400> SEQUENCE: 17

```
atgggcgtgg ctgttgtggg cgtcgtgttc ctgacgtcgc tagtggtcac gggttggaca      60

ggtgtggcct ggatattgac cccatgtttc ttgctggcgg ctctcccact gccggcgttt     120

ctacagacca aacgcttcta tcgccgcgtc actcgcttca tacaatgggc gtggatgggc     180

caagtgaaat tgtttggaat ccaggttcga gtgctcggcg atgcggagac gaaagctcgt     240

gagagcgaat tatcgaagga tcgagcgcta tggctgtcaa accaccgcac tcgtatcgac     300

tggatgctgc tgtggagcgt cgcgtggcgg acgcggacgc tgcatcagtt gcggatcgtc     360

ttgaaggccc cattacggaa aatgcccatc ttcgggtggg ccatgcagca cttcatcttc     420

atctttctgc aacgccgttg ggctgatgac caagtgaatt tgcgcaagtt gttgccattc     480
```

-continued

```
ctcacgtcga cagaaccgga ggcttcctat ctccttttcc ccgaaggcac cgatctgagc    540

gagagtaacc tcgaaaagag tgctgtattt gcagagaaga aaagcctttc acctcgtcag    600

tactcgctgt acccacgcac gacgggttgg acatttatgt tcccactgct gcgctcacaa    660

cttaccgctg tgtacgatgt caccatgttc tacgtggact atgccgctaa cgaacgtcca    720

tcggagtcgt cactgcttac cggtcgtatg ccgcgaatga tccatttcta catcgagcga    780

gtggacatct cggttttgcg tgacaaaagt gagactgact tagcggcctg gttggaaaag    840

cgcttcgaac gtaaggagtc tttgctcaag gccttttacg aggacaacgg caagcttcct    900

catggagccg aacctctctt tcaagagaat caaggtactg cgatggtgat gctggtggcg    960

ttttggctca tatccattgg tgctgccaca ctccttggat tgattggcaa cttcatctcg   1020

gtcattgctg cgctggcggt tgtagttgga tacgccacca acacggcata tgggcctggc   1080

gtggacgggt ttctcataaa caactcgtag                                    1110
```

<210> SEQ ID NO 18
<211> LENGTH: 369
<212> TYPE: PRT
<213> ORGANISM: Phythophtora infestance

<400> SEQUENCE: 18

```
Met Gly Val Ala Val Val Gly Val Val Phe Leu Thr Ser Leu Val Val
1               5                   10                  15

Thr Gly Trp Thr Gly Val Ala Trp Ile Leu Thr Pro Cys Phe Leu Leu
            20                  25                  30

Ala Ala Leu Pro Leu Pro Ala Phe Leu Gln Thr Lys Arg Phe Tyr Arg
        35                  40                  45

Arg Val Thr Arg Phe Ile Gln Trp Ala Trp Met Gly Gln Val Lys Leu
    50                  55                  60

Phe Gly Ile Gln Val Arg Val Leu Gly Asp Ala Glu Thr Lys Ala Arg
65                  70                  75                  80

Glu Ser Glu Leu Ser Lys Asp Arg Ala Leu Trp Leu Ser Asn His Arg
                85                  90                  95

Thr Arg Ile Asp Trp Met Leu Leu Trp Ser Val Ala Trp Arg Thr Arg
            100                 105                 110

Thr Leu His Gln Leu Arg Ile Val Leu Lys Ala Pro Leu Arg Lys Met
        115                 120                 125

Pro Ile Phe Gly Trp Ala Met Gln His Phe Ile Phe Ile Phe Leu Gln
    130                 135                 140

Arg Arg Trp Ala Asp Asp Gln Val Asn Leu Arg Lys Leu Leu Pro Phe
145                 150                 155                 160

Leu Thr Ser Thr Glu Pro Glu Ala Ser Tyr Leu Leu Phe Pro Glu Gly
                165                 170                 175

Thr Asp Leu Ser Glu Ser Asn Leu Glu Lys Ser Ala Val Phe Ala Glu
            180                 185                 190

Lys Lys Ser Leu Ser Pro Arg Gln Tyr Ser Leu Tyr Pro Arg Thr Thr
        195                 200                 205

Gly Trp Thr Phe Met Phe Pro Leu Leu Arg Ser Gln Leu Thr Ala Val
    210                 215                 220

Tyr Asp Val Thr Met Phe Tyr Val Asp Tyr Ala Ala Asn Glu Arg Pro
225                 230                 235                 240

Ser Glu Ser Ser Leu Leu Thr Gly Arg Met Pro Arg Met Ile His Phe
                245                 250                 255

Tyr Ile Glu Arg Val Asp Ile Ser Val Leu Arg Asp Lys Ser Glu Thr
```

-continued

```
            260                 265                 270

Asp Leu Ala Ala Trp Leu Glu Lys Arg Phe Glu Arg Lys Glu Ser Leu
        275                 280                 285

Leu Lys Ala Phe Tyr Glu Asp Asn Gly Lys Leu Pro His Gly Ala Glu
    290                 295                 300

Pro Leu Phe Gln Glu Asn Gln Gly Thr Ala Met Val Met Leu Val Ala
305                 310                 315                 320

Phe Trp Leu Ile Ser Ile Gly Ala Ala Thr Leu Leu Gly Leu Ile Gly
                325                 330                 335

Asn Phe Ile Ser Val Ile Ala Ala Leu Ala Val Val Val Gly Tyr Ala
            340                 345                 350

Thr Asn Thr Ala Tyr Gly Pro Gly Val Asp Gly Phe Leu Ile Asn Asn
        355                 360                 365

Ser


<210> SEQ ID NO 19
<211> LENGTH: 1344
<212> TYPE: DNA
<213> ORGANISM: Phythophtora infestance

<400> SEQUENCE: 19

atgggacccc gagtggaacc tccaaacagc gggcgctcgc ccacagcgag caagaggcgc      60

atgaagaagt tccgtgacgt tgtgtccccg ttggacccgg cggatgcgcg ctccggtgtg     120

cacagctccg agttccgcgg cttgtacaac ctggcgatgc tgtctggggt gctctacgtg     180

ttcacgacgc tcttcacgaa cctgctaatg acgaacgaac ccatcgactc gaagcttctg     240

ctgtcggtgt tttactcgac gcatttactc gaggtattgg ctacattcgt gtgtcaagct     300

ctgtatgcct acacggccct gatcccagtg tacatggcgg gcacggacaa gccgaaccgc     360

ctgctcatca acatcgtgca ccacacgctt caaagtctgc tcttcttctt cacaatcgtc     420

ttcatcgtct ggcgcgactg gaacctcatc cacgccgtgt cagcgttcat tgaaggtctc     480

gtactattga tgaagatgca ctcctacatc cgcaccaagc tggagatctc acgcactgag     540

aacaaaccgc ccattcctga catcaaggac tttactatgt atttactgat cccgtcgctg     600

gtgtacgaac ctaacttccc acgtacctgt cggattcgct gggcttacct tgctgagaag     660

actttctcgg ttatcatggg gatttcgatg ctatacatca tcgtcacgac ccatgtgatg     720

cctcgcctgg aggattccgg gactgtgaac cctgtgctat cggtcgtgag tcttctgctc     780

cctttcctgg gatgctactt gctcacatgg ttcatcatct ttgagtgcat ctgcaatggc     840

ttcgctgaag tgacttactc agccgaccgg gacttttatg gtgactggtg gaacagcaca     900

acgttcgacg agtttgcgcg caagtggaac aaaccggtgc atgagtttct actacgacat     960

gtatacttgg agacgttgga ctcgtacaag atctcgaaga cttacgccac tatgttcacc    1020

ttcttcatgt ctgctgcact ccacgaatgc gtcttcatcc tcatgttccg cacagtcaga    1080

atgtacttct ttactcttca gatggtccag ttggttacca tcgtgtacgg acgtggcttg    1140

cgtggctcgc ggatgggaaa tatcaccttc tggctcggta tgatcctcgg actcccactt    1200

caagctgtca tttacagtcg cgaatatcac ggtggtgagc ccatctttat ggtcatcatg    1260

atgccagcaa tgatcttcgg gttcggtgga gttctcgttg cttcactgat gcatctaagt    1320

cgtttgagga agaaacaagc ctaa                                           1344


<210> SEQ ID NO 20
<211> LENGTH: 447
```

<212> TYPE: PRT
<213> ORGANISM: Phythophtora infestance

<400> SEQUENCE: 20

```
Met Gly Pro Arg Val Glu Pro Pro Asn Ser Gly Arg Ser Pro Thr Ala
1               5                   10                  15

Ser Lys Arg Arg Met Lys Lys Phe Arg Asp Val Val Ser Pro Leu Asp
            20                  25                  30

Pro Ala Asp Ala Arg Ser Gly Val His Ser Ser Glu Phe Arg Gly Leu
        35                  40                  45

Tyr Asn Leu Ala Met Leu Ser Gly Val Leu Tyr Val Phe Thr Thr Leu
    50                  55                  60

Phe Thr Asn Leu Leu Met Thr Asn Glu Pro Ile Asp Ser Lys Leu Leu
65                  70                  75                  80

Leu Ser Val Phe Tyr Ser Thr His Leu Leu Glu Val Leu Ala Thr Phe
                85                  90                  95

Val Cys Gln Ala Leu Tyr Ala Tyr Thr Ala Leu Ile Pro Val Tyr Met
            100                 105                 110

Ala Gly Thr Asp Lys Pro Asn Arg Leu Leu Ile Asn Ile Val His His
        115                 120                 125

Thr Leu Gln Ser Leu Leu Phe Phe Phe Thr Ile Val Phe Ile Val Trp
    130                 135                 140

Arg Asp Trp Asn Leu Ile His Ala Val Ser Ala Phe Ile Glu Gly Leu
145                 150                 155                 160

Val Leu Leu Met Lys Met His Ser Tyr Ile Arg Thr Lys Leu Glu Ile
                165                 170                 175

Ser Arg Thr Glu Asn Lys Pro Pro Ile Pro Asp Ile Lys Asp Phe Thr
            180                 185                 190

Met Tyr Leu Leu Ile Pro Ser Leu Val Tyr Glu Pro Asn Phe Pro Arg
        195                 200                 205

Thr Cys Arg Ile Arg Trp Ala Tyr Leu Ala Glu Lys Thr Phe Ser Val
    210                 215                 220

Ile Met Gly Ile Ser Met Leu Tyr Ile Ile Val Thr Thr His Val Met
225                 230                 235                 240

Pro Arg Leu Glu Asp Ser Gly Thr Val Asn Pro Val Leu Ser Val Val
                245                 250                 255

Ser Leu Leu Leu Pro Phe Leu Gly Cys Tyr Leu Leu Thr Trp Phe Ile
            260                 265                 270

Ile Phe Glu Cys Ile Cys Asn Gly Phe Ala Glu Val Thr Tyr Ser Ala
        275                 280                 285

Asp Arg Asp Phe Tyr Gly Asp Trp Trp Asn Ser Thr Thr Phe Asp Glu
    290                 295                 300

Phe Ala Arg Lys Trp Asn Lys Pro Val His Glu Phe Leu Leu Arg His
305                 310                 315                 320

Val Tyr Leu Glu Thr Leu Asp Ser Tyr Lys Ile Ser Lys Thr Tyr Ala
                325                 330                 335

Thr Met Phe Thr Phe Phe Met Ser Ala Ala Leu His Glu Cys Val Phe
            340                 345                 350

Ile Leu Met Phe Arg Thr Val Arg Met Tyr Phe Phe Thr Leu Gln Met
        355                 360                 365

Val Gln Leu Val Thr Ile Val Tyr Gly Arg Gly Leu Arg Gly Ser Arg
    370                 375                 380

Met Gly Asn Ile Thr Phe Trp Leu Gly Met Ile Leu Gly Leu Pro Leu
385                 390                 395                 400
```

Gln Ala Val Ile Tyr Ser Arg Glu Tyr His Gly Gly Glu Pro Ile Phe
405 410 415

Met Val Ile Met Met Pro Ala Met Ile Phe Gly Phe Gly Gly Val Leu
420 425 430

Val Ala Ser Leu Met His Leu Ser Arg Leu Arg Lys Lys Gln Ala
435 440 445

<210> SEQ ID NO 21
<211> LENGTH: 927
<212> TYPE: DNA
<213> ORGANISM: Phythophtora infestance

<400> SEQUENCE: 21
atgacaggcc agcaacacac ttggctgctt ggtgtcggcc tcgcagtggc gacaatctcc 60
ctttgcgtcg ccattcatgc aagcgcctta ataacgattg caactgcatg tgtagctgct 120
tatctccctt catacttgga cggctcagag tacacggggg agcgctactg gccatggttt 180
gccaccttca tcggacacgg catggcgcac attccgggga cgctggaatt cgaggagccc 240
attgacgcct ccaagcaaca catcttttgt tcgcatccac atggactgct ttccacccac 300
cacggacttc tcatgtctgg gcagactgtt cctccattct acgagacggt accgctgtct 360
acacgacgcc acttggctgc gtccgtttgt ttccggatac cattctaccg tgaatatgta 420
ctctggtctg gatgtgttga tgcacgccgt agtgtggcgg aaaagatgct tcgaaatggc 480
aagagtctgg tgatcttagt cgggggtatt gcggagcaga tgctctctca gcgtggagac 540
cacacgatct acgtcaaaaa gcgcaagggg cacattcgct tagcactgaa atacggggta 600
cccatcgttc ccggctacgc gtttggagag accgacctgt tcacccactc aagtgtgctg 660
ttgtcgttcc gccaaacgat tgcgaagaag ttttctgtgg cgttgctgct tggacgtgga 720
tactccaagt ggttgttttg gctacctcat aaaggagtga ccatcaacca ggtctttggc 780
aaacccattc cagtcttgaa gaaggacgac ccgagttcgg acgacatcga aaagctgcat 840
caccagtacg agcgcgagct agtgcgcatt tttgacaagt acaaggagaa acatggatac 900
ggaaactgta cgctgcatgt gcgctag 927

<210> SEQ ID NO 22
<211> LENGTH: 308
<212> TYPE: PRT
<213> ORGANISM: Phythophtora infestance

<400> SEQUENCE: 22

Met Thr Gly Gln Gln His Thr Trp Leu Leu Gly Val Gly Leu Ala Val
1 5 10 15

Ala Thr Ile Ser Leu Cys Val Ala Ile His Ala Ser Ala Leu Ile Thr
20 25 30

Ile Ala Thr Ala Cys Val Ala Ala Tyr Leu Pro Ser Tyr Leu Asp Gly
35 40 45

Ser Glu Tyr Thr Gly Glu Arg Tyr Trp Pro Trp Phe Ala Thr Phe Ile
50 55 60

Gly His Gly Met Ala His Ile Pro Gly Thr Leu Glu Phe Glu Glu Pro
65 70 75 80

Ile Asp Ala Ser Lys Gln His Ile Phe Cys Ser His Pro His Gly Leu
85 90 95

Leu Ser Thr His His Gly Leu Leu Met Ser Gly Gln Thr Val Pro Pro
100 105 110

```
Phe Tyr Glu Thr Val Pro Leu Ser Thr Arg Arg His Leu Ala Ala Ser
        115                 120                 125

Val Cys Phe Arg Ile Pro Phe Tyr Arg Glu Tyr Val Leu Trp Ser Gly
    130                 135                 140

Cys Val Asp Ala Arg Arg Ser Val Ala Glu Lys Met Leu Arg Asn Gly
145                 150                 155                 160

Lys Ser Leu Val Ile Leu Val Gly Gly Ile Ala Glu Gln Met Leu Ser
                165                 170                 175

Gln Arg Gly Asp His Thr Ile Tyr Val Lys Lys Arg Lys Gly His Ile
            180                 185                 190

Arg Leu Ala Leu Lys Tyr Gly Val Pro Ile Val Pro Gly Tyr Ala Phe
        195                 200                 205

Gly Glu Thr Asp Leu Phe Thr His Ser Ser Val Leu Leu Ser Phe Arg
    210                 215                 220

Gln Thr Ile Ala Lys Lys Phe Ser Val Ala Leu Leu Leu Gly Arg Gly
225                 230                 235                 240

Tyr Ser Lys Trp Leu Phe Trp Leu Pro His Lys Gly Val Thr Ile Asn
                245                 250                 255

Gln Val Phe Gly Lys Pro Ile Pro Val Leu Lys Lys Asp Asp Pro Ser
            260                 265                 270

Ser Asp Asp Ile Glu Lys Leu His His Gln Tyr Glu Arg Glu Leu Val
        275                 280                 285

Arg Ile Phe Asp Lys Tyr Lys Glu Lys His Gly Tyr Gly Asn Cys Thr
    290                 295                 300

Leu His Val Arg
305
```

<210> SEQ ID NO 23
<211> LENGTH: 1179
<212> TYPE: DNA
<213> ORGANISM: Phythophtora infestance

<400> SEQUENCE: 23

```
atgtcggcag cccaagtgct caacaatgct gcttacggcc gcacatcggc gtggcctgat     60

tcgaataccc gtccggatct gcagacacta cgaggacgct ttctacgacg acttcatctt    120

tcgcttattt atggtctctg ggtgcttggt acgcttttca atgcagcgat gtgggttttc    180

tcgctcgtct gtgtagctca gtgggtttgg agtaccctca tcggtgctaa tgaagctccg    240

attccacttg ccgtgcaagt atttctaagt ctcgtcgcac tctatgagag ttaccatttc    300

gtgactcggc cttcgcatca cccctggcca ttcatgcggc gcttgattcg ctactcgctc    360

cttcactacc cgtacttccg cctcaatgcc acggtcttcg acgagcgcga gcgggccaag    420

caattaagtc aagatggtgc taccaatgac actagcgctt tcaacacgga gatcgctagc    480

aagaccatcg tggagaacga tatttctcca tttgtgaaac ccaacgagag cgccatgttt    540

gcttttcatc cgcacagcgt tctctccaat ggctgggtag ccaatggcgc gaatcacatg    600

agtttcgaac aagctgactg tcgatggctc gtagctgaaa atctctttgg ggtccccctc    660

atgagagact tgctaaactg gatggacttt agtagcgttg ccaagtcaac gttccaacag    720

cgtatgtctg cccgtcaaaa tgtgtgtttg atccctggtg gcttcgaaga agcaacactc    780

tacgaacgag gcaaacatcg tgtgtacatc aagaaacgct ttggcttcat caagctggct    840

ttgcagtatg ggtacaaggt gcacccagtg tacacgttcg gggaggagta cgcttatcac    900

acctttcctt atctgctcaa gttgcgtctc aagctgaacg agttcaagat tcctggagta    960
```

-continued

```
tttttcttcg gtcttccgca ttgtttcttt ctgcctcgca ccgacgtgga ccttatcact   1020

gtcgttggag aacccttggt cctaccgcgt atcgaacaac cgaccaagga agacgtgcag   1080

aaatatcaag gtcagtacgt cgaggctctg caaaagctgt tcaacaagta caagtctgtg   1140

tacgccgtcg atccgcaagc gcagttggaa atatactaa                          1179


<210> SEQ ID NO 24
<211> LENGTH: 392
<212> TYPE: PRT
<213> ORGANISM: Phythophtora infestance

<400> SEQUENCE: 24

Met Ser Ala Ala Gln Val Leu Asn Asn Ala Ala Tyr Gly Arg Thr Ser
1               5                   10                  15

Ala Trp Pro Asp Ser Asn Thr Arg Pro Asp Leu Gln Thr Leu Arg Gly
            20                  25                  30

Arg Phe Leu Arg Arg Leu His Leu Ser Leu Ile Tyr Gly Leu Trp Val
        35                  40                  45

Leu Gly Thr Leu Phe Asn Ala Ala Met Trp Val Phe Ser Leu Val Cys
    50                  55                  60

Val Ala Gln Trp Val Trp Ser Thr Leu Ile Gly Ala Asn Glu Ala Pro
65                  70                  75                  80

Ile Pro Leu Ala Val Gln Val Phe Leu Ser Leu Val Ala Leu Tyr Glu
                85                  90                  95

Ser Tyr His Phe Val Thr Arg Pro Ser His His Pro Trp Pro Phe Met
            100                 105                 110

Arg Arg Leu Ile Arg Tyr Ser Leu Leu His Tyr Pro Tyr Phe Arg Leu
        115                 120                 125

Asn Ala Thr Val Phe Asp Glu Arg Glu Arg Ala Lys Gln Leu Ser Gln
    130                 135                 140

Asp Gly Ala Thr Asn Asp Thr Ser Ala Phe Asn Thr Glu Ile Ala Ser
145                 150                 155                 160

Lys Thr Ile Val Glu Asn Asp Ile Ser Pro Phe Val Lys Pro Asn Glu
                165                 170                 175

Ser Ala Met Phe Ala Phe His Pro His Ser Val Leu Ser Asn Gly Trp
            180                 185                 190

Val Ala Asn Gly Ala Asn His Met Ser Phe Glu Gln Ala Asp Cys Arg
        195                 200                 205

Trp Leu Val Ala Glu Asn Leu Phe Gly Val Pro Leu Met Arg Asp Leu
    210                 215                 220

Leu Asn Trp Met Asp Phe Ser Ser Val Ala Lys Ser Thr Phe Gln Gln
225                 230                 235                 240

Arg Met Ser Ala Arg Gln Asn Val Cys Leu Ile Pro Gly Gly Phe Glu
                245                 250                 255

Glu Ala Thr Leu Tyr Glu Arg Gly Lys His Arg Val Tyr Ile Lys Lys
            260                 265                 270

Arg Phe Gly Phe Ile Lys Leu Ala Leu Gln Tyr Gly Tyr Lys Val His
        275                 280                 285

Pro Val Tyr Thr Phe Gly Glu Glu Tyr Ala Tyr His Thr Phe Pro Tyr
    290                 295                 300

Leu Leu Lys Leu Arg Leu Lys Leu Asn Glu Phe Lys Ile Pro Gly Val
305                 310                 315                 320

Phe Phe Phe Gly Leu Pro His Cys Phe Phe Leu Pro Arg Thr Asp Val
                325                 330                 335
```

```
Asp Leu Ile Thr Val Val Gly Glu Pro Leu Val Leu Pro Arg Ile Glu
            340                 345                 350

Gln Pro Thr Lys Glu Asp Val Gln Lys Tyr Gln Gly Gln Tyr Val Glu
        355                 360                 365

Ala Leu Gln Lys Leu Phe Asn Lys Tyr Lys Ser Val Tyr Ala Val Asp
    370                 375                 380

Pro Gln Ala Gln Leu Glu Ile Tyr
385                 390


<210> SEQ ID NO 25
<211> LENGTH: 1146
<212> TYPE: DNA
<213> ORGANISM: Phythophtora infestance

<400> SEQUENCE: 25

atggcgaagc tcacgaatgc ggcttgcggt cgcacatctg cgtggccgga ctttgatact      60

cgcccagagt tgcgaacgct acgagggcga ttcatgcgac gcttcgatct cttcattctc     120

tacggtctct gggtcgtcgg cctcctgttt ctcgcagtaa tgtgggtctt ctcactcttc     180

tgtttggtgc aatggagttg gagacgagct acacacgacc atgctcctcc gatggcattt     240

tcagcccaga tatacctggg tttcatcgtg ctgcacgaaa gctaccacta cctcacaaaa     300

ccttcgttgc atcagtggcc atttatgaga cgtttttttc gacaagtttt tcttcattac     360

ccatacttcc gcctcaacgt cttggttttt gaagagcgtt cgaaaacttc aagtgaaaat     420

ggcaaatgca acaaagaaat tgccagcaag gccgttgaag agaacaatct gtcgccattc     480

gtgacccccg atgatcgcgc tctatttgcc ttccatccgc acggtgtcct ctccagtgga     540

ttcgccttca acggcgcgca ccacatggga ttcttgcatg cccattgtcg ctggctcgta     600

tcggagaatc tcttctggtt ccccgtcatg cgcgacctgt tgaactggat ggacttcagt     660

tgcgtatctc gatcgacttt ccatcgtttc atggccacag gtcaaaatgt gtgtttgatc     720

cctggcggct tcgaagacgc aacactctac gaacgaggca aacatcgtgt gtacatcaag     780

aaacgctttg gctttatcaa gttggctttg cagtatgggt acaaggtgca cccagtgtac     840

acgttcgggg aggagtacgc ttatcacacc tttccttatc tgctcaagtt gcgtctcaag     900

ctgaacgagt tcaagattcc tggagtcttt ttcttcggtc ttccgcattg tttctttctg     960

cctcgcaccg acgtggacct tatcactgtc gttggagaac ccttggtcct gccgcgtatc    1020

gaacaaccga ccaaggaaga cgtgcagaaa taccatggtc agtacgtcga ggctctgcaa    1080

aagctgttca acaagtacaa gtctgtgtac gcagtcgacc cagacgctga acttgaatta    1140

tactga                                                               1146


<210> SEQ ID NO 26
<211> LENGTH: 381
<212> TYPE: PRT
<213> ORGANISM: Phythophtora infestance

<400> SEQUENCE: 26

Met Ala Lys Leu Thr Asn Ala Ala Cys Gly Arg Thr Ser Ala Trp Pro
1               5                   10                  15

Asp Phe Asp Thr Arg Pro Glu Leu Arg Thr Leu Arg Gly Arg Phe Met
            20                  25                  30

Arg Arg Phe Asp Leu Phe Ile Leu Tyr Gly Leu Trp Val Val Gly Leu
        35                  40                  45

Leu Phe Leu Ala Val Met Trp Val Phe Ser Leu Phe Cys Leu Val Gln
    50                  55                  60
```

```
Trp Ser Trp Arg Arg Ala Thr His Asp His Ala Pro Pro Met Ala Phe
65                  70                  75                  80

Ser Ala Gln Ile Tyr Leu Gly Phe Ile Val Leu His Glu Ser Tyr His
                85                  90                  95

Tyr Leu Thr Lys Pro Ser Leu His Gln Trp Pro Phe Met Arg Arg Phe
            100                 105                 110

Phe Arg Gln Val Phe Leu His Tyr Pro Tyr Phe Arg Leu Asn Val Leu
        115                 120                 125

Val Phe Glu Glu Arg Ser Lys Thr Ser Ser Glu Asn Gly Lys Cys Asn
    130                 135                 140

Lys Glu Ile Ala Ser Lys Ala Val Glu Glu Asn Asn Leu Ser Pro Phe
145                 150                 155                 160

Val Thr Pro Asp Asp Arg Ala Leu Phe Ala Phe His Pro His Gly Val
                165                 170                 175

Leu Ser Ser Gly Phe Ala Phe Asn Gly Ala His His Met Gly Phe Leu
            180                 185                 190

His Ala His Cys Arg Trp Leu Val Ser Glu Asn Leu Phe Trp Phe Pro
        195                 200                 205

Val Met Arg Asp Leu Leu Asn Trp Met Asp Phe Ser Cys Val Ser Arg
    210                 215                 220

Ser Thr Phe His Arg Phe Met Ala Thr Gly Gln Asn Val Cys Leu Ile
225                 230                 235                 240

Pro Gly Gly Phe Glu Asp Ala Thr Leu Tyr Glu Arg Gly Lys His Arg
                245                 250                 255

Val Tyr Ile Lys Lys Arg Phe Gly Phe Ile Lys Leu Ala Leu Gln Tyr
            260                 265                 270

Gly Tyr Lys Val His Pro Val Tyr Thr Phe Gly Glu Glu Tyr Ala Tyr
        275                 280                 285

His Thr Phe Pro Tyr Leu Leu Lys Leu Arg Leu Lys Leu Asn Glu Phe
    290                 295                 300

Lys Ile Pro Gly Val Phe Phe Phe Gly Leu Pro His Cys Phe Phe Leu
305                 310                 315                 320

Pro Arg Thr Asp Val Asp Leu Ile Thr Val Val Gly Glu Pro Leu Val
                325                 330                 335

Leu Pro Arg Ile Glu Gln Pro Thr Lys Glu Asp Val Gln Lys Tyr His
            340                 345                 350

Gly Gln Tyr Val Glu Ala Leu Gln Lys Leu Phe Asn Lys Tyr Lys Ser
        355                 360                 365

Val Tyr Ala Val Asp Pro Asp Ala Glu Leu Glu Leu Tyr
    370                 375                 380
```

<210> SEQ ID NO 27
<211> LENGTH: 852
<212> TYPE: DNA
<213> ORGANISM: Phythophtora infestance

<400> SEQUENCE: 27

```
atggaggctt tcgtcccagt gctgctcctc actatcacag cttacatgta cgagttcacg      60

tatcgcggac acccgcacca aacgggctgt agagagcgtc ttgattggat atatggtcac     120

agctttctca ttgagaccgt caagcggtac tttagcgaaa agataattcg catggcaccc     180

ctggatccca agaagcaata tgtactgggc tttcatccac acggcatcac accgacctca     240

gttatgtggc tccagttcag cgcagaatgg cgaaggttgt tcccgaactt ctacgcgcac     300
```

-continued

```
attttaactg ccggcattat gcatgcactg ccacttgctc gggacatcct tcagttcttg    360

gggtcacgag aagttacccg acaagccttc acatatactc ttcagcacaa cgagagtgtg    420

ttgctggtgc cgggtggcca agccgagatg ttagagcagc gatctggtca gaaggaggtt    480

cgggtgtaca cacatcacaa aggtttcatc cgcctcgcaa tcgagcatgg agtaccgttg    540

gtccccgtcc tcagcttcaa cgagggcgag atgctggaca acatccaggc tcccatgctc    600

cagcgctggt tcgttataaa gctcgcgttc ccattcccat tttcccccta cggtcgtgca    660

ttgctgccga tcccgcgcaa agtacaaatt cctatcgtgg tgggagcacc tctggaggtg    720

ccacacatga agaaacccag ccatgaagat atcgataaag tccacgccag atactttgat    780

gagcttcgtg acatgttcgc aaagtacaag gatgaagctg gatgcggcga ctacaagctc    840

atttacgtct ga                                                        852
```

<210> SEQ ID NO 28
<211> LENGTH: 283
<212> TYPE: PRT
<213> ORGANISM: Phythophtora infestance

<400> SEQUENCE: 28

```
Met Glu Ala Phe Val Pro Val Leu Leu Leu Thr Ile Thr Ala Tyr Met
1               5                   10                  15

Tyr Glu Phe Thr Tyr Arg Gly His Pro His Gln Thr Gly Cys Arg Glu
            20                  25                  30

Arg Leu Asp Trp Ile Tyr Gly His Ser Phe Leu Ile Glu Thr Val Lys
        35                  40                  45

Arg Tyr Phe Ser Glu Lys Ile Ile Arg Met Ala Pro Leu Asp Pro Lys
    50                  55                  60

Lys Gln Tyr Val Leu Gly Phe His Pro His Gly Ile Thr Pro Thr Ser
65                  70                  75                  80

Val Met Trp Leu Gln Phe Ser Ala Glu Trp Arg Arg Leu Phe Pro Asn
                85                  90                  95

Phe Tyr Ala His Ile Leu Thr Ala Gly Ile Met His Ala Leu Pro Leu
            100                 105                 110

Ala Arg Asp Ile Leu Gln Phe Leu Gly Ser Arg Glu Val Thr Arg Gln
        115                 120                 125

Ala Phe Thr Tyr Thr Leu Gln His Asn Glu Ser Val Leu Leu Val Pro
    130                 135                 140

Gly Gly Gln Ala Glu Met Leu Glu Gln Arg Ser Gly Gln Lys Glu Val
145                 150                 155                 160

Arg Val Tyr Thr His His Lys Gly Phe Ile Arg Leu Ala Ile Glu His
                165                 170                 175

Gly Val Pro Leu Val Pro Val Leu Ser Phe Asn Glu Gly Glu Met Leu
            180                 185                 190

Asp Asn Ile Gln Ala Pro Met Leu Gln Arg Trp Phe Val Ile Lys Leu
        195                 200                 205

Ala Phe Pro Phe Pro Phe Phe Pro Tyr Gly Arg Ala Leu Leu Pro Ile
    210                 215                 220

Pro Arg Lys Val Gln Ile Pro Ile Val Val Gly Ala Pro Leu Glu Val
225                 230                 235                 240

Pro His Met Lys Lys Pro Ser His Glu Asp Ile Asp Lys Val His Ala
                245                 250                 255

Arg Tyr Phe Asp Glu Leu Arg Asp Met Phe Ala Lys Tyr Lys Asp Glu
            260                 265                 270
```

Ala Gly Cys Gly Asp Tyr Lys Leu Ile Tyr Val
275 280

<210> SEQ ID NO 29
<211> LENGTH: 1050
<212> TYPE: DNA
<213> ORGANISM: Phythophtora infestance

<400> SEQUENCE: 29
atggcgagcg aaactcaggc tgatcctgtc cagacagaca agggcctctt tgtctatgag 60
cctcttggat tcttcgcgga tgatagcaaa gtacccaagt ggatgcagct cctaattact 120
gacgtgttta gcttcgtgac tacgcactac ttcgtgtgga gcttgccatt cctcgcgctg 180
ttctgctacc tacaccagca cgaactcgac tacgtatcgg tcgctatgat tgctctgtat 240
ctgccctcat tcttcagtgg ggcgcagaag acagggaagg gcaacgagtg ggaagccgcg 300
cggacgtcga gtttatgggg cctcatgaac aaatttcttc gcgtcaagat tattcgggag 360
caagagctgg atccgaagaa gaagttcatt ttcggattcc accctcacgg aatcctcgta 420
ctctctcgaa tcgcaggctt cggtcgaaac ttcattgacg tgtgtccggg catcacgact 480
cggttccttg gagcctcggc aatgtattat attccgctag gacgtgaaat gtgtctgtgg 540
atgggtggag tcgatgcctc acgctccaca ggtgaaaagg tgctgaaaga aggcaacagc 600
atcatcgtct accctggcgg cgtacccgag attttcctca cggatccgaa tttaaaggag 660
acccagctcg tgctgaaaaa gcgtctcggg tttatcaagc tcgccatgcg tcagggcgca 720
cagctcgtcc cgacgttcgt ctttggtgaa aagtggctgt acaacatgtg gaccccgccc 780
gaaagtgtga ctaacttttt ccgcaagaca ctcggcatcc ctgttctggt cttctggggg 840
aaattctggt ggatgcccaa ggctccaggc gaaggaaaac gctacggact tgtgtacggg 900
aagcctattg cgacgaagca cgattcaaac ccgagcgacg aagaaatccg tgctgttcat 960
gccgaatacg ttagcgaaat cgagcgcatc ttcagccagt acaaatcgga attcggctac 1020
gacgaggacg agacgctggc catcatttag 1050

<210> SEQ ID NO 30
<211> LENGTH: 349
<212> TYPE: PRT
<213> ORGANISM: Phythophtora infestance

<400> SEQUENCE: 30

Met Ala Ser Glu Thr Gln Ala Asp Pro Val Gln Thr Asp Lys Gly Leu
1 5 10 15

Phe Val Tyr Glu Pro Leu Gly Phe Phe Ala Asp Asp Ser Lys Val Pro
20 25 30

Lys Trp Met Gln Leu Leu Ile Thr Asp Val Phe Ser Phe Val Thr Thr
35 40 45

His Tyr Phe Val Trp Ser Leu Pro Phe Leu Ala Leu Phe Cys Tyr Leu
50 55 60

His Gln His Glu Leu Asp Tyr Val Ser Val Ala Met Ile Ala Leu Tyr
65 70 75 80

Leu Pro Ser Phe Phe Ser Gly Ala Gln Lys Thr Gly Lys Gly Asn Glu
85 90 95

Trp Glu Ala Ala Arg Thr Ser Ser Leu Trp Gly Leu Met Asn Lys Phe
100 105 110

Leu Arg Val Lys Ile Ile Arg Glu Gln Glu Leu Asp Pro Lys Lys Lys
115 120 125

-continued

```
Phe Ile Phe Gly Phe His Pro His Gly Ile Leu Val Leu Ser Arg Ile
    130                 135                 140

Ala Gly Phe Gly Arg Asn Phe Ile Asp Val Cys Pro Gly Ile Thr Thr
145                 150                 155                 160

Arg Phe Leu Gly Ala Ser Ala Met Tyr Tyr Ile Pro Leu Gly Arg Glu
                165                 170                 175

Met Cys Leu Trp Met Gly Gly Val Asp Ala Ser Arg Ser Thr Gly Glu
            180                 185                 190

Lys Val Leu Lys Glu Gly Asn Ser Ile Ile Val Tyr Pro Gly Gly Val
        195                 200                 205

Pro Glu Ile Phe Leu Thr Asp Pro Asn Leu Lys Glu Thr Gln Leu Val
    210                 215                 220

Leu Lys Lys Arg Leu Gly Phe Ile Lys Leu Ala Met Arg Gln Gly Ala
225                 230                 235                 240

Gln Leu Val Pro Thr Phe Val Phe Gly Glu Lys Trp Leu Tyr Asn Met
                245                 250                 255

Trp Thr Pro Pro Glu Ser Val Thr Asn Phe Phe Arg Lys Thr Leu Gly
            260                 265                 270

Ile Pro Val Leu Val Phe Trp Gly Lys Phe Trp Trp Met Pro Lys Ala
        275                 280                 285

Pro Gly Glu Gly Lys Arg Tyr Gly Leu Val Tyr Gly Lys Pro Ile Ala
    290                 295                 300

Thr Lys His Asp Ser Asn Pro Ser Asp Glu Glu Ile Arg Ala Val His
305                 310                 315                 320

Ala Glu Tyr Val Ser Glu Ile Glu Arg Ile Phe Ser Gln Tyr Lys Ser
                325                 330                 335

Glu Phe Gly Tyr Asp Glu Asp Glu Thr Leu Ala Ile Ile
            340                 345
```

<210> SEQ ID NO 31
<211> LENGTH: 1212
<212> TYPE: DNA
<213> ORGANISM: Phythophtora infestance

<400> SEQUENCE: 31

```
atgccgcaag cttgtggacg gacgtctgcg tggctggaca atgacgcgcg tccagagcta      60

cagacgctac atggacgcat tcttcggttt gtgctgctgt ggtacctgtt cggactgtgg     120

attgtcgggc tggcatcgtt cataggtatg tggctcttct cggggctctg cacgatacgg     180

tcgttgttga gtttcctaca caatggaggc agttggactg cagccacgcc gctacctgtt     240

cttgtccaag tgtatctggt tggtatgatc gcgtacgaaa gttatcatta tgtgacgcgg     300

aacgcgctgc atgaatggcc gctaattcga cgcgtggtgc gctacgtgtt cctgcattac     360

ccgtattttc gactgaacgc tgtggttttc gaagagcgag aggatgcgaa gcagaacgtc     420

gagatccaag agccagagca ggagaaggat ggcaacgata gcactaccaa caagagcgac     480

gacgctagat acttcagctc gaaggctgca gctgcagcta tcgaagaaaa cgatgtgacc     540

ccgtacgtcg agccggacaa gcgcgcgtta tttactttcc acccacacgg agtactgacc     600

tgcgggttct cgttcaacgg tgctcatcac atggccttcc agcgtgcggc gtgccgctgg     660

atctcggctg agaacctctt ctacttcccg ataatgcgtg acattttgca ttggatggag     720

ttcagcagta gcaccaaaac cagcatggag aacaccatgc gtacaggtca gaacttatgt     780

ctactgcccg gaggcttcga agaagctacg ctctatcagc gaggcaagca ccgcgtgtac     840

attcagaagc gcttcggatt catcaaactg gcgcttcagc atggctacga catctacccg     900
```

```
gcgtacacat tcggcgaaga gtacacctat cacgcgtttc cttatctgca gtggctacgc    960

ttgcaattga accggttccg aatcccgggc gttatcttct tcgggattcc gttctgcttc   1020

ttcatgccac gctcggacgt ggacctcatt accgtcatcg gtaagccgct gcgccttcca   1080

cacattgaca acccgagcag agatgaggtg aaggagaacc acgacaagta cgtcgaggct   1140

ctgcgtgacc tatttgacag gtacaaatgt gtctacgctg ctgaccctga cgccgaatta   1200

gaaatttct ga                                                         1212


<210> SEQ ID NO 32
<211> LENGTH: 403
<212> TYPE: PRT
<213> ORGANISM: Phythophtora infestance

<400> SEQUENCE: 32

Met Pro Gln Ala Cys Gly Arg Thr Ser Ala Trp Leu Asp Asn Asp Ala
1               5                   10                  15

Arg Pro Glu Leu Gln Thr Leu His Gly Arg Ile Leu Arg Phe Val Leu
            20                  25                  30

Leu Trp Tyr Leu Phe Gly Leu Trp Ile Val Gly Leu Ala Ser Phe Ile
        35                  40                  45

Gly Met Trp Leu Phe Ser Gly Leu Cys Thr Ile Arg Ser Leu Leu Ser
    50                  55                  60

Phe Leu His Asn Gly Gly Ser Trp Thr Ala Ala Thr Pro Leu Pro Val
65                  70                  75                  80

Leu Val Gln Val Tyr Leu Val Gly Met Ile Ala Tyr Glu Ser Tyr His
                85                  90                  95

Tyr Val Thr Arg Asn Ala Leu His Glu Trp Pro Leu Ile Arg Arg Val
            100                 105                 110

Val Arg Tyr Val Phe Leu His Tyr Pro Tyr Phe Arg Leu Asn Ala Val
        115                 120                 125

Val Phe Glu Glu Arg Glu Asp Ala Lys Gln Asn Val Glu Ile Gln Glu
    130                 135                 140

Pro Glu Gln Glu Lys Asp Gly Asn Asp Ser Thr Thr Asn Lys Ser Asp
145                 150                 155                 160

Asp Ala Arg Tyr Phe Ser Ser Lys Ala Ala Ala Ala Ala Ile Glu Glu
                165                 170                 175

Asn Asp Val Thr Pro Tyr Val Glu Pro Asp Lys Arg Ala Leu Phe Thr
            180                 185                 190

Phe His Pro His Gly Val Leu Thr Cys Gly Phe Ser Phe Asn Gly Ala
        195                 200                 205

His His Met Ala Phe Gln Arg Ala Ala Cys Arg Trp Ile Ser Ala Glu
    210                 215                 220

Asn Leu Phe Tyr Phe Pro Ile Met Arg Asp Ile Leu His Trp Met Glu
225                 230                 235                 240

Phe Ser Ser Ser Thr Lys Thr Ser Met Glu Asn Thr Met Arg Thr Gly
                245                 250                 255

Gln Asn Leu Cys Leu Leu Pro Gly Gly Phe Glu Glu Ala Thr Leu Tyr
            260                 265                 270

Gln Arg Gly Lys His Arg Val Tyr Ile Gln Lys Arg Phe Gly Phe Ile
        275                 280                 285

Lys Leu Ala Leu Gln His Gly Tyr Asp Ile Tyr Pro Ala Tyr Thr Phe
    290                 295                 300

Gly Glu Glu Tyr Thr Tyr His Ala Phe Pro Tyr Leu Gln Trp Leu Arg
```

```
305                 310                 315                 320

Leu Gln Leu Asn Arg Phe Arg Ile Pro Gly Val Ile Phe Phe Gly Ile
                325                 330                 335

Pro Phe Cys Phe Phe Met Pro Arg Ser Asp Val Asp Leu Ile Thr Val
            340                 345                 350

Ile Gly Lys Pro Leu Arg Leu Pro His Ile Asp Asn Pro Ser Arg Asp
        355                 360                 365

Glu Val Lys Glu Asn His Asp Lys Tyr Val Glu Ala Leu Arg Asp Leu
    370                 375                 380

Phe Asp Arg Tyr Lys Cys Val Tyr Ala Ala Asp Pro Asp Ala Glu Leu
385                 390                 395                 400

Glu Ile Phe


<210> SEQ ID NO 33
<211> LENGTH: 1221
<212> TYPE: DNA
<213> ORGANISM: Phythophtora infestance

<400> SEQUENCE: 33

atggtcggcg ttgcgcacgc tgctacaggg cgcacgccct tgtggcccaa caataatgct      60

gttcctgagc tgcagacgct gcgcggatac gtggggcggc gcttcttgct gtggtcgctc     120

ttcggtctct ggatctttgg actcggggca tacatcctta tgtggctgta ctccggctgg     180

tgcgttggtc actgggcttg gacagcgctg caaaccaaaa gttgggcgct tgcaacacca     240

ccgccaatta gtgtgcaggt atatctagcg ttcacggcgc tgtacgagag ctaccactac     300

atcacgcgcg attcgctgca tttgtggccg cgcatgaggc gtctggcgcg gcacatcctg     360

ctgcgctacc cgtacttccg tctgaacgtg accattttcg aggaacgcga gcttgagaaa     420

caaaagcagc ggctaaagga cgagcagacc aacaacagcg acgacgccac agtagacacg     480

gagcaggatg aaagtgaaca cctcagtccc gctgcagcta tcaaggctgt tgaagagaac     540

gatatctcac cgtatgtgga gacaggaacc aagaacctgt tcgctttcca tccgcatgga     600

atactgacct gtggcttctc tttcaacggc gcatatcaca tgagcttcga gcgctctgcg     660

tgtcgatggc tgtcggctga gaacctcttc tggttccctc tcgtccgtga ccttctcaac     720

tggatggagt acagcagctg cgcgaaagcc aacatgctca agttcatgcg cagagatcaa     780

aacgtcagca tcattcctgg cggctttgaa gaagccacac tctaccagag aggcaaacat     840

cgcttgtatc ttaaaaagcg cttcgggttc atcaaaattg cattgcaaca tggctacaat     900

gtccatccag tatacacttt cggcgaggaa tacacgtacc acgcgttccc gtacctgcag     960

tcgctgcggc tgcaattgaa ccgacttcag attcctggca caatcttctt cggagaggcc    1020

tcgtgctttt acttgccacg caacgatatc gacctcatca ctgtcgttgg caagtctctg    1080

cgattcccac gaatcgagca cccatcgaag gaagatgtac aaaagtatca agcgcagtac    1140

atagaggcgc tgaggagtct attcgacagc tacaagggcg tgtacgctgt tgatcccaac    1200

gccaccctgg agatttttta a                                               1221


<210> SEQ ID NO 34
<211> LENGTH: 406
<212> TYPE: PRT
<213> ORGANISM: Phythophtora infestance

<400> SEQUENCE: 34

Met Val Gly Val Ala His Ala Ala Thr Gly Arg Thr Pro Leu Trp Pro
1               5                   10                  15
```

```
Asn Asn Asn Ala Val Pro Glu Leu Gln Thr Leu Arg Gly Tyr Val Gly
            20                  25                  30

Arg Arg Phe Leu Leu Trp Ser Leu Phe Gly Leu Trp Ile Phe Gly Leu
        35                  40                  45

Gly Ala Tyr Ile Leu Met Trp Leu Tyr Ser Gly Trp Cys Val Gly His
    50                  55                  60

Trp Ala Trp Thr Ala Leu Gln Thr Lys Ser Trp Ala Leu Ala Thr Pro
65                  70                  75                  80

Pro Pro Ile Ser Val Gln Val Tyr Leu Ala Phe Thr Ala Leu Tyr Glu
                85                  90                  95

Ser Tyr His Tyr Ile Thr Arg Asp Ser Leu His Leu Trp Pro Arg Met
            100                 105                 110

Arg Arg Leu Ala Arg His Ile Leu Leu Arg Tyr Pro Tyr Phe Arg Leu
        115                 120                 125

Asn Val Thr Ile Phe Glu Glu Arg Glu Leu Glu Lys Gln Lys Gln Arg
    130                 135                 140

Leu Lys Asp Glu Gln Thr Asn Asn Ser Asp Asp Ala Thr Val Asp Thr
145                 150                 155                 160

Glu Gln Asp Glu Ser Glu His Leu Ser Pro Ala Ala Ala Ile Lys Ala
                165                 170                 175

Val Glu Glu Asn Asp Ile Ser Pro Tyr Val Glu Thr Gly Thr Lys Asn
            180                 185                 190

Leu Phe Ala Phe His Pro His Gly Ile Leu Thr Cys Gly Phe Ser Phe
        195                 200                 205

Asn Gly Ala Tyr His Met Ser Phe Glu Arg Ser Ala Cys Arg Trp Leu
    210                 215                 220

Ser Ala Glu Asn Leu Phe Trp Phe Pro Leu Val Arg Asp Leu Leu Asn
225                 230                 235                 240

Trp Met Glu Tyr Ser Ser Cys Ala Lys Ala Asn Met Leu Lys Phe Met
                245                 250                 255

Arg Arg Asp Gln Asn Val Ser Ile Ile Pro Gly Gly Phe Glu Glu Ala
            260                 265                 270

Thr Leu Tyr Gln Arg Gly Lys His Arg Leu Tyr Leu Lys Lys Arg Phe
        275                 280                 285

Gly Phe Ile Lys Ile Ala Leu Gln His Gly Tyr Asn Val His Pro Val
    290                 295                 300

Tyr Thr Phe Gly Glu Glu Tyr Thr Tyr His Ala Phe Pro Tyr Leu Gln
305                 310                 315                 320

Ser Leu Arg Leu Gln Leu Asn Arg Leu Gln Ile Pro Gly Thr Ile Phe
                325                 330                 335

Phe Gly Glu Ala Ser Cys Phe Tyr Leu Pro Arg Asn Asp Ile Asp Leu
            340                 345                 350

Ile Thr Val Val Gly Lys Ser Leu Arg Phe Pro Arg Ile Glu His Pro
        355                 360                 365

Ser Lys Glu Asp Val Gln Lys Tyr Gln Ala Gln Tyr Ile Glu Ala Leu
    370                 375                 380

Arg Ser Leu Phe Asp Ser Tyr Lys Gly Val Tyr Ala Val Asp Pro Asn
385                 390                 395                 400

Ala Thr Leu Glu Ile Phe
                405
```

<210> SEQ ID NO 35
<211> LENGTH: 1551

<212> TYPE: DNA
<213> ORGANISM: Phythophtora infestance

<400> SEQUENCE: 35

```
atggacgtgg agaacagtct tttgacgcgg ctagcggcca acgggccgac aatgagcgac      60
gctcccatgc ttctgatggc tgtggtgctg gtgctggcgc tatctggcgt tgtgtccacc     120
gtctcgcagc agcgtcaaaa gcccagcgag gacgagacgc tgcagggccg taagctcacg     180
cgtaagctta gcagcatggg gctatcgacg ttggtgacag agacacctac aaacttgtcc     240
atcccagtgt ctgtattaac tgtcgaaggt catctggcta aggaagacta cgtcgagcgc     300
ctacgtgcgc gtatactaca cgacgccttc ttcctacgct ggcgcagcgt cgtacgtggt     360
gactacaaga caggcgtcta caagtatgtg gaagttcctg gctacgacgt ggcacagaac     420
gtggtggagc acacagttga agagggagag accacgatgt cgtacgttga gtcggcgtta     480
gtaaacaccc cgctggactt tgacaagccg ctctgggaga tgcatgtgat ccacgacccc     540
aagggcaatc ctggtaacac tagcgtcggc tggaaagtgc atcattgtct cggtgacggt     600
gcttcgctgg ctacagccat ggccaagctc agtgaccaga gtgagctctt cgacgccatg     660
gtcgagaagc gcctacaagc caagaagagc ccaaagaccc ccaagccacg caaacccgtg     720
actcagatca ttaaagacat tttggtcttc ctgtacgtct gcatctggtc ggtctacgtg     780
atctcctatc acatgttcgc actcgtgact cgtcgtgaac cggccaccgt ctttaaacgt     840
cccggcggca agcaaaaacg tctgtcgtac aacatgatct actctgtgaa tgccactaag     900
gccgtaggta aacacttccg cgccacagtg aacgacgtga tgcttaatgt cgtagctggt     960
gccatgcgga agaccatgtt gtctgtgggc gagtctgtgg ctccaacact caaggtacgc    1020
tgcgctatcc cagtggacat gcgctccagt acagaagtga tccgccacac tagcaaccgc    1080
ttctcctctc tcgtcattga cctgcccatc ggcgttgagg actctgctca gcgtctgctc    1140
caagtcacgg ctgctatgaa cgatgccaag aattcacttg agaagttctt cgtgtactgg    1200
tcgacccacc tcgtgtcgat gttgccagcg ccgcttatgc gcttgatcgt acactttact    1260
accagtcgta tctctgtggc aacgagcaat gtgcgtgcta gtgtcgtgga agtgagtcta    1320
tgcaagagtc cagtgtcggg cttctacggg ttcgtgcctc caccgccata tgtgaacctt    1380
ggagtagcca tcttgtcaat gggcgatgat ctcggtctta acgttcttgt ggacccatgt    1440
gtcggtgtca acgcgaagca attcctggag tttgcgaagg aagagttcac tgcactgcaa    1500
gaatcggtcg ctgctatgga ggcaaatgcc ggtgacaaga agacaaaata a             1551
```

<210> SEQ ID NO 36
<211> LENGTH: 516
<212> TYPE: PRT
<213> ORGANISM: Phythophtora infestance

<400> SEQUENCE: 36

```
Met Asp Val Glu Asn Ser Leu Leu Thr Arg Leu Ala Ala Asn Gly Pro
1               5                   10                  15

Thr Met Ser Asp Ala Pro Met Leu Leu Met Ala Val Val Leu Val Leu
            20                  25                  30

Ala Leu Ser Gly Val Val Ser Thr Val Ser Gln Gln Arg Gln Lys Pro
        35                  40                  45

Ser Glu Asp Glu Thr Leu Gln Gly Arg Lys Leu Thr Arg Lys Leu Ser
    50                  55                  60

Ser Met Gly Leu Ser Thr Leu Val Thr Glu Thr Pro Thr Asn Leu Ser
65                  70                  75                  80
```

-continued

```
Ile Pro Val Ser Val Leu Thr Val Glu Gly His Leu Ala Lys Glu Asp
                85                  90                  95

Tyr Val Glu Arg Leu Arg Ala Arg Ile Leu His Asp Ala Phe Phe Leu
            100                 105                 110

Arg Trp Arg Ser Val Val Arg Gly Asp Tyr Lys Thr Gly Val Tyr Lys
        115                 120                 125

Tyr Val Glu Val Pro Gly Tyr Asp Val Ala Gln Asn Val Val Glu His
    130                 135                 140

Thr Val Glu Glu Gly Glu Thr Thr Met Ser Tyr Val Glu Ser Ala Leu
145                 150                 155                 160

Val Asn Thr Pro Leu Asp Phe Asp Lys Pro Leu Trp Glu Met His Val
                165                 170                 175

Ile His Asp Pro Lys Gly Asn Pro Gly Asn Thr Ser Val Gly Trp Lys
            180                 185                 190

Val His His Cys Leu Gly Asp Gly Ala Ser Leu Ala Thr Ala Met Ala
        195                 200                 205

Lys Leu Ser Asp Gln Ser Glu Leu Phe Asp Ala Met Val Glu Lys Arg
    210                 215                 220

Leu Gln Ala Lys Lys Ser Pro Lys Thr Pro Lys Pro Arg Lys Pro Val
225                 230                 235                 240

Thr Gln Ile Ile Lys Asp Ile Leu Val Phe Leu Tyr Val Cys Ile Trp
                245                 250                 255

Ser Val Tyr Val Ile Ser Tyr His Met Phe Ala Leu Val Thr Arg Arg
            260                 265                 270

Glu Pro Ala Thr Val Phe Lys Arg Pro Gly Gly Lys Gln Lys Arg Leu
        275                 280                 285

Ser Tyr Asn Met Ile Tyr Ser Val Asn Ala Thr Lys Ala Val Gly Lys
    290                 295                 300

His Phe Arg Ala Thr Val Asn Asp Val Met Leu Asn Val Val Ala Gly
305                 310                 315                 320

Ala Met Arg Lys Thr Met Leu Ser Val Gly Glu Ser Val Ala Pro Thr
                325                 330                 335

Leu Lys Val Arg Cys Ala Ile Pro Val Asp Met Arg Ser Ser Thr Glu
            340                 345                 350

Val Ile Arg His Thr Ser Asn Arg Phe Ser Ser Leu Val Ile Asp Leu
        355                 360                 365

Pro Ile Gly Val Glu Asp Ser Ala Gln Arg Leu Leu Gln Val Thr Ala
    370                 375                 380

Ala Met Asn Asp Ala Lys Asn Ser Leu Glu Lys Phe Phe Val Tyr Trp
385                 390                 395                 400

Ser Thr His Leu Val Ser Met Leu Pro Ala Pro Leu Met Arg Leu Ile
                405                 410                 415

Val His Phe Thr Thr Ser Arg Ile Ser Val Ala Thr Ser Asn Val Arg
            420                 425                 430

Ala Ser Val Val Glu Val Ser Leu Cys Lys Ser Pro Val Ser Gly Phe
        435                 440                 445

Tyr Gly Phe Val Pro Pro Pro Pro Tyr Val Asn Leu Gly Val Ala Ile
    450                 455                 460

Leu Ser Met Gly Asp Asp Leu Gly Leu Asn Val Leu Val Asp Pro Cys
465                 470                 475                 480

Val Gly Val Asn Ala Lys Gln Phe Leu Glu Phe Ala Lys Glu Glu Phe
                485                 490                 495
```

-continued

```
Thr Ala Leu Gln Glu Ser Val Ala Ala Met Glu Ala Asn Ala Gly Asp
            500                 505                 510

Lys Lys Thr Lys
        515


<210> SEQ ID NO 37
<211> LENGTH: 2028
<212> TYPE: DNA
<213> ORGANISM: Phythophtora infestance

<400> SEQUENCE: 37

atgacactgg acgacgattc ctcagcctcg ggcgtgcgcc agcgcaagcc acacggcggc     60

acctccagtg acaggccatc atcccccgag gccttggcgg aggaggccgt cgcttcggcc    120

ttctcggccc ccaaggatga gcagtctcga accaaggaaa cgtttcaaca tgccgctcgc    180

tcgctcggcc ggacacaaag ttggcacgcg cgggcggccg accacgtggc caggaagcgc    240

atctactcca tcatggccgg cgtcattatt ggtgtcgcgg ccgttatcaa ttttcagaga    300

ttttacctgg agaagcctct gatcagcgaa gactcattgc tcatggtccg ggagatgttt    360

gacaacttta actggtccgt gaacgttaag gaagagctca tggctgcctt cgataaccgg    420

ccacctctta tgggtgcagc cgagattcgg cccggtgtcc agttgttcca agagaacgtg    480

acggccaact cgcctgttgt attggtgccc ggcttcacat ctacgggcct cgagatctgg    540

aacggtagcg aatgcagcaa ggcctatttc agacaacgta tgtggggcac atccaggatg    600

ttgcagcagt ttatgatgaa ccaaaagtgc tggttagagc acatgatgct caaccggtcg    660

tcaggtatgg acccggacgg catcaagtta cgcgcggcca aaggcttaga agcggccgac    720

tatttgatcg gcggcttctg ggtctgggga aagatggtgg agaacttggc cgagatcgga    780

tacgacagca acaatctgta catggccgcg tacgactgga ggctcatgcc gcatcttttg    840

gagaagcgcg acgggtattt tacgaaactc aaatacacta tcgagatggc gcgaatgtcg    900

gccggcggcc acaaggtgat gctggtcacg cactcgtatg ctacgcaagt gtttttccac    960

tttttgaagt gggtagagag tgagaacgga ggcaaaggtg gcgaccagtg ggtggagacc   1020

aaccttgagt ccttcgttaa tattgccggc ccgaccttgg gcgtggtcaa gacgatcagt   1080

gcgttgatgt cgggcgagat gaaggatacg gccgagctgg gcgggctgtc caagttcctc   1140

ggctactttt tcagtgtgtc ggcgcgtacg caactggccc gctcgtggtc gagtgtgttc   1200

tcgatgatgc ctatcggtgg tgaccgtatc tggggcacgg ccgactcggc cccgacgat    1260

gtggtagcgg cctccccgtt atcgaccgga aagaactcga cgatcgaccc aaggaaggtc   1320

aaagagcacg tggcacgcta cggatcgaat ggccacgtcg ttcggttcgt caatacttca   1380

cacgagaacg tcactatcgg aggcgtacag aagatgctgg gcaaattaga cccgtacctt   1440

gaccagttcc gttcgtggct gagtaccggt attgccgaag atctgtcctt gcctgaatac   1500

gatcaatcca agtactggac gaacccgttg gaggctgctc tacccaaagc tccgagcctc   1560

aatgtgttct gcttttacgg tgtcggcaaa cctgttgagc gaggatacac gtacggagac   1620

aacccgcccg atgaagataa cgcgacagtg aacggcaaac gtgttgctcc gtacgtgttc   1680

aacacggata ccgacgatct tccgtacatc aagggtgggc tcagatactc ggacggagac   1740

ggcacggtgc cgctgatctc tctgggcctc atgtgtgcca gtggctggcg gacgaagaag   1800

ttcaaccccg gcaacgtcga cgtacgtgtt cgtgaatacc gacacaaccc cgtgtccatg   1860

ctgttcgacg cgcgtggcgg acctgagacg gccgatcacg tcgacatcat gggcaaccac   1920

ggtctcatcc gggacgttct actcgtcgcc gctagggcgt acgaccgcgt gcctgaaaac   1980
```

attacgtcca gcatcatgga gattgccgaa cgtgtcggag agctctaa 2028

<210> SEQ ID NO 38
<211> LENGTH: 675
<212> TYPE: PRT
<213> ORGANISM: Phythophtora infestance

<400> SEQUENCE: 38

Met Thr Leu Asp Asp Asp Ser Ser Ala Ser Gly Val Arg Gln Arg Lys
1 5 10 15

Pro His Gly Gly Thr Ser Ser Asp Arg Pro Ser Ser Pro Glu Ala Leu
20 25 30

Ala Glu Glu Ala Val Ala Ser Ala Phe Ser Ala Pro Lys Asp Glu Gln
35 40 45

Ser Arg Thr Lys Glu Thr Phe Gln His Ala Ala Arg Ser Leu Gly Arg
50 55 60

Thr Gln Ser Trp His Ala Arg Ala Ala Asp His Val Ala Arg Lys Arg
65 70 75 80

Ile Tyr Ser Ile Met Ala Gly Val Ile Ile Gly Val Ala Ala Val Ile
85 90 95

Asn Phe Gln Arg Phe Tyr Leu Glu Lys Pro Leu Ile Ser Glu Asp Ser
100 105 110

Leu Leu Met Val Arg Glu Met Phe Asp Asn Phe Asn Trp Ser Val Asn
115 120 125

Val Lys Glu Glu Leu Met Ala Ala Phe Asp Asn Arg Pro Pro Leu Met
130 135 140

Gly Ala Ala Glu Ile Arg Pro Gly Val Gln Leu Phe Gln Glu Asn Val
145 150 155 160

Thr Ala Asn Ser Pro Val Val Leu Val Pro Gly Phe Thr Ser Thr Gly
165 170 175

Leu Glu Ile Trp Asn Gly Ser Glu Cys Ser Lys Ala Tyr Phe Arg Gln
180 185 190

Arg Met Trp Gly Thr Ser Arg Met Leu Gln Gln Phe Met Met Asn Gln
195 200 205

Lys Cys Trp Leu Glu His Met Met Leu Asn Arg Ser Ser Gly Met Asp
210 215 220

Pro Asp Gly Ile Lys Leu Arg Ala Ala Lys Gly Leu Glu Ala Ala Asp
225 230 235 240

Tyr Leu Ile Gly Gly Phe Trp Val Trp Gly Lys Met Val Glu Asn Leu
245 250 255

Ala Glu Ile Gly Tyr Asp Ser Asn Asn Leu Tyr Met Ala Ala Tyr Asp
260 265 270

Trp Arg Leu Met Pro His Leu Leu Glu Lys Arg Asp Gly Tyr Phe Thr
275 280 285

Lys Leu Lys Tyr Thr Ile Glu Met Ala Arg Met Ser Ala Gly Gly His
290 295 300

Lys Val Met Leu Val Thr His Ser Tyr Ala Thr Gln Val Phe Phe His
305 310 315 320

Phe Leu Lys Trp Val Glu Ser Glu Asn Gly Gly Lys Gly Gly Asp Gln
325 330 335

Trp Val Glu Thr Asn Leu Glu Ser Phe Val Asn Ile Ala Gly Pro Thr
340 345 350

Leu Gly Val Val Lys Thr Ile Ser Ala Leu Met Ser Gly Glu Met Lys
355 360 365

```
Asp Thr Ala Glu Leu Gly Gly Leu Ser Lys Phe Leu Gly Tyr Phe Phe
    370                 375                 380

Ser Val Ser Ala Arg Thr Gln Leu Ala Arg Ser Trp Ser Ser Val Phe
385                 390                 395                 400

Ser Met Met Pro Ile Gly Gly Asp Arg Ile Trp Gly Thr Ala Asp Ser
                405                 410                 415

Ala Pro Asp Asp Val Val Ala Ala Ser Pro Leu Ser Thr Gly Lys Asn
            420                 425                 430

Ser Thr Ile Asp Pro Arg Lys Val Lys Glu His Val Ala Arg Tyr Gly
        435                 440                 445

Ser Asn Gly His Val Val Arg Phe Val Asn Thr Ser His Glu Asn Val
    450                 455                 460

Thr Ile Gly Gly Val Gln Lys Met Leu Gly Lys Leu Asp Pro Tyr Leu
465                 470                 475                 480

Asp Gln Phe Arg Ser Trp Leu Ser Thr Gly Ile Ala Glu Asp Leu Ser
                485                 490                 495

Leu Pro Glu Tyr Asp Gln Ser Lys Tyr Trp Thr Asn Pro Leu Glu Ala
            500                 505                 510

Ala Leu Pro Lys Ala Pro Ser Leu Asn Val Phe Cys Phe Tyr Gly Val
        515                 520                 525

Gly Lys Pro Val Glu Arg Gly Tyr Thr Tyr Gly Asp Asn Pro Pro Asp
    530                 535                 540

Glu Asp Asn Ala Thr Val Asn Gly Lys Arg Val Ala Pro Tyr Val Phe
545                 550                 555                 560

Asn Thr Asp Thr Asp Asp Leu Pro Tyr Ile Lys Gly Gly Leu Arg Tyr
                565                 570                 575

Ser Asp Gly Asp Gly Thr Val Pro Leu Ile Ser Leu Gly Leu Met Cys
            580                 585                 590

Ala Ser Gly Trp Arg Thr Lys Lys Phe Asn Pro Gly Asn Val Asp Val
        595                 600                 605

Arg Val Arg Glu Tyr Arg His Asn Pro Val Ser Met Leu Phe Asp Ala
    610                 615                 620

Arg Gly Gly Pro Glu Thr Ala Asp His Val Asp Ile Met Gly Asn His
625                 630                 635                 640

Gly Leu Ile Arg Asp Val Leu Leu Val Ala Ala Arg Ala Tyr Asp Arg
                645                 650                 655

Val Pro Glu Asn Ile Thr Ser Ser Ile Met Glu Ile Ala Glu Arg Val
            660                 665                 670

Gly Glu Leu
        675
```

<210> SEQ ID NO 39
<211> LENGTH: 2187
<212> TYPE: DNA
<213> ORGANISM: Phythophtora infestance

<400> SEQUENCE: 39

```
atgaagttcg acgacaagaa ggtgctcaat gacacatgga cgcagttcct ggcgctgtgt      60

ctgctgctca tgctggctgt cgactcgctc aaccccatca aggctgtaag taagtttcta     120

ggcgttccgt cgtattactg gggcgctctg tccgtgggta ttatgctagg gctgctgttc     180

cacaacgccg ccgacgtcat ctaccgttcc acacgcgtct tcctcaacag tatcctcagt     240

atctcattta agagtgtgga tctcatcggt ctggataacg taccgaccga cgggcccgtc     300
```

```
atcttcaccg gtaaccacgc caaccagttc gtagacggtc ttgtagtcat gatgactagt    360

cctcgtaaag taggcttcat gatcgcagaa aagtcgtggc atttgcctgt cgtgggccac    420

ttggctcgta tcatgggctg catcccggtg gtgcgtcctc aggactctgt agcttctggt    480

gttggcagca tgaagctcgc cagtgaagat cccgtgactg tagctagctc gtccagtggt    540

ggcgctagca gtagtacgcc tcagtggctc gtgcagggcg acggcaccag tttcactaag    600

caggtgacgc ctggagacca gatccgcttc caagggcaga gcgtcaagga ctcggggtcg    660

cctgtgaaga tcgtacaggt tctagacgac acgcagttgc tactgaacgc gccgttgaag    720

agcggcgaag gcaaattagt gcttgagagt gcaccgtttg gtattctcaa gcgtgtggac    780

caatccgtga cgtttgccaa ggtgtacacg cacttgaagc gtgggaactg catcggtatc    840

ttcccggaag gaggctcaca cgaccgtacg gacttgttac cactaaaagc tggtgttgcc    900

gtcatggctc ttggagttaa ggacaagtac aacatcaacg tgccggtggt gcctgtgggc    960

ttgaactact tccgtggcca tcgcttccgt ggccgcgtga cggtggaatt cggcactccg   1020

atcactgtgg accaagcgtt gatggccaag taccaggaag acaagcgtac agcgtgtaac   1080

acgctcttac atcgtgtgga ggagagtatg cgctccgtga tcgtgactac gcccagctac   1140

ggcgtcatgc aggaggtgtt gactgcgcgt cgtctcttcc agcgctctgg agtgcggctg   1200

tcggcaaaag agacacaaga cttgaaccgc cgctttgcag aaggctacaa ggtgttgcag   1260

gatgtgccag aagcccaaga agatctcgta atcttgcaac ataagctgga taactactac   1320

aagacgctgc agaagatggg actcaaggac catcaagtgc cgtatatccc gtggtggaca   1380

attcacgacg tgttgggctc cgcactgtac ggcacgttga tccttctact gtcctccatt   1440

ccgtcgttca tcctgaatgc accggtgggg cttctagctc gttatgtggc gaattcagcg   1500

cagaagaagg cgctggaagg ctccaaggtc aaggtgttgg ctcgcgacgt tattcttagc   1560

aagaagatcc agttctcgat tgtagctgtg cccgtgctgt ggttcattta ttttacgatc   1620

gccgcggtgt tcacggattg gtactggtcg tcaatcatgc tgctgatggt gtcgttcccg   1680

ctattttctt tcttcggtgt acgctcggta gaggctggaa tgatcgagct gaagacggtc   1740

cgtccgttgt tctaccgtct gctaccgacg tacaaggcta cacaggatga gcttcctcgg   1800

caacgtgctg agttgcagaa ggaagtgcgt gagtttgtga agaaatactc gcagtatctg   1860

ggaaaactgg ccgagccaaa gaagctcgac tggagcgagt acatgcacga gcgctcgttg   1920

gtattggctg agaagactga gcaggccgag tcgatcccgt cgcctcctcc ggtacatgag   1980

gaggacgagg agccgcggga aggcgaggct gaagatgata tcggctctcc tgtgcctacg   2040

atcaccaagt tccacgacat cagtatcctg ggcaagtcgg agaactcggt gctggactta   2100

gcaggtctcg aacgctccat gtcttgcccg ccaggatacc aagagctagc ggaggagata   2160

gccaagcaac gtaaagggtc cgtgtag                                       2187
```

<210> SEQ ID NO 40
<211> LENGTH: 728
<212> TYPE: PRT
<213> ORGANISM: Phythophtora infestance

<400> SEQUENCE: 40

```
Met Lys Phe Asp Asp Lys Lys Val Leu Asn Asp Thr Trp Thr Gln Phe
1               5                   10                  15

Leu Ala Leu Cys Leu Leu Leu Met Leu Ala Val Asp Ser Leu Asn Pro
            20                  25                  30

Ile Lys Ala Val Ser Lys Phe Leu Gly Val Pro Ser Tyr Tyr Trp Gly
```

-continued

```
        35                  40                  45

Ala Leu Ser Val Gly Ile Met Leu Gly Leu Leu Phe His Asn Ala Ala
    50                  55                  60

Asp Val Ile Tyr Arg Ser Thr Arg Val Phe Leu Asn Ser Ile Leu Ser
65                  70                  75                  80

Ile Ser Phe Lys Ser Val Asp Leu Ile Gly Leu Asp Asn Val Pro Thr
                85                  90                  95

Asp Gly Pro Val Ile Phe Thr Gly Asn His Ala Asn Gln Phe Val Asp
            100                 105                 110

Gly Leu Val Val Met Met Thr Ser Pro Arg Lys Val Gly Phe Met Ile
        115                 120                 125

Ala Glu Lys Ser Trp His Leu Pro Val Val Gly His Leu Ala Arg Ile
    130                 135                 140

Met Gly Cys Ile Pro Val Val Arg Pro Gln Asp Ser Val Ala Ser Gly
145                 150                 155                 160

Val Gly Ser Met Lys Leu Ala Ser Glu Asp Pro Val Thr Val Ala Ser
                165                 170                 175

Ser Ser Ser Gly Gly Ala Ser Ser Ser Thr Pro Gln Trp Leu Val Gln
            180                 185                 190

Gly Asp Gly Thr Ser Phe Thr Lys Gln Val Thr Pro Gly Asp Gln Ile
        195                 200                 205

Arg Phe Gln Gly Gln Ser Val Lys Asp Ser Gly Ser Pro Val Lys Ile
    210                 215                 220

Val Gln Val Leu Asp Asp Thr Gln Leu Leu Leu Asn Ala Pro Leu Lys
225                 230                 235                 240

Ser Gly Glu Gly Lys Leu Val Leu Glu Ser Ala Pro Phe Gly Ile Leu
                245                 250                 255

Lys Arg Val Asp Gln Ser Val Thr Phe Ala Lys Val Tyr Thr His Leu
            260                 265                 270

Lys Arg Gly Asn Cys Ile Gly Ile Phe Pro Glu Gly Gly Ser His Asp
        275                 280                 285

Arg Thr Asp Leu Leu Pro Leu Lys Ala Gly Val Ala Val Met Ala Leu
    290                 295                 300

Gly Val Lys Asp Lys Tyr Asn Ile Asn Val Pro Val Val Pro Val Gly
305                 310                 315                 320

Leu Asn Tyr Phe Arg Gly His Arg Phe Arg Gly Arg Val Thr Val Glu
                325                 330                 335

Phe Gly Thr Pro Ile Thr Val Asp Gln Ala Leu Met Ala Lys Tyr Gln
            340                 345                 350

Glu Asp Lys Arg Thr Ala Cys Asn Thr Leu Leu His Arg Val Glu Glu
        355                 360                 365

Ser Met Arg Ser Val Ile Val Thr Thr Pro Ser Tyr Gly Val Met Gln
    370                 375                 380

Glu Val Leu Thr Ala Arg Arg Leu Phe Gln Arg Ser Gly Val Arg Leu
385                 390                 395                 400

Ser Ala Lys Glu Thr Gln Asp Leu Asn Arg Arg Phe Ala Glu Gly Tyr
                405                 410                 415

Lys Val Leu Gln Asp Val Pro Glu Ala Gln Glu Asp Leu Val Ile Leu
            420                 425                 430

Gln His Lys Leu Asp Asn Tyr Tyr Lys Thr Leu Gln Lys Met Gly Leu
        435                 440                 445

Lys Asp His Gln Val Pro Tyr Ile Pro Trp Trp Thr Ile His Asp Val
    450                 455                 460
```

Leu Gly Ser Ala Leu Tyr Gly Thr Leu Ile Leu Leu Leu Ser Ser Ile
465 470 475 480

Pro Ser Phe Ile Leu Asn Ala Pro Val Gly Leu Leu Ala Arg Tyr Val
485 490 495

Ala Asn Ser Ala Gln Lys Lys Ala Leu Glu Gly Ser Lys Val Lys Val
500 505 510

Leu Ala Arg Asp Val Ile Leu Ser Lys Lys Ile Gln Phe Ser Ile Val
515 520 525

Ala Val Pro Val Leu Trp Phe Ile Tyr Phe Thr Ile Ala Ala Val Phe
530 535 540

Thr Asp Trp Tyr Trp Ser Ser Ile Met Leu Leu Met Val Ser Phe Pro
545 550 555 560

Leu Phe Ser Phe Phe Gly Val Arg Ser Val Glu Ala Gly Met Ile Glu
565 570 575

Leu Lys Thr Val Arg Pro Leu Phe Tyr Arg Leu Leu Pro Thr Tyr Lys
580 585 590

Ala Thr Gln Asp Glu Leu Pro Arg Gln Arg Ala Glu Leu Gln Lys Glu
595 600 605

Val Arg Glu Phe Val Lys Lys Tyr Ser Gln Tyr Leu Gly Lys Leu Ala
610 615 620

Glu Pro Lys Lys Leu Asp Trp Ser Glu Tyr Met His Glu Arg Ser Leu
625 630 635 640

Val Leu Ala Glu Lys Thr Glu Gln Ala Glu Ser Ile Pro Ser Pro Pro
645 650 655

Pro Val His Glu Glu Asp Glu Glu Pro Arg Glu Gly Glu Ala Glu Asp
660 665 670

Asp Ile Gly Ser Pro Val Pro Thr Ile Thr Lys Phe His Asp Ile Ser
675 680 685

Ile Leu Gly Lys Ser Glu Asn Ser Val Leu Asp Leu Ala Gly Leu Glu
690 695 700

Arg Ser Met Ser Cys Pro Pro Gly Tyr Gln Glu Leu Ala Glu Glu Ile
705 710 715 720

Ala Lys Gln Arg Lys Gly Ser Val
725

<210> SEQ ID NO 41
<211> LENGTH: 1533
<212> TYPE: DNA
<213> ORGANISM: Phythophtora infestance

<400> SEQUENCE: 41
atgctgtcta cgctactatg gcttgcgctg gccgtcgtgg tccttgctac acagggctac 60
aagatggtgg cgcgcttcct gcgactattg ctacacactt acttccgcaa aatcgtggtt 120
tacggactca acaacttccc gcgtgagggg cctgtgatcc tgtgcccgaa ccaccccaac 180
atgcttgtgg acgccattct cgtcatgacc gaggccgtaa gtcacggtcg caatccgtac 240
gtatgggcca agggttcgct gttcagcaac cctgtcgccg ccttcttcct caagaaattc 300
ggcgccgtgc cggtctatcg tccgcggcgc aaagaggaca gtctcgccga cgtggactca 360
gataagactc ccgagcaact ggaggcggcc aaccgcaaaa tgttcgagca tacgtggcat 420
gtacttgctg ggggcaacgt catggtgctt ttccctgaag gaacatcgta cacggctcca 480
aagatgctgt cactgcgtac gggtgttgtg cgtgtcgcga cgggtttcgc taagcattat 540
gaccaaccta tcccgatcat cccgctaggt ctcaactact tcaacaaaga ccacttcagg 600

-continued

```
agccagatga cgctggaatt cggtccaccg atggtgatca cgcccgacat ggtgcaaact    660

gaagctttcc aacaggacga acatggcgag gtgaagcgtc tgaccctgga gctagaggag    720

cgcatgcacg atgtgacttt gaatgcatct gacttcagca ctatccacgc tgcgcgaatg    780

atgcgacgcc tctatctaaa cactcctggc cccattgaca ccaacaaaga agtccgtttg    840

acacagtaca ttatcaatat gctggagaag gagccccaag acgacgagca aaaggagcga    900

atcgctacga tccgtgaaaa agttcttcga tacaaagagc aattggaaaa gctgcggttg    960

aaagaccaag aggtgaattt gccgatgccc aaagagaaat cgcttttgca actgtttttg   1020

gagcggattc tgtacctgct tgtgctgctg ccactggcca cgcccgggct tttgttgaat   1080

ttaccctact attttattgg aacgaagatg aacagcctcg caggattcgt ggaatccaag   1140

tcgatgttca agatcttcgc tgctgctgtg ttggtgcctg tacattggct cgtactgatc   1200

cttgcaactt ggtatttcct cggatcatcg tatgcgtatg tgctggctgt tggtttgccg   1260

ctgctgctgt actcgcacat ccgcgtactg gaagagagcc gctccatcgc cgagaacgtg   1320

tatttcctct tcaacatcac agctcacgcc gataaggtgg cggtgcttcg aacggaacgg   1380

gagctgctag cgcaagaagt ccacgagctt gtgactaagt acgtcgatgc caagtttctc   1440

tcagccatac acaagtctct agcgagctcg cccgtgaaca gacgattgcg ccaccgtgcc   1500

tcctccacca gcgacacact gcttactaca tag                                1533
```

<210> SEQ ID NO 42
<211> LENGTH: 510
<212> TYPE: PRT
<213> ORGANISM: Phythophtora infestance

<400> SEQUENCE: 42

```
Met Leu Ser Thr Leu Leu Trp Leu Ala Leu Ala Val Val Val Leu Ala
1               5                   10                  15

Thr Gln Gly Tyr Lys Met Val Ala Arg Phe Leu Arg Leu Leu Leu His
            20                  25                  30

Thr Tyr Phe Arg Lys Ile Val Val Tyr Gly Leu Asn Asn Phe Pro Arg
        35                  40                  45

Glu Gly Pro Val Ile Leu Cys Pro Asn His Pro Asn Met Leu Val Asp
    50                  55                  60

Ala Ile Leu Val Met Thr Glu Ala Val Ser His Gly Arg Asn Pro Tyr
65                  70                  75                  80

Val Trp Ala Lys Gly Ser Leu Phe Ser Asn Pro Val Ala Ala Phe Phe
                85                  90                  95

Leu Lys Lys Phe Gly Ala Val Pro Val Tyr Arg Pro Arg Arg Lys Glu
            100                 105                 110

Asp Ser Leu Ala Asp Val Asp Ser Asp Lys Thr Pro Glu Gln Leu Glu
        115                 120                 125

Ala Ala Asn Arg Lys Met Phe Glu His Thr Trp His Val Leu Ala Gly
    130                 135                 140

Gly Asn Val Met Val Leu Phe Pro Glu Gly Thr Ser Tyr Thr Ala Pro
145                 150                 155                 160

Lys Met Leu Ser Leu Arg Thr Gly Val Val Arg Val Ala Thr Gly Phe
                165                 170                 175

Ala Lys His Tyr Asp Gln Pro Ile Pro Ile Ile Pro Leu Gly Leu Asn
            180                 185                 190

Tyr Phe Asn Lys Asp His Phe Arg Ser Gln Met Thr Leu Glu Phe Gly
        195                 200                 205
```

```
Pro Pro Met Val Ile Thr Pro Asp Met Val Gln Thr Glu Ala Phe Gln
    210                 215                 220

Gln Asp Glu His Gly Glu Val Lys Arg Leu Thr Leu Glu Leu Glu Glu
225                 230                 235                 240

Arg Met His Asp Val Thr Leu Asn Ala Ser Asp Phe Ser Thr Ile His
                245                 250                 255

Ala Ala Arg Met Met Arg Arg Leu Tyr Leu Asn Thr Pro Gly Pro Ile
            260                 265                 270

Asp Thr Asn Lys Glu Val Arg Leu Thr Gln Tyr Ile Ile Asn Met Leu
        275                 280                 285

Glu Lys Glu Pro Gln Asp Asp Glu Gln Lys Glu Arg Ile Ala Thr Ile
    290                 295                 300

Arg Glu Lys Val Leu Arg Tyr Lys Glu Gln Leu Glu Lys Leu Arg Leu
305                 310                 315                 320

Lys Asp Gln Glu Val Asn Leu Pro Met Pro Lys Glu Lys Ser Leu Leu
                325                 330                 335

Gln Leu Phe Leu Glu Arg Ile Leu Tyr Leu Leu Val Leu Leu Pro Leu
            340                 345                 350

Ala Thr Pro Gly Leu Leu Leu Asn Leu Pro Tyr Tyr Phe Ile Gly Thr
        355                 360                 365

Lys Met Asn Ser Leu Ala Gly Phe Val Glu Ser Lys Ser Met Phe Lys
    370                 375                 380

Ile Phe Ala Ala Ala Val Leu Val Pro Val His Trp Leu Val Leu Ile
385                 390                 395                 400

Leu Ala Thr Trp Tyr Phe Leu Gly Ser Ser Tyr Ala Tyr Val Leu Ala
                405                 410                 415

Val Gly Leu Pro Leu Leu Leu Tyr Ser His Ile Arg Val Leu Glu Glu
            420                 425                 430

Ser Arg Ser Ile Ala Glu Asn Val Tyr Phe Leu Phe Asn Ile Thr Ala
        435                 440                 445

His Ala Asp Lys Val Ala Val Leu Arg Thr Glu Arg Glu Leu Leu Ala
    450                 455                 460

Gln Glu Val His Glu Leu Val Thr Lys Tyr Val Asp Ala Lys Phe Leu
465                 470                 475                 480

Ser Ala Ile His Lys Ser Leu Ala Ser Ser Pro Val Asn Arg Arg Leu
                485                 490                 495

Arg His Arg Ala Ser Ser Thr Ser Asp Thr Leu Leu Thr Thr
            500                 505                 510
```

<210> SEQ ID NO 43
<211> LENGTH: 93
<212> TYPE: DNA
<213> ORGANISM: artificial
<220> FEATURE:
<223> OTHER INFORMATION: Primer

<400> SEQUENCE: 43

```
ataaaagtat caacaaaaaa ttgttaatat acctctatac tttaacgtca aggagaaaaa     60

accccggatc atgaactgcc agcgtcatcc aac                                  93
```

<210> SEQ ID NO 44
<211> LENGTH: 96
<212> TYPE: DNA
<213> ORGANISM: artificial
<220> FEATURE:
<223> OTHER INFORMATION: Primer

<400> SEQUENCE: 44
aactataaaa aaataaatag ggacctagac ttcaggttgt ctaactcctt ccttttcggt 60
tagagcggat ttattacaag gtcttcttac tgttcg 96

<210> SEQ ID NO 45
<211> LENGTH: 93
<212> TYPE: DNA
<213> ORGANISM: artificial
<220> FEATURE:
<223> OTHER INFORMATION: Primer

<400> SEQUENCE: 45
ataaaagtat caacaaaaaa ttgttaatat acctctatac tttaacgtca aggagaaaaa 60
accccggatc atggaccgcg tcgtggactt tgt 93

<210> SEQ ID NO 46
<211> LENGTH: 96
<212> TYPE: DNA
<213> ORGANISM: artificial
<220> FEATURE:
<223> OTHER INFORMATION: Primer

<400> SEQUENCE: 46
aactataaaa aaataaatag ggacctagac ttcaggttgt ctaactcctt ccttttcggt 60
tagagcggat ttatcacaaa tacttattaa gtacct 96

<210> SEQ ID NO 47
<211> LENGTH: 93
<212> TYPE: DNA
<213> ORGANISM: artificial
<220> FEATURE:
<223> OTHER INFORMATION: Primer

<400> SEQUENCE: 47
ataaaagtat caacaaaaaa ttgttaatat acctctatac tttaacgtca aggagaaaaa 60
accccggatc atgcgtgtca ctcgccgcat tcg 93

<210> SEQ ID NO 48
<211> LENGTH: 96
<212> TYPE: DNA
<213> ORGANISM: artificial
<220> FEATURE:
<223> OTHER INFORMATION: Primer

<400> SEQUENCE: 48
aactataaaa aaataaatag ggacctagac ttcaggttgt ctaactcctt ccttttcggt 60
tagagcggat ttattactgc gtcttcttgt cggtgg 96

<210> SEQ ID NO 49
<211> LENGTH: 93
<212> TYPE: DNA
<213> ORGANISM: artificial
<220> FEATURE:
<223> OTHER INFORMATION: Primer

<400> SEQUENCE: 49
ataaaagtat caacaaaaaa ttgttaatat acctctatac tttaacgtca aggagaaaaa 60
accccggatc atgagcacca ccgcgctatt aca 93

<210> SEQ ID NO 50

-continued

<211> LENGTH: 96
<212> TYPE: DNA
<213> ORGANISM: artificial
<220> FEATURE:
<223> OTHER INFORMATION: Primer

<400> SEQUENCE: 50
aactataaaa aaataaatag ggacctagac ttcaggttgt ctaactcctt ccttttcggt 60
tagagcggat ttactacgga atctcgagac tgcttt 96

<210> SEQ ID NO 51
<211> LENGTH: 93
<212> TYPE: DNA
<213> ORGANISM: artificial
<220> FEATURE:
<223> OTHER INFORMATION: Primer

<400> SEQUENCE: 51
ataaaagtat caacaaaaaa ttgttaatat acctctatac tttaacgtca aggagaaaaa 60
accccggatc atggagaagt atagtcggtg gtc 93

<210> SEQ ID NO 52
<211> LENGTH: 96
<212> TYPE: DNA
<213> ORGANISM: artificial
<220> FEATURE:
<223> OTHER INFORMATION: Primer

<400> SEQUENCE: 52
aactataaaa aaataaatag ggacctagac ttcaggttgt ctaactcctt ccttttcggt 60
tagagcggat ttactatctc ttggcccatt gggcgt 96

<210> SEQ ID NO 53
<211> LENGTH: 93
<212> TYPE: DNA
<213> ORGANISM: artificial
<220> FEATURE:
<223> OTHER INFORMATION: Primer

<400> SEQUENCE: 53
ataaaagtat caacaaaaaa ttgttaatat acctctatac tttaacgtca aggagaaaaa 60
accccggatc atgtcgttcg ctacacctgc gca 93

<210> SEQ ID NO 54
<211> LENGTH: 96
<212> TYPE: DNA
<213> ORGANISM: artificial
<220> FEATURE:
<223> OTHER INFORMATION: Primer

<400> SEQUENCE: 54
aactataaaa aaataaatag ggacctagac ttcaggttgt ctaactcctt ccttttcggt 60
tagagcggat ttattagcag gtgaagaaca tgaggg 96

<210> SEQ ID NO 55
<211> LENGTH: 93
<212> TYPE: DNA
<213> ORGANISM: artificial
<220> FEATURE:
<223> OTHER INFORMATION: Primer

<400> SEQUENCE: 55
ataaaagtat caacaaaaaa ttgttaatat acctctatac tttaacgtca aggagaaaaa 60
accccggatc atgagtcaaa gtgacgagtg cca 93

<210> SEQ ID NO 56
<211> LENGTH: 96
<212> TYPE: DNA
<213> ORGANISM: artificial
<220> FEATURE:
<223> OTHER INFORMATION: Primer

<400> SEQUENCE: 56
aactataaaa aaataaatag ggacctagac ttcaggttgt ctaactcctt ccttttcggt 60
tagagcggat ttatcacgtg aagaggcgca actcat 96

<210> SEQ ID NO 57
<211> LENGTH: 93
<212> TYPE: DNA
<213> ORGANISM: artificial
<220> FEATURE:
<223> OTHER INFORMATION: Primer

<400> SEQUENCE: 57
ataaaagtat caacaaaaaa ttgttaatat acctctatac tttaacgtca aggagaaaaa 60
accccggatc atggcggtgt tccacctgta ctc 93

<210> SEQ ID NO 58
<211> LENGTH: 96
<212> TYPE: DNA
<213> ORGANISM: artificial
<220> FEATURE:
<223> OTHER INFORMATION: Primer

<400> SEQUENCE: 58
aactataaaa aaataaatag ggacctagac ttcaggttgt ctaactcctt ccttttcggt 60
tagagcggat ttatcacaga tacttagcct ggtgac 96

<210> SEQ ID NO 59
<211> LENGTH: 93
<212> TYPE: DNA
<213> ORGANISM: artificial
<220> FEATURE:
<223> OTHER INFORMATION: Primer

<400> SEQUENCE: 59
ataaaagtat caacaaaaaa ttgttaatat acctctatac tttaacgtca aggagaaaaa 60
accccggatc atgggcgtgg ctgttgtggg cgt 93

<210> SEQ ID NO 60
<211> LENGTH: 96
<212> TYPE: DNA
<213> ORGANISM: artificial
<220> FEATURE:
<223> OTHER INFORMATION: Primer

<400> SEQUENCE: 60
aactataaaa aaataaatag ggacctagac ttcaggttgt ctaactcctt ccttttcggt 60
tagagcggat ttactacgag ttgtttatga gaaacc 96

<210> SEQ ID NO 61
<211> LENGTH: 93
<212> TYPE: DNA
<213> ORGANISM: artificial
<220> FEATURE:

<223> OTHER INFORMATION: Primer

<400> SEQUENCE: 61
ataaaagtat caacaaaaaa ttgttaatat acctctatac tttaacgtca aggagaaaaa 60
accccggatc atgggacccc gagtggaacc tcc 93

<210> SEQ ID NO 62
<211> LENGTH: 96
<212> TYPE: DNA
<213> ORGANISM: artificial
<220> FEATURE:
<223> OTHER INFORMATION: Primer

<400> SEQUENCE: 62
aactataaaa aaataaatag ggacctagac ttcaggttgt ctaactcctt ccttttcggt 60
tagagcggat ttattaggct tgtttcttcc tcaaac 96

<210> SEQ ID NO 63
<211> LENGTH: 93
<212> TYPE: DNA
<213> ORGANISM: artificial
<220> FEATURE:
<223> OTHER INFORMATION: Primer

<400> SEQUENCE: 63
ataaaagtat caacaaaaaa ttgttaatat acctctatac tttaacgtca aggagaaaaa 60
accccggatc atgacaggcc agcaacacac ttg 93

<210> SEQ ID NO 64
<211> LENGTH: 96
<212> TYPE: DNA
<213> ORGANISM: artificial
<220> FEATURE:
<223> OTHER INFORMATION: Primer

<400> SEQUENCE: 64
aactataaaa aaataaatag ggacctagac ttcaggttgt ctaactcctt ccttttcggt 60
tagagcggat ttactagcgc acatgcagcg tacagt 96

<210> SEQ ID NO 65
<211> LENGTH: 93
<212> TYPE: DNA
<213> ORGANISM: artificial
<220> FEATURE:
<223> OTHER INFORMATION: Primer

<400> SEQUENCE: 65
ataaaagtat caacaaaaaa ttgttaatat acctctatac tttaacgtca aggagaaaaa 60
accccggatc atgtcggcag cccaagtgct caa 93

<210> SEQ ID NO 66
<211> LENGTH: 96
<212> TYPE: DNA
<213> ORGANISM: artificial
<220> FEATURE:
<223> OTHER INFORMATION: Primer

<400> SEQUENCE: 66
aactataaaa aaataaatag ggacctagac ttcaggttgt ctaactcctt ccttttcggt 60
tagagcggat ttattagtat atttccaact gcgctt 96

<210> SEQ ID NO 67
<211> LENGTH: 93
<212> TYPE: DNA
<213> ORGANISM: artificial
<220> FEATURE:
<223> OTHER INFORMATION: Primer

<400> SEQUENCE: 67
ataaaagtat caacaaaaaa ttgttaatat acctctatac tttaacgtca aggagaaaaa 60
accccggatc atggcgaagc tcacgaatgc ggc 93

<210> SEQ ID NO 68
<211> LENGTH: 96
<212> TYPE: DNA
<213> ORGANISM: artificial
<220> FEATURE:
<223> OTHER INFORMATION: Primer

<400> SEQUENCE: 68
aactataaaa aaataaatag ggacctagac ttcaggttgt ctaactcctt ccttttcggt 60
tagagcggat ttatcagtat aattcaagtt cagcgt 96

<210> SEQ ID NO 69
<211> LENGTH: 93
<212> TYPE: DNA
<213> ORGANISM: artificial
<220> FEATURE:
<223> OTHER INFORMATION: Primer

<400> SEQUENCE: 69
ataaaagtat caacaaaaaa ttgttaatat acctctatac tttaacgtca aggagaaaaa 60
accccggatc atggaggctt tcgtcccagt gct 93

<210> SEQ ID NO 70
<211> LENGTH: 96
<212> TYPE: DNA
<213> ORGANISM: artificial
<220> FEATURE:
<223> OTHER INFORMATION: Primer

<400> SEQUENCE: 70
aactataaaa aaataaatag ggacctagac ttcaggttgt ctaactcctt ccttttcggt 60
tagagcggat ttatcagacg taaatgagct tgtagt 96

<210> SEQ ID NO 71
<211> LENGTH: 93
<212> TYPE: DNA
<213> ORGANISM: artificial
<220> FEATURE:
<223> OTHER INFORMATION: Primer

<400> SEQUENCE: 71
ataaaagtat caacaaaaaa ttgttaatat acctctatac tttaacgtca aggagaaaaa 60
accccggatc atggcgagcg aaactcaggc tga 93

<210> SEQ ID NO 72
<211> LENGTH: 96
<212> TYPE: DNA
<213> ORGANISM: artificial
<220> FEATURE:
<223> OTHER INFORMATION: Primer

<400> SEQUENCE: 72
aactataaaa aaataaatag ggacctagac ttcaggttgt ctaactcctt ccttttcggt 60
tagagcggat ttactaaatg atggccagcg tctcgt 96

<210> SEQ ID NO 73
<211> LENGTH: 93
<212> TYPE: DNA
<213> ORGANISM: artificial
<220> FEATURE:
<223> OTHER INFORMATION: Primer

<400> SEQUENCE: 73
ataaaagtat caacaaaaaa ttgttaatat acctctatac tttaacgtca aggagaaaaa 60
accccggatc atgccgcaag cttgtggacg gac 93

<210> SEQ ID NO 74
<211> LENGTH: 96
<212> TYPE: DNA
<213> ORGANISM: artificial
<220> FEATURE:
<223> OTHER INFORMATION: Primer

<400> SEQUENCE: 74
aactataaaa aaataaatag ggacctagac ttcaggttgt ctaactcctt ccttttcggt 60
tagagcggat ttatcagaaa atttctaatt cggcgt 96

<210> SEQ ID NO 75
<211> LENGTH: 93
<212> TYPE: DNA
<213> ORGANISM: artificial
<220> FEATURE:
<223> OTHER INFORMATION: Primer

<400> SEQUENCE: 75
ataaaagtat caacaaaaaa ttgttaatat acctctatac tttaacgtca aggagaaaaa 60
accccggatc atggtcggcg ttgcgcacgc tgc 93

<210> SEQ ID NO 76
<211> LENGTH: 96
<212> TYPE: DNA
<213> ORGANISM: artificial
<220> FEATURE:
<223> OTHER INFORMATION: Primer

<400> SEQUENCE: 76
aactataaaa aaataaatag ggacctagac ttcaggttgt ctaactcctt ccttttcggt 60
tagagcggat ttattaaaaa atctccaggg tggcgt 96

<210> SEQ ID NO 77
<211> LENGTH: 93
<212> TYPE: DNA
<213> ORGANISM: artificial
<220> FEATURE:
<223> OTHER INFORMATION: Primer

<400> SEQUENCE: 77
ataaaagtat caacaaaaaa ttgttaatat acctctatac tttaacgtca aggagaaaaa 60
accccggatc atggacgtgg agaacagtct ttt 93

<210> SEQ ID NO 78
<211> LENGTH: 96
<212> TYPE: DNA
<213> ORGANISM: artificial

<220> FEATURE:
<223> OTHER INFORMATION: Primer

<400> SEQUENCE: 78
aactataaaa aaataaatag ggacctagac ttcaggttgt ctaactcctt ccttttcggt 60
tagagcggat ttattatttt gtcttcttgt caccgg 96

<210> SEQ ID NO 79
<211> LENGTH: 93
<212> TYPE: DNA
<213> ORGANISM: artificial
<220> FEATURE:
<223> OTHER INFORMATION: Primer

<400> SEQUENCE: 79
ataaaagtat caacaaaaaa ttgttaatat acctctatac tttaacgtca aggagaaaaa 60
accccggatc atgacactgg acgacgattc ctc 93

<210> SEQ ID NO 80
<211> LENGTH: 96
<212> TYPE: DNA
<213> ORGANISM: artificial
<220> FEATURE:
<223> OTHER INFORMATION: Primer

<400> SEQUENCE: 80
aactataaaa aaataaatag ggacctagac ttcaggttgt ctaactcctt ccttttcggt 60
tagagcggat ttattagagc tctccgacac gttcgg 96

<210> SEQ ID NO 81
<211> LENGTH: 93
<212> TYPE: DNA
<213> ORGANISM: artificial
<220> FEATURE:
<223> OTHER INFORMATION: Primer

<400> SEQUENCE: 81
ataaaagtat caacaaaaaa ttgttaatat acctctatac tttaacgtca aggagaaaaa 60
accccggatc atgaagttcg acgacaagaa ggt 93

<210> SEQ ID NO 82
<211> LENGTH: 96
<212> TYPE: DNA
<213> ORGANISM: artificial
<220> FEATURE:
<223> OTHER INFORMATION: Primer

<400> SEQUENCE: 82
aactataaaa aaataaatag ggacctagac ttcaggttgt ctaactcctt ccttttcggt 60
tagagcggat ttactacacg gaccctttac gttgct 96

<210> SEQ ID NO 83
<211> LENGTH: 93
<212> TYPE: DNA
<213> ORGANISM: artificial
<220> FEATURE:
<223> OTHER INFORMATION: Primer

<400> SEQUENCE: 83
ataaaagtat caacaaaaaa ttgttaatat acctctatac tttaacgtca aggagaaaaa 60
accccggatc atgctgtcta cgctactatg gct 93

<210> SEQ ID NO 84
<211> LENGTH: 96
<212> TYPE: DNA
<213> ORGANISM: artificial
<220> FEATURE:
<223> OTHER INFORMATION: Primer

<400> SEQUENCE: 84
aactataaaa aaataaatag ggacctagac ttcaggttgt ctaactcctt ccttttcggt 60
tagagcggat ttactatgta gtaagcagtg tgtcgc 96

<210> SEQ ID NO 85
<211> LENGTH: 1170
<212> TYPE: DNA
<213> ORGANISM: Arabidopsis thaliana

<400> SEQUENCE: 85
atggtgattg ctgcagctgt catcgtgcct ttgggccttc tcttcttcat atctggtctc 60
gctgtcaatc tctttcaggc agtttgctat gtactcattc gaccactgtc taagaacaca 120
tacagaaaaa ttaaccgggt ggttgcagaa accttgtggt tggagcttgt atggatagtt 180
gactggtggg ctggagttaa gatccaagtg tttgctgata atgagacctt caatcgaatg 240
ggcaaagaac atgctcttgt cgtttgtaat caccgaagtg atattgattg gcttgtggga 300
tggattctgg ctcagcggtc aggttgcctg ggaagcgcat tagctgtaat gaagaagtct 360
tccaaattcc ttccagtcat aggctggtca atgtggttct cggagtatct ctttctggaa 420
agaaattggg ccaaggatga aagcactcta aagtcaggtc ttcagcgctt gagcgacttc 480
cctcgacctt tctggttagc ccttttttgtg gagggaactc gctttacaga agccaaactt 540
aaagccgcac aagagtatgc agcctcctct gaattgccta tccctcgaaa tgtgttgatt 600
cctcgcacca aaggtttcgt gtcagctgtt agtaatatgc gttcatttgt cccagcaatt 660
tatgatatga cagtgactat tccaaaaacc tctccaccac ccacgatgct aagactattc 720
aaaggacaac cttcagtggt gcatgttcac atcaagtgtc actcgatgaa agacttacct 780
gaatcagatg acgcaattgc acagtggtgc agagatcagt ttgtggctaa ggatgctctg 840
ttagacaaac acatagctgc agacactttc cccggtcaac aagaacagaa cattggccgt 900
cccataaagt cccttgcggt ggttctatca tgggcatgcg tactaactct tggagcaata 960
aagttcctac actgggcaca actcttttct tcatggaaag gtatcacgat atcggcgctt 1020
ggtctaggta tcatcactct ctgtatgcag atcctgatac gctcgtctca gtcagagcgt 1080
tcgaccccag ccaaagtcgt cccagccaag ccaaaagaca atcaccaccc agaatcatcc 1140
tcccaaacag aaacggagaa ggagaagtaa 1170

<210> SEQ ID NO 86
<211> LENGTH: 389
<212> TYPE: PRT
<213> ORGANISM: Arabidopsis thaliana

<400> SEQUENCE: 86

Met Val Ile Ala Ala Ala Val Ile Val Pro Leu Gly Leu Leu Phe Phe
1               5                   10                  15

Ile Ser Gly Leu Ala Val Asn Leu Phe Gln Ala Val Cys Tyr Val Leu
            20                  25                  30

Ile Arg Pro Leu Ser Lys Asn Thr Tyr Arg Lys Ile Asn Arg Val Val
        35                  40                  45

-continued

```
Ala Glu Thr Leu Trp Leu Glu Leu Val Trp Ile Val Asp Trp Trp Ala
    50                  55                  60

Gly Val Lys Ile Gln Val Phe Ala Asp Asn Glu Thr Phe Asn Arg Met
65                  70                  75                  80

Gly Lys Glu His Ala Leu Val Val Cys Asn His Arg Ser Asp Ile Asp
                85                  90                  95

Trp Leu Val Gly Trp Ile Leu Ala Gln Arg Ser Gly Cys Leu Gly Ser
            100                 105                 110

Ala Leu Ala Val Met Lys Lys Ser Ser Lys Phe Leu Pro Val Ile Gly
        115                 120                 125

Trp Ser Met Trp Phe Ser Glu Tyr Leu Phe Leu Glu Arg Asn Trp Ala
    130                 135                 140

Lys Asp Glu Ser Thr Leu Lys Ser Gly Leu Gln Arg Leu Ser Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
            180                 185                 190

Pro Ile Pro Arg Asn Val Leu Ile Pro Arg Thr Lys Gly Phe Val Ser
        195                 200                 205

Ala Val Ser Asn Met Arg Ser Phe Val Pro Ala Ile Tyr Asp Met Thr
    210                 215                 220

Val Thr Ile Pro Lys Thr Ser Pro Pro Pro Thr Met Leu Arg Leu Phe
225                 230                 235                 240

Lys Gly Gln Pro Ser Val Val His Val His Ile Lys Cys His Ser Met
                245                 250                 255

Lys Asp Leu Pro Glu Ser Asp Asp Ala Ile Ala Gln Trp Cys Arg Asp
            260                 265                 270

Gln Phe Val Ala Lys Asp Ala Leu Leu Asp Lys His Ile Ala Ala Asp
        275                 280                 285

Thr Phe Pro Gly Gln Gln Glu Gln Asn Ile Gly Arg Pro Ile Lys Ser
    290                 295                 300

Leu Ala Val Val Leu Ser Trp Ala Cys Val Leu Thr Leu Gly Ala Ile
305                 310                 315                 320

Lys Phe Leu His Trp Ala Gln Leu Phe Ser Ser Trp Lys Gly Ile Thr
                325                 330                 335

Ile Ser Ala Leu Gly Leu Gly Ile Ile Thr Leu Cys Met Gln Ile Leu
            340                 345                 350

Ile Arg Ser Ser Gln Ser Glu Arg Ser Thr Pro Ala Lys Val Val Pro
        355                 360                 365

Ala Lys Pro Lys Asp Asn His His Pro Glu Ser Ser Ser Gln Thr Glu
    370                 375                 380

Thr Glu Lys Glu Lys
385
```

<210> SEQ ID NO 87
<211> LENGTH: 1173
<212> TYPE: DNA
<213> ORGANISM: Brassica napus

<400> SEQUENCE: 87

```
atggcgatgg cagcagcagt gattgtgcct ttggggattc tcttcttcat ttctggcctc      60

gttgtcaatc tcctccaggc agtttgctat gtcctcgttc gacctatgtc taagaacaca     120

tacagaaaga tcaaccgggt ggttgcagaa accttgtggt tggagcttgt ctggatcgtt     180
```

```
gactggtggg ctggagtcaa gatccaagtc tttgctgatg atgagacctt taatcgaatg    240

ggcaaagaac atgctcttgt cgtttgtaat caccgaagtg atattgattg gcttgttgga    300

tggattctcg ctcagaggtc aggttgcctg ggaagcgcat tagctgtaat gaagaagtct    360

tccaaatttc tcccagtcat aggctggtca atgtggttct ccgagtatct gtttcttgaa    420

agaaattggg caaaggatga aagcacttta cagtcaggtc ttcaacgctt gaacgacttc    480

ccacggcctt tctggctagc tctttttgtg gagggaaccc gcttcacaga ggcaaaactt    540

aaagcagcac aagagtacgc agcctcctct gagttgcctg tccctcgaaa tgtgttgatt    600

cctcgcacca aaggttttgt gtcagctgtt agtaacatgc gttcatttgt gccagccata    660

tatgatatga ccgtggctat tccaaaaact tctccacccc caacgatgct aagactattc    720

aaaggacaac cttctgtggt gcatgttcac atcaagtgtc actcgatgaa ggacttgcct    780

gaaccagaag acgaaattgc acagtggtgc agagatcagt ttgtggctaa ggatgcactg    840

ttagacaaac acatagctgc agacactttc cccggtcaga aagaacagaa cattggccgt    900

cccataaagt ctcttgcagt ggttgtatca tgggcatgcc tactaactct tggagcaatg    960

aagttcttac actggtcaaa cctcttttct tcgtggaaag gcatcgcatt atcagccttt   1020

ggtctaggca tcatcactct ctgtatgcag atcctgatcc gctcctctca gtcggagcgt   1080

tcaacacctg ccaaagtcgc tccagccaag ccaaaggaca atcaccagtc aggaccatcc   1140

tcccaaacag aagtggagga gaagcagaag taa                                1173
```

```
<210> SEQ ID NO 88
<211> LENGTH: 390
<212> TYPE: PRT
<213> ORGANISM: Brassica napus

<400> SEQUENCE: 88

Met Ala Met Ala Ala Ala Val Ile Val Pro Leu Gly Ile Leu Phe Phe
1               5                   10                  15

Ile Ser Gly Leu Val Val Asn Leu Leu Gln Ala Val Cys Tyr Val Leu
            20                  25                  30

Val Arg Pro Met Ser Lys Asn Thr Tyr Arg Lys Ile Asn Arg Val Val
        35                  40                  45

Ala Glu Thr Leu Trp Leu Glu Leu Val Trp Ile Val Asp Trp Trp Ala
    50                  55                  60

Gly Val Lys Ile Gln Val Phe Ala Asp Asp Glu Thr Phe Asn Arg Met
65                  70                  75                  80

Gly Lys Glu His Ala Leu Val Val Cys Asn His Arg Ser Asp Ile Asp
                85                  90                  95

Trp Leu Val Gly Trp Ile Leu Ala Gln Arg Ser Gly Cys Leu Gly Ser
            100                 105                 110

Ala Leu Ala Val Met Lys Lys Ser Ser Lys Phe Leu Pro Val Ile Gly
        115                 120                 125

Trp Ser Met Trp Phe Ser Glu Tyr Leu Phe Leu Glu Arg Asn Trp Ala
    130                 135                 140

Lys Asp Glu Ser Thr Leu Gln Ser Gly Leu Gln Arg Leu Asn Asp Phe
145                 150                 155                 160

Pro Arg Pro Phe Trp Leu Ala Leu Phe Val Glu Gly Thr Arg Phe Thr
                165                 170                 175

Glu Ala Lys Leu Lys Ala Ala Gln Glu Tyr Ala Ala Ser Ser Glu Leu
            180                 185                 190
```

-continued

```
Pro Val Pro Arg Asn Val Leu Ile Pro Arg Thr Lys Gly Phe Val Ser
        195                 200                 205

Ala Val Ser Asn Met Arg Ser Phe Val Pro Ala Ile Tyr Asp Met Thr
    210                 215                 220

Val Ala Ile Pro Lys Thr Ser Pro Pro Pro Thr Met Leu Arg Leu Phe
225                 230                 235                 240

Lys Gly Gln Pro Ser Val Val His Val His Ile Lys Cys His Ser Met
                245                 250                 255

Lys Asp Leu Pro Glu Pro Glu Asp Glu Ile Ala Gln Trp Cys Arg Asp
            260                 265                 270

Gln Phe Val Ala Lys Asp Ala Leu Leu Asp Lys His Ile Ala Ala Asp
        275                 280                 285

Thr Phe Pro Gly Gln Lys Glu Gln Asn Ile Gly Arg Pro Ile Lys Ser
    290                 295                 300

Leu Ala Val Val Val Ser Trp Ala Cys Leu Leu Thr Leu Gly Ala Met
305                 310                 315                 320

Lys Phe Leu His Trp Ser Asn Leu Phe Ser Ser Trp Lys Gly Ile Ala
                325                 330                 335

Leu Ser Ala Phe Gly Leu Gly Ile Ile Thr Leu Cys Met Gln Ile Leu
            340                 345                 350

Ile Arg Ser Ser Gln Ser Glu Arg Ser Thr Pro Ala Lys Val Ala Pro
        355                 360                 365

Ala Lys Pro Lys Asp Asn His Gln Ser Gly Pro Ser Ser Gln Thr Glu
    370                 375                 380

Val Glu Glu Lys Gln Lys
385                 390


<210> SEQ ID NO 89
<211> LENGTH: 1389
<212> TYPE: DNA
<213> ORGANISM: Arabidopsis thaliana

<400> SEQUENCE: 89

atggatatga gttcaatggc tggttcaatc ggagtttcgg tagccgtact ccgattcctc      60

ctctgtttcg ttgccacgat ccctgtttca ttcgcttgtc gaatcgtccc gagtagactc     120

ggtaaacact tgtatgccgc tgcttcaggt gctttcctct cttacctctc ctttggcttc     180

tcctccaacc ttcacttcct tgttccgatg acgatcggat atgcttcaat ggcgatttat     240

agacccaagt gtggaatcat cactttcttc ctcggtttcg cttatcttat tggctgtcat     300

gtgttttata tgagtggtga tgcgtggaaa gaaggaggaa tcgattctac tggagcgtta     360

atggtgttga cgctgaaagt catctcatgt tcaatgaatt acaatgatgg gatgttgaag     420

gaggaaggtc tacgtgaagc tcagaagaaa aacagattga ttcagatgcc gtctttgatt     480

gagtactttg gttactgcct ttgttgtggt agccattttg ctggtcctgt ttatgaaatg     540

aaagattatc ttgaatggac cgaagggaaa gggatttggg atactactga gaaaagaaag     600

aagccatcgc cttatggagc tacaatccga gctattttgc aagctgcgat ttgcatggct     660

ctgtatctct atttagtgcc tcaatatccg ttaactcggt tcacagaacc agtgtatcaa     720

gaatggggat tcttgagaaa atttagttac caatacatgg ctggattcac ggctcgttgg     780

aagtattact tcatctggtc aatttcagag gcttctatta tcatctctgg tttgggtttc     840

agtggttgga ctgatgatgc ttcaccaaag cccaaatggg accgtgccaa gaacgtagat     900

attctcggtg ttgaactagc taagagcgcg gttcagattc cacttgtgtg gaacatacaa     960
```

-continued

```
gtcagcacgt ggctccgtca ctatgtgtat gagagacttg tgcagaacgg aaagaaagcg   1020

ggtttcttcc agttactagc tacacaaacc gtcagcgcgg tttggcatgg actgtatcct   1080

ggatatatga tgttctttgt tcagtcagct ttgatgatcg caggctcacg ggttatttac   1140

cggtggcaac aagcgatcag tccgaaaatg gcaatgctga gaaatataat ggtcttcatc   1200

aacttccttt acactgtttt ggttctcaac tactcagccg tcggtttcat ggtgttaagc   1260

ttgcacgaaa cacttaccgc ctacggaagc gtatattaca ttggaacaat catacctgtt   1320

ggattgattc tcctcagtta cgttgtgcct gcaaaacctt caagaccaaa accgcgtaaa   1380

gaagaataa                                                           1389
```

```
<210> SEQ ID NO 90
<211> LENGTH: 462
<212> TYPE: PRT
<213> ORGANISM: Arabidopsis thaliana

<400> SEQUENCE: 90

Met Asp Met Ser Ser Met Ala Gly Ser Ile Gly Val Ser Val Ala Val
1               5                   10                  15

Leu Arg Phe Leu Leu Cys Phe Val Ala Thr Ile Pro Val Ser Phe Ala
            20                  25                  30

Cys Arg Ile Val Pro Ser Arg Leu Gly Lys His Leu Tyr Ala Ala Ala
        35                  40                  45

Ser Gly Ala Phe Leu Ser Tyr Leu Ser Phe Gly Phe Ser Ser Asn Leu
    50                  55                  60

His Phe Leu Val Pro Met Thr Ile Gly Tyr Ala Ser Met Ala Ile Tyr
65                  70                  75                  80

Arg Pro Lys Cys Gly Ile Ile Thr Phe Phe Leu Gly Phe Ala Tyr Leu
                85                  90                  95

Ile Gly Cys His Val Phe Tyr Met Ser Gly Asp Ala Trp Lys Glu Gly
            100                 105                 110

Gly Ile Asp Ser Thr Gly Ala Leu Met Val Leu Thr Leu Lys Val Ile
        115                 120                 125

Ser Cys Ser Met Asn Tyr Asn Asp Gly Met Leu Lys Glu Glu Gly Leu
    130                 135                 140

Arg Glu Ala Gln Lys Lys Asn Arg Leu Ile Gln Met Pro Ser Leu Ile
145                 150                 155                 160

Glu Tyr Phe Gly Tyr Cys Leu Cys Cys Gly Ser His Phe Ala Gly Pro
                165                 170                 175

Val Tyr Glu Met Lys Asp Tyr Leu Glu Trp Thr Glu Gly Lys Gly Ile
            180                 185                 190

Trp Asp Thr Thr Glu Lys Arg Lys Lys Pro Ser Pro Tyr Gly Ala Thr
        195                 200                 205

Ile Arg Ala Ile Leu Gln Ala Ala Ile Cys Met Ala Leu Tyr Leu Tyr
    210                 215                 220

Leu Val Pro Gln Tyr Pro Leu Thr Arg Phe Thr Glu Pro Val Tyr Gln
225                 230                 235                 240

Glu Trp Gly Phe Leu Arg Lys Phe Ser Tyr Gln Tyr Met Ala Gly Phe
                245                 250                 255

Thr Ala Arg Trp Lys Tyr Tyr Phe Ile Trp Ser Ile Ser Glu Ala Ser
            260                 265                 270

Ile Ile Ile Ser Gly Leu Gly Phe Ser Gly Trp Thr Asp Asp Ala Ser
        275                 280                 285

Pro Lys Pro Lys Trp Asp Arg Ala Lys Asn Val Asp Ile Leu Gly Val
```

-continued

```
    290                 295                 300

Glu Leu Ala Lys Ser Ala Val Gln Ile Pro Leu Val Trp Asn Ile Gln
305                 310                 315                 320

Val Ser Thr Trp Leu Arg His Tyr Val Tyr Glu Arg Leu Val Gln Asn
                325                 330                 335

Gly Lys Lys Ala Gly Phe Phe Gln Leu Leu Ala Thr Gln Thr Val Ser
            340                 345                 350

Ala Val Trp His Gly Leu Tyr Pro Gly Tyr Met Met Phe Phe Val Gln
        355                 360                 365

Ser Ala Leu Met Ile Ala Gly Ser Arg Val Ile Tyr Arg Trp Gln Gln
    370                 375                 380

Ala Ile Ser Pro Lys Met Ala Met Leu Arg Asn Ile Met Val Phe Ile
385                 390                 395                 400

Asn Phe Leu Tyr Thr Val Leu Val Leu Asn Tyr Ser Ala Val Gly Phe
                405                 410                 415

Met Val Leu Ser Leu His Glu Thr Leu Thr Ala Tyr Gly Ser Val Tyr
            420                 425                 430

Tyr Ile Gly Thr Ile Ile Pro Val Gly Leu Ile Leu Leu Ser Tyr Val
        435                 440                 445

Val Pro Ala Lys Pro Ser Arg Pro Lys Pro Arg Lys Glu Glu
    450                 455                 460


<210> SEQ ID NO 91
<211> LENGTH: 1398
<212> TYPE: DNA
<213> ORGANISM: Arabidopsis thaliana

<400> SEQUENCE: 91

atggaattgc ttgacatgaa ctcaatggct gcctcaatcg gcgtctccgt cgccgttctc      60

cgtttcctcc tctgtttcgt cgcaacgata ccaatctcat ttttatggcg attcatcccg     120

agtcgactcg gtaaacacat atactcagct gcttctggag ctttcctctc ttatctctcc     180

tttggcttct cctcaaatct tcacttcctt gtcccaatga cgattggtta cgcttcaatg     240

gcgatttatc gacccttgtc tggattcatt actttcttcc taggcttcgc ttatctcatt     300

ggctgtcatg tgttttatat gagtggtgat gcttggaaag aaggaggaat tgattctact     360

ggagctttga tggtattaac actgaaagtg atttcgtgtt cgataaacta caacgatgga     420

atgttgaaag aagaaggtct acgtgaggct cagaagaaga accgtttgat tcagatgcct     480

tctcttattg agtactttgg ttattgcctc tgttgtggaa gccatttcgc tggcccggtt     540

ttcgaaatga aagattatct cgaatggact gaagagaaag gaatttgggc tgtttctgaa     600

aaaggaaaga gaccatcgcc ttatggagca atgattcgag ctgtgtttca agctgcgatt     660

tgtatggctc tctatctcta tttagtacct cagtttccgt taactcggtt cactgaacca     720

gtgtaccaag aatggggatt cttgaagaga tttggttacc aatacatggc gggtttcacg     780

gctcgttgga agtattactt tatatggtct atctcagagg cttctattat tatctctggt     840

ttgggtttca gtggttggac tgatgaaact cagacaaagg ctaaatggga ccgcgctaag     900

aatgtcgata ttttgggggt tgagcttgcc aagagtgcgg ttcagattcc gcttttctgg     960

aacatacaag tcagcacatg gctccgtcac tacgtatatg agagaattgt gaagcccggg    1020

aagaaagcgg gtttcttcca attgctagct acgcaaaccg tcagtgctgt ctggcatgga    1080

ctgtatcctg gatacattat attctttgtg caatcagcat tgatgatcga tggttcgaaa    1140

gctatttacc ggtggcaaca agcaatacct ccgaaaatgg caatgctgag aaatgttttg    1200
```

```
gttctcatca atttcctcta cacagtagtg gttctcaatt actcatccgt cggtttcatg   1260

gttttaagct tgcacgaaac actagtcgcc ttcaagagtg tatattacat tggaacagtt   1320

atacctatcg ctgtgcttct tctcagctac ttagttcctg tgaagcctgt tagaccaaag   1380

accagaaaag aagaataa                                                 1398


<210> SEQ ID NO 92
<211> LENGTH: 465
<212> TYPE: PRT
<213> ORGANISM: Arabidopsis thaliana

<400> SEQUENCE: 92

Met Glu Leu Leu Asp Met Asn Ser Met Ala Ala Ser Ile Gly Val Ser
1               5                   10                  15

Val Ala Val Leu Arg Phe Leu Leu Cys Phe Val Ala Thr Ile Pro Ile
            20                  25                  30

Ser Phe Leu Trp Arg Phe Ile Pro Ser Arg Leu Gly Lys His Ile Tyr
        35                  40                  45

Ser Ala Ala Ser Gly Ala Phe Leu Ser Tyr Leu Ser Phe Gly Phe Ser
    50                  55                  60

Ser Asn Leu His Phe Leu Val Pro Met Thr Ile Gly Tyr Ala Ser Met
65                  70                  75                  80

Ala Ile Tyr Arg Pro Leu Ser Gly Phe Ile Thr Phe Phe Leu Gly Phe
                85                  90                  95

Ala Tyr Leu Ile Gly Cys His Val Phe Tyr Met Ser Gly Asp Ala Trp
            100                 105                 110

Lys Glu Gly Gly Ile Asp Ser Thr Gly Ala Leu Met Val Leu Thr Leu
        115                 120                 125

Lys Val Ile Ser Cys Ser Ile Asn Tyr Asn Asp Gly Met Leu Lys Glu
    130                 135                 140

Glu Gly Leu Arg Glu Ala Gln Lys Lys Asn Arg Leu Ile Gln Met Pro
145                 150                 155                 160

Ser Leu Ile Glu Tyr Phe Gly Tyr Cys Leu Cys Cys Gly Ser His Phe
                165                 170                 175

Ala Gly Pro Val Phe Glu Met Lys Asp Tyr Leu Glu Trp Thr Glu Glu
            180                 185                 190

Lys Gly Ile Trp Ala Val Ser Glu Lys Gly Lys Arg Pro Ser Pro Tyr
        195                 200                 205

Gly Ala Met Ile Arg Ala Val Phe Gln Ala Ala Ile Cys Met Ala Leu
    210                 215                 220

Tyr Leu Tyr Leu Val Pro Gln Phe Pro Leu Thr Arg Phe Thr Glu Pro
225                 230                 235                 240

Val Tyr Gln Glu Trp Gly Phe Leu Lys Arg Phe Gly Tyr Gln Tyr Met
                245                 250                 255

Ala Gly Phe Thr Ala Arg Trp Lys Tyr Tyr Phe Ile Trp Ser Ile Ser
            260                 265                 270

Glu Ala Ser Ile Ile Ile Ser Gly Leu Gly Phe Ser Gly Trp Thr Asp
        275                 280                 285

Glu Thr Gln Thr Lys Ala Lys Trp Asp Arg Ala Lys Asn Val Asp Ile
    290                 295                 300

Leu Gly Val Glu Leu Ala Lys Ser Ala Val Gln Ile Pro Leu Phe Trp
305                 310                 315                 320

Asn Ile Gln Val Ser Thr Trp Leu Arg His Tyr Val Tyr Glu Arg Ile
                325                 330                 335
```

Val Lys Pro Gly Lys Lys Ala Gly Phe Phe Gln Leu Leu Ala Thr Gln
340 345 350

Thr Val Ser Ala Val Trp His Gly Leu Tyr Pro Gly Tyr Ile Ile Phe
355 360 365

Phe Val Gln Ser Ala Leu Met Ile Asp Gly Ser Lys Ala Ile Tyr Arg
370 375 380

Trp Gln Gln Ala Ile Pro Pro Lys Met Ala Met Leu Arg Asn Val Leu
385 390 395 400

Val Leu Ile Asn Phe Leu Tyr Thr Val Val Val Leu Asn Tyr Ser Ser
405 410 415

Val Gly Phe Met Val Leu Ser Leu His Glu Thr Leu Val Ala Phe Lys
420 425 430

Ser Val Tyr Tyr Ile Gly Thr Val Ile Pro Ile Ala Val Leu Leu Leu
435 440 445

Ser Tyr Leu Val Pro Val Lys Pro Val Arg Pro Lys Thr Arg Lys Glu
450 455 460

Glu
465

<210> SEQ ID NO 93
<211> LENGTH: 1398
<212> TYPE: DNA
<213> ORGANISM: Brassica napus

<400> SEQUENCE: 93
atgatatcga tggacatgaa ttcgatggct gcttcgatcg gcgtatcggt cgccgtcctc 60
cgcttcctcc aatgcttcgt cgccacgatc cccgtctcct tcttctggcg aatcgttccg 120
agtcgactcg gcaagcacat ctacgccgcc gcttcaggcg tattcctctc ttacctctcc 180
ttcggcttct cctcaaatct ccacttcctc gttccgatga cgatcggata cgcttccatg 240
gcgatgtatc gacccaagtg tggaatcatc agtttcttcc tcggcttcgc ttatctcatc 300
ggctgtcatg tgttttacat gagtggtgat gcgtggaaag aaggtggcat cgactccact 360
ggagcgttaa tggtgttaac gctgaaggtt atctcatgtg cggttaatta caatgatggg 420
atgttgaagg aggaaggctt acgtgaagct cagaagaaga acagactgat cgagatgccg 480
tctttgatcg agtactttgg ttactgtctc tgttgcggta gccatttcgc tggtcctgtt 540
tacgaaatga aagattatct ccaatggaca gagggaacag gaatttggga tagttccgag 600
aaaagaaagc agccatcgcc ttatttagct acactgcgag ctatcttcca agctgggatt 660
tgcatggctc tgtatctcta tctagtccct cagttcccgt tgactcggtt cactgaacca 720
gtgtaccaag aatgggggtt ttggaagaag tttggttacc agtacatggc gggacagacg 780
gctcgctgga agtattactt catctggtcg atctcggagg cttctattat catctctggt 840
ttgggtttca gtggctggac tgatgatgct tcgccaaaac ccaaatggga ccgtgccaag 900
aacgtggaca tcctcggtgt agaacttgct aagagcgcgg ttcagattcc gcttgtgtgg 960
aacatacaag tcagcacctg gctccgtcac tacgtgtatg agagacttgt gaagagtggg 1020
aagaaagcag gtttctttca gttactaggt acacaaaccg tcagtgcggt ttggcatgga 1080
ctgtatcctg gttacatgat gttctttgtt caatcagctt tgatgattgc tggctcaaga 1140
gttatttacc gatggcaaca agctatcagt ccgaaactag caatcctgag aagtatcatg 1200
gtgttcatca actttcttta caccgtcttg gttctcaact actcagccgt tggtttcatg 1260
gttttaagct tgcacgaaac gctcactgcc tacgggagcg tatattacat tggaacaatc 1320
atacctgttg gattgattct cctcagctac gtggttcctg cgaagccctc tcggccaaag 1380
ccacgtaaag aggaataa 1398

<210> SEQ ID NO 94
<211> LENGTH: 465
<212> TYPE: PRT
<213> ORGANISM: Brassica napus

<400> SEQUENCE: 94

Met Ile Ser Met Asp Met Asn Ser Met Ala Ala Ser Ile Gly Val Ser
1 5 10 15

Val Ala Val Leu Arg Phe Leu Gln Cys Phe Val Ala Thr Ile Pro Val
20 25 30

Ser Phe Phe Trp Arg Ile Val Pro Ser Arg Leu Gly Lys His Ile Tyr
35 40 45

Ala Ala Ala Ser Gly Val Phe Leu Ser Tyr Leu Ser Phe Gly Phe Ser
50 55 60

Ser Asn Leu His Phe Leu Val Pro Met Thr Ile Gly Tyr Ala Ser Met
65 70 75 80

Ala Met Tyr Arg Pro Lys Cys Gly Ile Ile Ser Phe Phe Leu Gly Phe
85 90 95

Ala Tyr Leu Ile Gly Cys His Val Phe Tyr Met Ser Gly Asp Ala Trp
100 105 110

Lys Glu Gly Gly Ile Asp Ser Thr Gly Ala Leu Met Val Leu Thr Leu
115 120 125

Lys Val Ile Ser Cys Ala Val Asn Tyr Asn Asp Gly Met Leu Lys Glu
130 135 140

Glu Gly Leu Arg Glu Ala Gln Lys Lys Asn Arg Leu Ile Glu Met Pro
145 150 155 160

Ser Leu Ile Glu Tyr Phe Gly Tyr Cys Leu Cys Cys Gly Ser His Phe
165 170 175

Ala Gly Pro Val Tyr Glu Met Lys Asp Tyr Leu Gln Trp Thr Glu Gly
180 185 190

Thr Gly Ile Trp Asp Ser Ser Glu Lys Arg Lys Gln Pro Ser Pro Tyr
195 200 205

Leu Ala Thr Leu Arg Ala Ile Phe Gln Ala Gly Ile Cys Met Ala Leu
210 215 220

Tyr Leu Tyr Leu Val Pro Gln Phe Pro Leu Thr Arg Phe Thr Glu Pro
225 230 235 240

Val Tyr Gln Glu Trp Gly Phe Trp Lys Lys Phe Gly Tyr Gln Tyr Met
245 250 255

Ala Gly Gln Thr Ala Arg Trp Lys Tyr Tyr Phe Ile Trp Ser Ile Ser
260 265 270

Glu Ala Ser Ile Ile Ile Ser Gly Leu Gly Phe Ser Gly Trp Thr Asp
275 280 285

Asp Ala Ser Pro Lys Pro Lys Trp Asp Arg Ala Lys Asn Val Asp Ile
290 295 300

Leu Gly Val Glu Leu Ala Lys Ser Ala Val Gln Ile Pro Leu Val Trp
305 310 315 320

Asn Ile Gln Val Ser Thr Trp Leu Arg His Tyr Val Tyr Glu Arg Leu
325 330 335

Val Lys Ser Gly Lys Lys Ala Gly Phe Phe Gln Leu Leu Gly Thr Gln
340 345 350

```
Thr Val Ser Ala Val Trp His Gly Leu Tyr Pro Gly Tyr Met Met Phe
        355                 360                 365

Phe Val Gln Ser Ala Leu Met Ile Ala Gly Ser Arg Val Ile Tyr Arg
    370                 375                 380

Trp Gln Gln Ala Ile Ser Pro Lys Leu Ala Ile Leu Arg Ser Ile Met
385                 390                 395                 400

Val Phe Ile Asn Phe Leu Tyr Thr Val Leu Val Leu Asn Tyr Ser Ala
                405                 410                 415

Val Gly Phe Met Val Leu Ser Leu His Glu Thr Leu Thr Ala Tyr Gly
            420                 425                 430

Ser Val Tyr Tyr Ile Gly Thr Ile Ile Pro Val Gly Leu Ile Leu Leu
        435                 440                 445

Ser Tyr Val Val Pro Ala Lys Pro Ser Arg Pro Lys Pro Arg Lys Glu
    450                 455                 460

Glu
465


<210> SEQ ID NO 95
<211> LENGTH: 1404
<212> TYPE: DNA
<213> ORGANISM: Brassica napus

<400> SEQUENCE: 95

atggaatcgc tcgacatgag ttccatggcg gcctcgatcg gcgtatcggt cgccgttctc      60

cgtttcctac tctgcttcgt cgcaacgatc ccagtctcct tcgcgtggag attcgtcccg     120

agtcgactcg gtaaacacat ctactcagct gcttctggag ccctcctctc ttacctctcc     180

tttggcttct cgtcgaatct tcacttcctc gttcccatga ccattggcta cgcttcgatg     240

gcgatatata gaccaatgtg tggattcatc actttcttcc tcggtttcgc ctatctcatt     300

ggttgtcatg tgttttatat gagtggggat gcttggaaag aaggaggcat tgactctact     360

ggagctttga tggtgttgac gttgaaagtg atatcgtgtt ctataaacta caacgatggg     420

atgttgaagg aagagactct ccgtgaggct cagaggaaga accgtttggt tcggatgcct     480

tctctcattg agtactttgg ttactgcctt tgctgcggaa gccacttcgc tggccctgtc     540

ttcgaaatga aagactatct tgaatggacc gaagagaaag gaatttgggc tgttacttct     600

gggaaaggga agagaccatc gccttacgga gcaacacttc gagctatatt acaagctggg     660

atctgtatgg ctctgtatct ctacttagtc cctcagttcc cattaacccg gttcactgag     720

ccagtgtacc atgaatgggg tttctggaga agattcggtt accaatacat ggccggtttc     780

acggctcgtt ggaagtacta cttcatctgg tcgatctcag aggcttccat catcatctcc     840

ggtttgggtt tcagtggttg gaccgacgaa aacactcaaa caaaggccaa atgggaccgt     900

gcaaagaacg tcgatatctt aggtgttgag ctagccaaga gtgctgttca gattcctctt     960

gtgtggaaca tacaagtcag cacttggctc cgtcactatg tgtatgagag aattgtgaag    1020

ccagggaaga aagctggctt cttccagctg ctagctactc aaaccgttag tgccgtgtgg    1080

catggactgt atcctggata cattatattc tttgttcaat cagcattgat gatcgatggt    1140

tcaaaagcta tttaccgttg gcaacaagca atgcctccga agatggcaat gctgagaagt    1200

gttatggttt tcatcaactt cctctacaca gttttggttc tcaattactc ctccgttggt    1260

ttcatggtat tgagcttgca cgaaacactc gtggcctaca agagtgtata tttcataggc    1320

actgtagtgc ctattgttgt gattctgctc agctatttgg ttcctgtgaa gcctgtgaga    1380

ccaaagaccc ggaaagaaga ataa                                           1404
```

<210> SEQ ID NO 96
<211> LENGTH: 467
<212> TYPE: PRT
<213> ORGANISM: Brassica napus

<400> SEQUENCE: 96

Met Glu Ser Leu Asp Met Ser Ser Met Ala Ala Ser Ile Gly Val Ser
1 5 10 15

Val Ala Val Leu Arg Phe Leu Leu Cys Phe Val Ala Thr Ile Pro Val
20 25 30

Ser Phe Ala Trp Arg Phe Val Pro Ser Arg Leu Gly Lys His Ile Tyr
35 40 45

Ser Ala Ala Ser Gly Ala Leu Leu Ser Tyr Leu Ser Phe Gly Phe Ser
50 55 60

Ser Asn Leu His Phe Leu Val Pro Met Thr Ile Gly Tyr Ala Ser Met
65 70 75 80

Ala Ile Tyr Arg Pro Met Cys Gly Phe Ile Thr Phe Phe Leu Gly Phe
85 90 95

Ala Tyr Leu Ile Gly Cys His Val Phe Tyr Met Ser Gly Asp Ala Trp
100 105 110

Lys Glu Gly Gly Ile Asp Ser Thr Gly Ala Leu Met Val Leu Thr Leu
115 120 125

Lys Val Ile Ser Cys Ser Ile Asn Tyr Asn Asp Gly Met Leu Lys Glu
130 135 140

Glu Thr Leu Arg Glu Ala Gln Arg Lys Asn Arg Leu Val Arg Met Pro
145 150 155 160

Ser Leu Ile Glu Tyr Phe Gly Tyr Cys Leu Cys Cys Gly Ser His Phe
165 170 175

Ala Gly Pro Val Phe Glu Met Lys Asp Tyr Leu Glu Trp Thr Glu Glu
180 185 190

Lys Gly Ile Trp Ala Val Thr Ser Gly Lys Gly Lys Arg Pro Ser Pro
195 200 205

Tyr Gly Ala Thr Leu Arg Ala Ile Leu Gln Ala Gly Ile Cys Met Ala
210 215 220

Leu Tyr Leu Tyr Leu Val Pro Gln Phe Pro Leu Thr Arg Phe Thr Glu
225 230 235 240

Pro Val Tyr His Glu Trp Gly Phe Trp Arg Arg Phe Gly Tyr Gln Tyr
245 250 255

Met Ala Gly Phe Thr Ala Arg Trp Lys Tyr Tyr Phe Ile Trp Ser Ile
260 265 270

Ser Glu Ala Ser Ile Ile Ile Ser Gly Leu Gly Phe Ser Gly Trp Thr
275 280 285

Asp Glu Asn Thr Gln Thr Lys Ala Lys Trp Asp Arg Ala Lys Asn Val
290 295 300

Asp Ile Leu Gly Val Glu Leu Ala Lys Ser Ala Val Gln Ile Pro Leu
305 310 315 320

Val Trp Asn Ile Gln Val Ser Thr Trp Leu Arg His Tyr Val Tyr Glu
325 330 335

Arg Ile Val Lys Pro Gly Lys Lys Ala Gly Phe Phe Gln Leu Leu Ala
340 345 350

Thr Gln Thr Val Ser Ala Val Trp His Gly Leu Tyr Pro Gly Tyr Ile
355 360 365

Ile Phe Phe Val Gln Ser Ala Leu Met Ile Asp Gly Ser Lys Ala Ile

-continued

```
    370                 375                 380

Tyr Arg Trp Gln Gln Ala Met Pro Pro Lys Met Ala Met Leu Arg Ser
385                 390                 395                 400

Val Met Val Phe Ile Asn Phe Leu Tyr Thr Val Leu Val Leu Asn Tyr
                405                 410                 415

Ser Ser Val Gly Phe Met Val Leu Ser Leu His Glu Thr Leu Val Ala
            420                 425                 430

Tyr Lys Ser Val Tyr Phe Ile Gly Thr Val Val Pro Ile Val Val Ile
        435                 440                 445

Leu Leu Ser Tyr Leu Val Pro Val Lys Pro Val Arg Pro Lys Thr Arg
    450                 455                 460

Lys Glu Glu
465
```